United States Patent
Nomura et al.

(10) Patent No.: US 8,334,061 B2
(45) Date of Patent: Dec. 18, 2012

(54) HETEROCYCLIC COMPOUND, AND LIGHT-EMITTING ELEMENT, LIGHT-EMITTING DEVICE, LIGHTING DEVICE, AND ELECTRONIC APPLIANCE USING HETEROCYCLIC COMPOUND

(75) Inventors: Hiroko Nomura, Fukuoka (JP); Hiroshi Kadoma, Kanagawa (JP); Sachiko Kawakami, Kanagawa (JP); Nobuharu Ohsawa, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 305 days.

(21) Appl. No.: 12/748,902

(22) Filed: Mar. 29, 2010

(65) Prior Publication Data

US 2010/0244672 A1 Sep. 30, 2010

(30) Foreign Application Priority Data

Mar. 31, 2009 (JP) ................................. 2009-086675

(51) Int. Cl.
*H01L 51/54* (2006.01)
*C07D 403/10* (2006.01)
(52) U.S. Cl. ........ 428/690; 428/917; 313/504; 313/506; 548/266.4; 548/364.7; 257/40
(58) Field of Classification Search .................. None
See application file for complete search history.

(56) References Cited

U.S. PATENT DOCUMENTS

| | | | |
|---|---|---|---|
| 5,869,929 A * | 2/1999 | Eida et al. .................... 313/501 |
| 6,344,283 B1 | 2/2002 | Inoue et al. | |
| 6,623,872 B2 | 9/2003 | Inoue et al. | |
| 7,097,918 B2 | 8/2006 | Inoue et al. | |
| 8,101,771 B2 | 1/2012 | Nomura et al. | |
| 2002/0102434 A1 | 8/2002 | Inoue et al. | |
| 2004/0110030 A1 | 6/2004 | Inoue et al. | |
| 2007/0196692 A1 | 8/2007 | Ise et al. | |
| 2009/0295278 A1 * | 12/2009 | Lee et al. .................... 313/504 |
| 2010/0060155 A1 | 3/2010 | Seo et al. | |
| 2010/0244674 A1 | 9/2010 | Nomura et al. | |

FOREIGN PATENT DOCUMENTS

| | | |
|---|---|---|
| EP | 0 891 121 A1 | 1/1999 |
| JP | 2005-166680 | 6/2005 |
| JP | 2005-320277 | 11/2005 |
| JP | 2007-227658 | 9/2007 |

(Continued)

OTHER PUBLICATIONS

"Azole." Wikipedia. Wikimedia Foundation, Mar. 17, 2012. Web. Mar. 22, 2012. <http://en.wikipedia.org/wiki/Azole>.*

(Continued)

*Primary Examiner* — Dawn L. Garrett
(74) *Attorney, Agent, or Firm* — Husch Blackwell LLP

(57) ABSTRACT

An object is to provide a novel heterocyclic compound having a bipolar property. Another object is to provide a light-emitting element, a light-emitting device, and an electronic appliance each having high emission efficiency. A heterocyclic compound represented by a general formula (G1), a light-emitting element, a light-emitting device, and an electronic appliance each formed using the heterocyclic compound represented by the general formula (G1) are provided. By use of the heterocyclic compound represented by the general formula (G1) to a light-emitting element, a light-emitting device, and an electronic appliance, the light-emitting element, the light-emitting device, and the electronic appliance can each have high emission efficiency.

31 Claims, 20 Drawing Sheets

FOREIGN PATENT DOCUMENTS

WO      WO 98/30071 A1      7/1998
WO      WO 2010/027004 A1      3/2010

OTHER PUBLICATIONS

Goldsmith, C.R. et al., "C-H Bond Activation by a Ferric Methoxide Complex: Modeling the Rate-Determining Step in the Mechanism of Lipoxygenase," J. Am. Chem. Soc., vol. 124, No. 1, 2002, pp. 83-96.

Onishi.T et al, "A Method of Measuring an Energy Level," *High Molecular EL Materials Development of Light-Emitting High Molecular Compounds*, Kyoritsu Shuppan, Dec. 25, 2004, p. 64-67 (with English translation, pp. 1-3).

Agata, Y. et al, "Syntheses and Properties of Novel Quarterphenylene-Based Materials for Blue Organic Light-Emitting Devices," Chemistry Letters, vol. 36, No. 2, 2007, pp. 316-317.

Ozasa, S. et al, "Syntheses and Physical Properties of Several Octiphenyls Containing Mixed Linkages," Chem. Pharm. Bull., vol. 29, No. 2, 1981, pp. 344-355.

European Search Report re application No. EP 10158693.1, dated Aug. 13, 2010.

International Search Report re application No. PCT/JP2009/065373, dated Oct. 6, 2009.

Written Opinion re application No. PCT/JP2009/065373, dated Oct. 6, 2009.

\* cited by examiner

HETEROCYCLIC COMPOUND, AND LIGHT-EMITTING ELEMENT, LIGHT-EMITTING DEVICE, LIGHTING DEVICE, AND ELECTRONIC APPLIANCE USING HETEROCYCLIC COMPOUND

BACKGROUND OF THE INVENTION

1. Field of the Invention

The present invention relates to a light-emitting material. The present invention relates to a light-emitting element having a pair of electrodes and a layer which includes a light-emitting substance that emits light by application of an electric field. Further, the present invention relates to a light-emitting device having such a light-emitting element.

The present invention relates to a light-emitting device, a lighting device and an electronic appliance each using the light-emitting element.

2. Description of the Related Art

An organic compound can take a wider variety of structures than an inorganic compound, and it is possible to synthesize materials having various functions depending on the molecular design. With those advantages, electronics utilizing a functional organic material has been attracting attention in recent years.

A solar cell, a light-emitting element, an organic transistor, and the like can be given as examples of electronic appliances utilizing an organic compound as a functional material. These are devices taking advantage of electric properties and optical properties of the organic compound. Among them, in particular, a light-emitting element has been making remarkable development.

The light emission mechanism of a light-emitting element is considered to be as follows: when voltage is applied between a pair of electrodes that interpose a light-emitting layer, electrons injected from a cathode and holes injected from an anode are recombined in an emission center of the light-emitting layer to form molecular excitons, and when the molecular excitons relax so as to be in the ground state, energy is released, so that light is emitted. Singlet excitation (S*) and triplet excitation (T*) are known as excited states. Light emission is considered possible through either singlet excitation or triplet excitation. In addition, the statistical generation ratio thereof in a light-emitting element is considered to be S*:T*=1:3.

At room temperature, a compound that is capable of converting a singlet excited state to luminescence (hereinafter, referred to as a fluorescent compound) exhibits only luminescence from the singlet excited state (fluorescence) and no luminescence from the triplet excited state (phosphorescence). Accordingly, the internal quantum efficiency (the ratio of generated photons to injected carriers) in a light-emitting element using a fluorescent compound is assumed to have a theoretical limit of 25% based on the statistical generation ratio, S*:T*=1:3.

On the other hand, by using a compound that converts a triplet excited state into luminescence (hereinafter referred to as a phosphorescent compound), the internal quantum efficiency can be theoretically 75% to 100%. In other words, emission efficiency can be 3 to 4 times as high as that of the fluorescence compound. For these reasons, in order to achieve a highly-efficient light-emitting element, a light-emitting element using a phosphorescent compound has been actively developed recently.

When a light-emitting layer of a light-emitting element is formed using the above phosphorescent compound, in order to suppress concentration quenching of the phosphorescent compound or quenching due to triplet-triplet annihilation (T-T annihilation), the light-emitting layer is often formed so that the phosphorescent compound is dispersed in a matrix of another substance. In that case, the substance used to form the matrix is called a host material, and the substance dispersed throughout the matrix like the phosphorescent compound is called a guest material.

When a phosphorescent compound is used as a guest material, a host material is needed to have triplet excitation energy (the difference in energy between the ground state and the triplet excited state) higher than that of the phosphorescent compound. Therefore, a substance that has high triplet excitation energy has been developed.

For example, in Non-Patent Document 1, a material which has a quaterphenylene skeleton is used as a host material of a phosphorescent compound which exhibits blue light emission and as a hole-transporting layer.

REFERENCE

[Non-Patent Document 1] J. Kido et. al., *Chemistry Letters*, Vol. 36, No. 2, pp. 316-317 (2007)

SUMMARY OF THE INVENTION

Since the host material described in Non-Patent Document 1 is used for the hole-transporting layer, the host material exhibits a hole-transporting property. Therefore, it is expected that holes penetrate a light-emitting layer in a direction of the cathode side in the case where the material described in Non-Patent Document 1 is used as a host material of the light-emitting layer. In Non-Patent Document 1, it is considered that an electron-transporting layer is formed using a hole-blocking material on the cathode side of the light-emitting layer in order that holes are prevented from penetrating the light-emitting layer in the direction of the cathode side. As described above, in the case where the host material of the light-emitting layer has a hole-transporting property, a light-emitting region may possibly exist close to an interface between the light-emitting layer and the electron-transporting layer (a hole-blocking layer).

When the light-emitting region locally exists, quenching due to triplet-triplet annihilation (T-T annihilation) of a light-emitting substance or dispersion of excitons into a layer adjacent to the light-emitting layer (the hole-transporting layer, the electron-transporting layer, or the hole-blocking layer) arises, which results in decrease of emission efficiency.

Thus, the host material is required to have a bipolar property which enables oxidation and reduction and to be stable against both oxidation and reduction. However, when a skeleton having an electron-transporting property and a skeleton having a hole-transporting property are directly bonded to each other, decrease in band gap is caused, which makes it difficult to synthesize a material having high triplet excitation energy. In addition, when a substituent is introduced between the skeleton having an electron-transporting property and the skeleton having a hole-transporting property to expand a conjugation system, problems such as decreases in band gap and triplet excitation energy may occur.

In view of the problems, it is an object of an embodiment of the present invention to provide a novel material having a bipolar property.

It is another object of an embodiment of the present invention to improve emission efficiency of a light-emitting element.

Furthermore, it is another object of an embodiment of the present invention to reduce power consumption of a light-emitting element, a light-emitting device, and an electronic appliance.

The present inventors synthesized a heterocyclic compound in which a heteroaromatic ring skeleton having an electron-transporting property and a skeleton having a hole-transporting property are bonded to each other with a twisted quaterphenylene skeleton that inhibits extension of conjugation therebetween, and have found that the material has high excitation energy and an electron-transporting property and a hole-transporting property (that is, a bipolar property).

A twisted quaterphenylene skeleton that inhibits extension of conjugation is a skeleton in which a benzene ring 2 and a benzene ring 3 are bonded in the ortho position, specifically, as shown in the following structure (Z-1). Two benzene rings which are bonded in the ortho position can be a twisted quaterphenylene skeleton that inhibits extension of conjugation.

(Z-1)

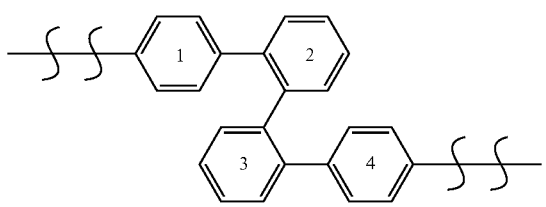

In some cases, even if a compound has a skeleton having an electron-transporting property and a skeleton having a hole-transporting property in a molecule, it does not have a bipolar property. However, a heterocyclic compound of an embodiment of the present invention has a twisted quaterphenylene skeleton that inhibits extension of conjugation in the center; thus, the heterocyclic compound is considered to have a limited intramolecular interaction between a skeleton having an electron-transporting property and a skeleton having a hole-transporting property, which contributes to realization of a bipolar property.

Specifically, an embodiment of the present invention is a heterocyclic compound represented by a general formula (G1).

(G1)

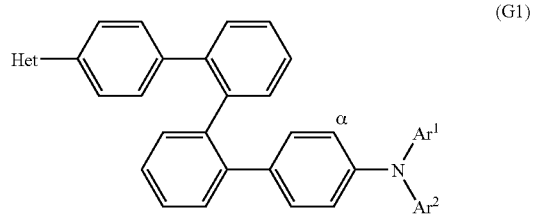

In the general formula (G1), $Ar^1$ and $Ar^2$ independently represent an aryl group having 6 to 10 carbon atoms in a ring and may each have a substituent. In addition, Het represents any one of substituents represented by the following general formulae (S1-1) and (S1-2). Further, $Ar^1$ and an α carbon atom may be bonded to each other or $Ar^1$ and a $Ar^2$ may be bonded to each other to form a carbazole skeleton.

(S1-1)

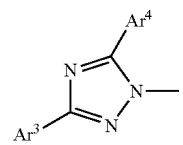

(S1-2)

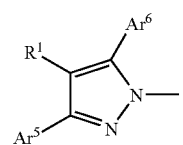

In the general formulae (S1-1) and (S1-2), $Ar^3$ to $Ar^6$ independently represent an aryl group having 6 to 10 carbon atoms in a ring and may each have a substituent. In addition, in the general formula (S1-2), $R^1$ represents any one of a hydrogen atom, an alkyl group having 1 to 4 carbon atoms, and an aryl group having 6 to 10 carbon atoms in a ring.

In addition, another embodiment of the present invention is a heterocyclic compound which is represented by a general formula (G2).

(G2)

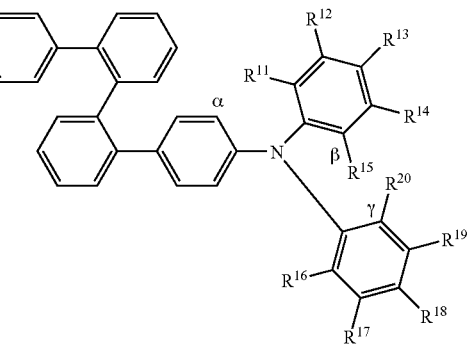

In the general formula (G2), $R^{11}$ to $R^{20}$ independently represent a hydrogen atom, an alkyl group having 1 to 4 carbon atoms, or an aryl group having 6 to 10 carbon atoms in a ring. In addition, Het represents any one of substituents represented by the following general formulae (S1-1) and (S1-2). Further, any two of an α carbon atom, a β carbon atom, and a γ carbon atom may be bonded to each other to form a carbazole skeleton.

(S1-1)

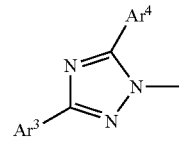

(S1-2)

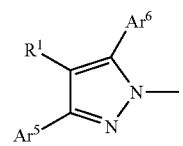

In the general formulae (S1-1) and (S1-2), $Ar^3$ to $Ar^6$ independently represent an aryl group having 6 to 10 carbon atoms in a ring and may each have a substituent. In addition, in the general formula (S1-2), $R^1$ represents any one of a hydrogen atom, an alkyl group having 1 to 4 carbon atoms, and an aryl group having 6 to 10 carbon atoms in a ring.

In addition, another embodiment of the present invention is a heterocyclic compound which is represented by the general formula (G2).

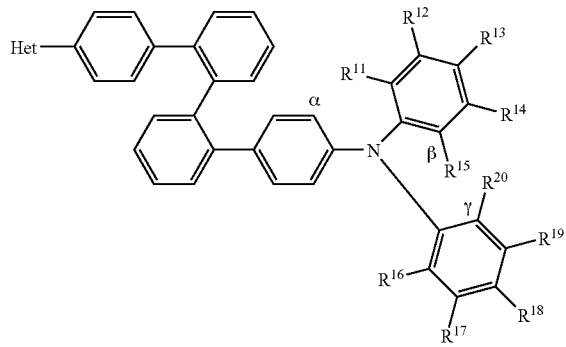

(G2)

In the general formula (G2), $R^{11}$ to $R^{20}$ independently represent a hydrogen atom, an alkyl group having 1 to 4 carbon atoms, or an aryl group having 6 to 10 carbon atoms in a ring. In addition, Het represents any one of substituents represented by the following general formulae (S2-1) and (S2-2). Further, any two of an α carbon atom, a β carbon atom, and a γ carbon atom may be bonded to each other to form a carbazole skeleton.

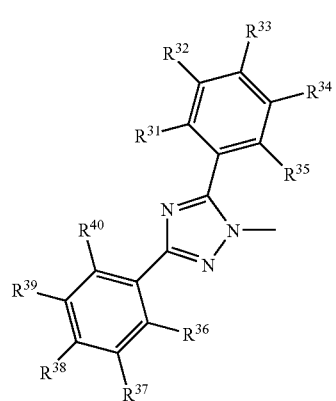

(S2-1)

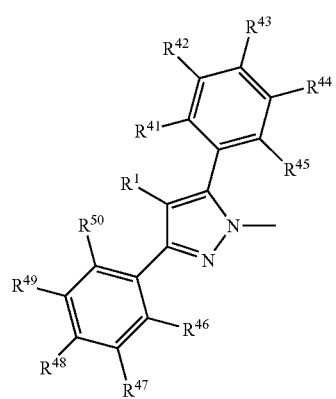

(S2-2)

In the general formulae (S2-1) and (S2-2), $R^1$ and $R^{31}$ to $R^{50}$ independently represent any one of a hydrogen atom, an alkyl group having 1 to 4 carbon atoms, and an aryl group having 6 to 10 carbon atoms in a ring.

In addition, another embodiment of the present invention is a heterocyclic compound which is represented by the general formula (G2).

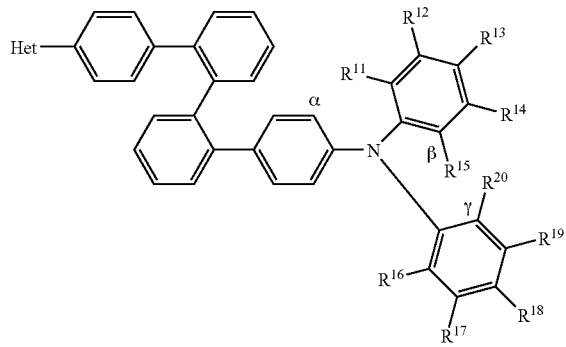

(G2)

In the general formula (G2), $R^{11}$ to $R^{20}$ independently represent a hydrogen atom, an alkyl group having 1 to 4 carbon atoms, or an aryl group having 6 to 10 carbon atoms in a ring. In addition, Het represents any one of substituents represented by the following structural formula (S3-1) and the following general formula (S4-1). Further, any two of an α carbon atom, a β carbon atom, and a γ carbon atom may be bonded to each other to form a carbazole skeleton.

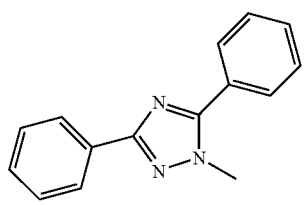

(S3-1)

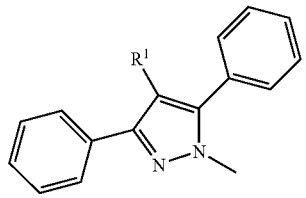

(S4-1)

In the general formula (S4-1), $R^1$ represents any one of a hydrogen atom, an alkyl group having 1 to 4 carbon atoms, and an aryl group having 6 to 10 carbon atoms in a ring.

In addition, another embodiment of the present invention is a heterocyclic compound which is represented by a general formula (G3).

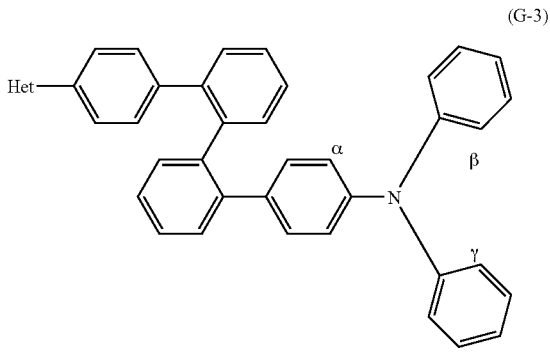

(G-3)

In the general formula (G3), Het represents any one of substituents represented by the following structural formula (S3-1) and the following general formula (S4-1). Further, any two of an α carbon atom, a β carbon atom, and a γ carbon atom may be bonded to each other to form a carbazole skeleton.

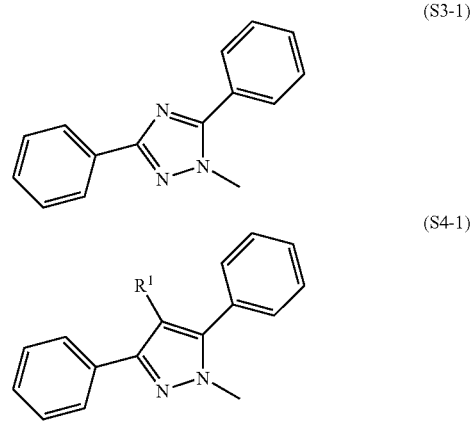

(S3-1)

(S4-1)

In the general formula (S4-1), $R^1$ represents any one of a hydrogen atom, an alkyl group having 1 to 4 carbon atoms, and an aryl group having 6 to 10 carbon atoms in a ring.

Since the heterocyclic compounds which are embodiments of the present invention and represented by the general formulae (G1) to (G3) described above each have a bipolar property, any of them can be favorably used as a material for a light-emitting element or an organic device such as an organic transistor. Therefore, another embodiment of the present invention is a light-emitting element including any of the above heterocyclic compounds.

In addition, since any of the heterocyclic compounds of an embodiment of the present invention has high excitation energy, it is optimal for use as a host material of a light-emitting layer in a light-emitting element. Therefore, another embodiment of the present invention is a light-emitting element including a light-emitting layer including a light-emitting substance and any of the above heterocyclic compounds.

In particular, since the heterocyclic compound of an embodiment of the present invention has high triplet excitation energy, a phosphorescent compound is favorably used for the light-emitting substance. With such a structure, a light-emitting element that is excellent in emission efficiency and reliability can be obtained.

Furthermore, a light-emitting element in which a layer that includes any of the heterocyclic compounds of an embodiment of the present invention is provided in contact with a light-emitting layer is another embodiment of the present invention. Since any of the heterocyclic compounds of an embodiment of the present invention is a bipolar material which has a high electron-transporting property and a high hole-transporting property, it can also be used as a carrier-transporting material for a functional layer of a light-emitting element.

Since any of the heterocyclic compounds of an embodiment of the present invention has high excitation energy, it is used as a functional layer of a light-emitting element, so that the diffusion of excitons generated in the light-emitting layer to other layers can be prevented. As a result, the light-emitting element can have high emission efficiency.

The thus obtained light-emitting element of an embodiment of the present invention can realize high emission efficiency, and thus a light-emitting device (such as an image display device) that uses this light-emitting element can realize low power consumption. Thus, another embodiment of the present invention includes a light-emitting device which uses the above light-emitting element. In addition, another embodiment of the present invention includes an electronic appliance which uses the light-emitting device.

Note that the light-emitting device in this specification includes an image display device that uses a light-emitting element. Further, the category of the light-emitting device includes a module including a light-emitting element attached with a connector such as an anisotropic conductive film, tape automated bonding (TAB) tape, or a tape carrier package (TCP); a module in which the top of the TAB tape or the TCP is provided with a printed wiring board; and a module in which an integrated circuit (IC) is directly mounted on a light-emitting element by a chip on glass (COG) method. Furthermore, light-emitting devices that are used in lighting equipment and the like are also included.

The heterocyclic compounds which are embodiments of the present invention are each a novel bipolar material. Further, the heterocyclic compounds of embodiments of the present invention each have high electrochemical stability.

In addition, any of the heterocyclic compounds which are embodiments of the present invention is used for a light-emitting element, so that the light-emitting element can have high emission efficiency.

Further, in any of the heterocyclic compounds of embodiments of the present invention, a heteroaromatic ring skeleton having an electron-transporting property and a skeleton having a hole-transporting property are bonded to each other with a twisted quaterphenylene skeleton that inhibits extension of conjugation therebetween; thus, the molecular weight can be increased without high triplet excitation energy decreased, and a sterically bulky molecular skeleton can be formed. In addition, the heterocyclic compound can have a large band gap. Such a material is used for a light-emitting element, whereby the film quality can be stabilized.

Furthermore, by forming a light-emitting device using the above light-emitting element, the light-emitting device can have low power consumption. Moreover, by applying such a light-emitting device to an electronic appliance, the electronic appliance can have low power consumption.

DETAILED DESCRIPTION OF THE INVENTION

Figure 1A:
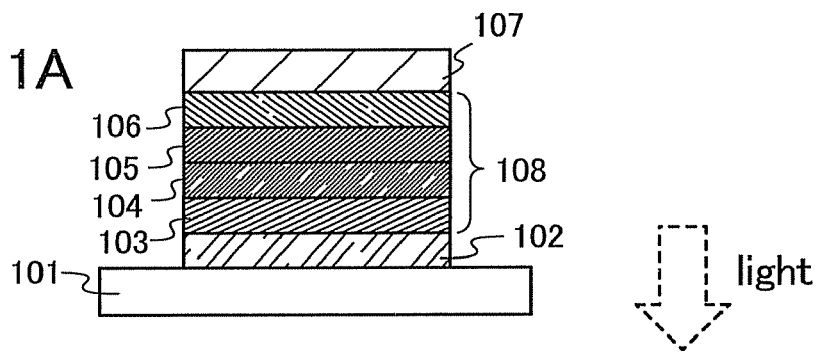
FIGS. 1A to 1C each illustrate a light-emitting element according to an embodiment of the present invention.

The embodiments and examples of the present invention are described in detail with reference to drawings. Note that the present invention is not limited to the description below, and it is easily understood by those skilled in the art that modes and details can be modified in various ways without departing from the spirit and scope of the present invention. Accordingly, the present invention should not be construed as being limited to the description of the embodiments and examples given below.

Embodiment 1

In this embodiment, heterocyclic compounds each of which is an embodiment of the present invention will be described.

As a result of intensive studies, the present inventors have found that, a bipolar organic compound having high triplet excitation energy can be obtained by introducing a skeleton having an electron-transporting property and a skeleton having a hole-transporting property into a molecule with a twisted quaterphenylene skeleton that inhibits extension of conjugation therebetween.

A heterocyclic compound which is an embodiment of the present invention is represented by a general formula (G1).

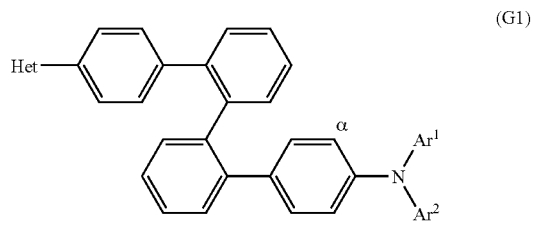

In the general formula (G1), $Ar^1$ and $Ar^2$ independently represent an aryl group having 6 to 10 carbon atoms in a ring and may each have a substituent. In addition, Het represents any one of substituents represented by the following general formulae (S1-1) and (S1-2). Further, $Ar^1$ and an α carbon atom may be bonded to each other or $Ar^1$ and $Ar^2$ may be bonded to each other to form a carbazole skeleton.

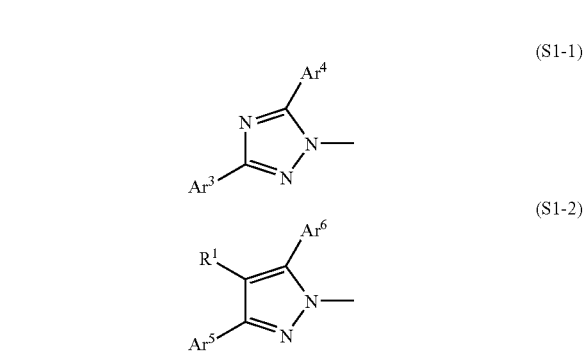

In the general formulae (S1-1) and (S1-2), $Ar^3$ to $Ar^6$ independently represent an aryl group having 6 to 10 carbon atoms in a ring and may each have a substituent. In addition, in the general formula (S1-2), $R^1$ represents any one of a hydrogen atom, an alkyl group having 1 to 4 carbon atoms, and an aryl group having 6 to 10 carbon atoms in a ring.

Note that $Ar^1$ and $Ar^2$ in the general formula (G1) may independently have another substituent; in such a case, an alkyl group having 1 to 4 carbon atoms, an aryl group having 6 to 10 carbon atoms in a ring, and the like can be given as the substituent. Note that the carbon atoms of the aryl group described in this specification refer to carbon atoms that form a ring of the main skeleton, and carbon atoms of a substituent bonded thereto are not included therein. As specific structures of $Ar^1$ and $Ar^2$ in the general formula (G1), there are substituents represented by structural formulae (1-1) to (1-21).

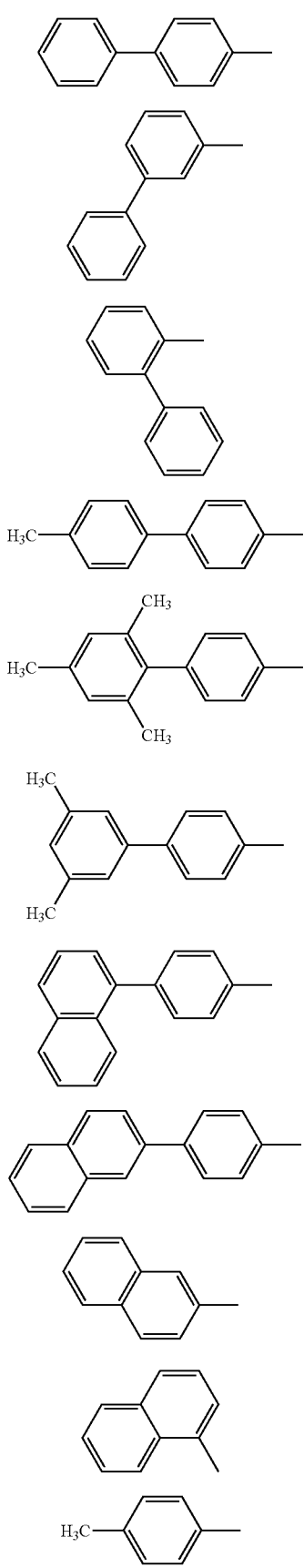

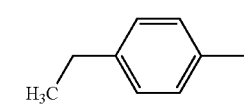
(1-13)

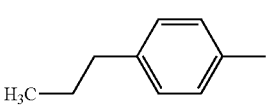
(1-14)

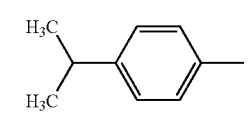
(1-15)

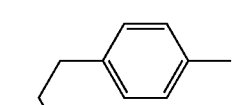
(1-16)

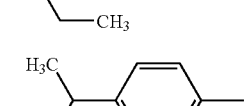
(1-17)

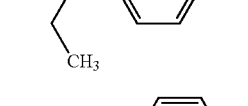
(1-18)

Ar³ to Ar⁶ in the general formulae (S1-1) and (S1-2) may each have another substituent. As the substituent, an alkyl group having 1 to 4 carbon atoms, an aryl group having 6 to 10 carbon atoms in a ring, and the like can be given. As specific structures of Ar³ to Ar⁶ in the general formulae (S1-1) and (S1-2), there are substituents represented by the structural formulae (1-1) to (1-21) shown above.

In addition, as a specific structure of R¹ in the general formula (S1-2), there are substituents represented by structural formulae (2-1) to (2-22).

H—  (2-1)

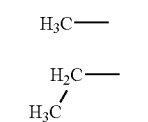 (2-2)

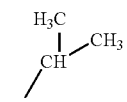 (2-3)

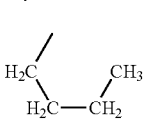 (2-4)

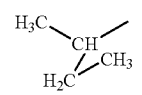 (2-5)

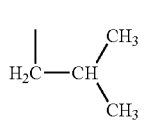 (2-6)

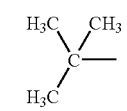 (2-7)

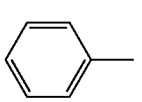 (2-8)

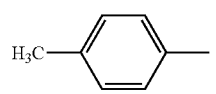 (2-9)

(2-10)

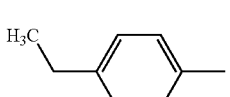 (2-11)

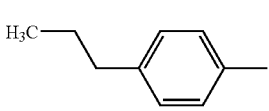 (2-12)

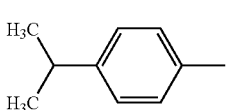 (2-13)

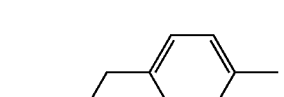 (2-14)

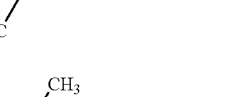 (2-15)

(2-16)

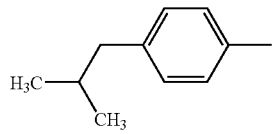 (2-17)

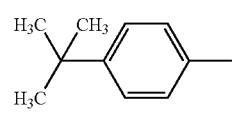 (2-18)

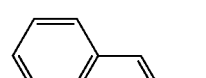 (2-19)

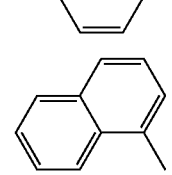 (2-20)

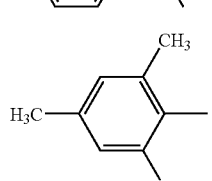 (2-21)

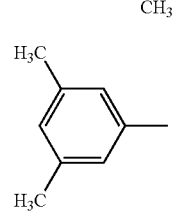 (2-22)

In addition, an embodiment of the present invention is a heterocyclic compound which is represented by a general formula (G2).

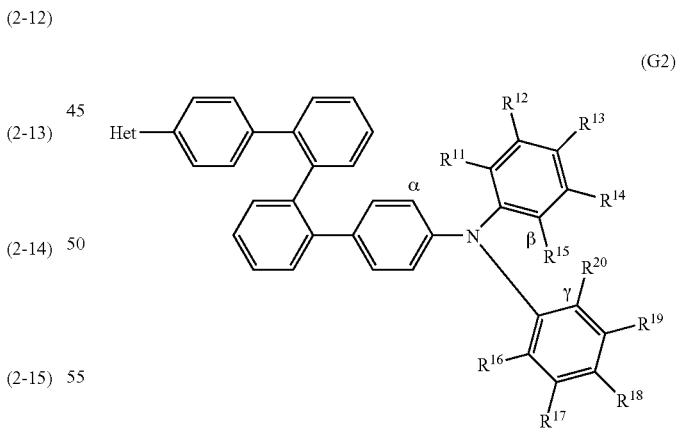

(G2)

In the general formula (G2), $R^{11}$ to $R^{20}$ independently represent a hydrogen atom, an alkyl group having 1 to 4 carbon atoms, or an aryl group having 6 to 10 carbon atoms in a ring. Further, any two of an α carbon atom, a β carbon atom, and a γ carbon atom may be bonded to each other to form a carbazole skeleton.

In addition, in the general formula (G2), Het represents any one of substituents represented by the following general formulae (S1-1) and (S1-2).

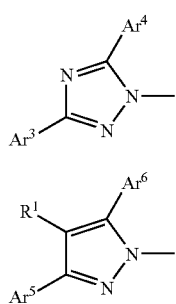
(S1-1)

(S1-2)

In the general formulae (S1-1) and (S1-2), $Ar^3$ to $Ar^6$ independently represent an aryl group having 6 to 10 carbon atoms in a ring and may each have a substituent. As the substituent, an alkyl group having 1 to 4 carbon atoms and an aryl group having 6 to 10 carbon atoms in a ring can be given. In addition, in the general formula (S1-2), $R^1$ represents any one of a hydrogen atom, an alkyl group having 1 to 4 carbon atoms, and an aryl group having 6 to 10 carbon atoms in a ring.

As specific structures of $R^{11}$ to $R^{20}$ in the general formula (G2), there are substituents represented by the structural formulae (2-1) to (2-22), and the like.

Note that in the general formula (G2), Het preferably represents any one of substituents represented by the following general formulae (S2-1) and (S2-2).

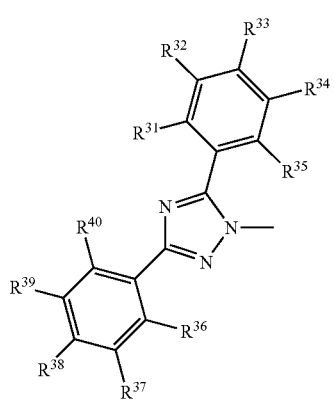
(S2-1)

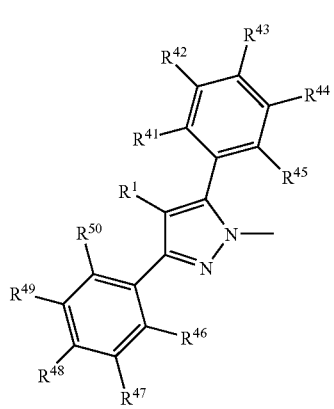
(S2-2)

In the general formulae (S2-1) and (S2-2), $R^1$ and $R^{31}$ to $R^{50}$ independently represent any one of a hydrogen atom, an alkyl group having 1 to 4 carbon atoms, and an aryl group having 6 to 10 carbon atoms in a ring.

As specific structures of $R^1$ and $R^{31}$ to $R^{50}$ in the general formulae (S2-1) and (S2-2), there are substituents represented by the structural formulae (2-1) to (2-22) shown above, and the like.

Note that in the general formula (G2), Het more preferably represents any one of substituents represented by the following structural formula (S3-1) and general formula (S4-1).

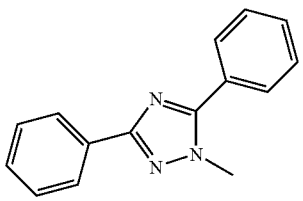
(S3-1)

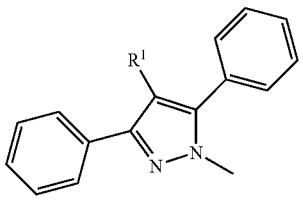
(S4-1)

In the general formula (S4-1), $R^1$ represents any one of a hydrogen atom, an alkyl group having 1 to 4 carbon atoms, and an aryl group having 6 to 10 carbon atoms in a ring.

Note that as a specific structure of $R^1$ in the general formula (S4-1), there are substituents represented by the structural formulae (2-1) to (2-22) shown above, and the like.

In addition, an embodiment of the present invention is a heterocyclic compound which is represented by a general formula (G3).

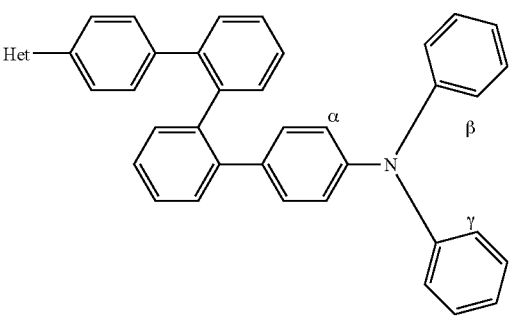
(G-3)

In the general formula (G3), Het represents any one of substituents represented by the following structural formula (S3-1) and general formula (S4-1). Further, any two of an α carbon atom, a β carbon atom, and a γ carbon atom may be bonded to each other to form a carbazole skeleton.

(S3-1)
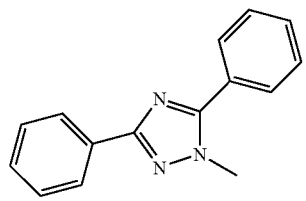
(S4-1)
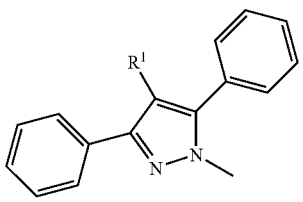
In the general formula (S4-1), $R^1$ represents any one of a hydrogen atom, an alkyl group having 1 to 4 carbon atoms, and an aryl group having 6 to 10 carbon atoms in a ring.
For example, specific examples of the heterocyclic compounds of this embodiment include heterocyclic compounds represented by structural formulae (100) to (313). However, this embodiment is not limited thereto.
(100)
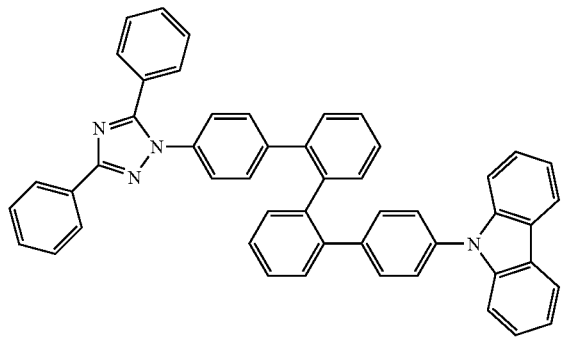
(101)
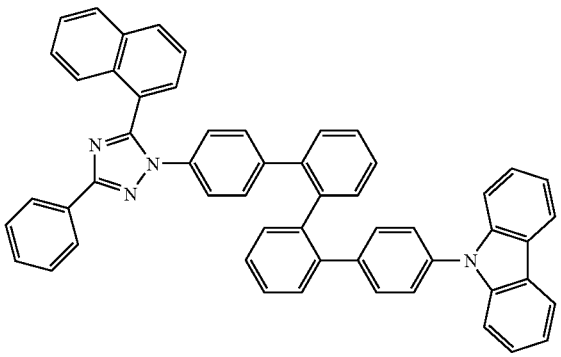
(102)
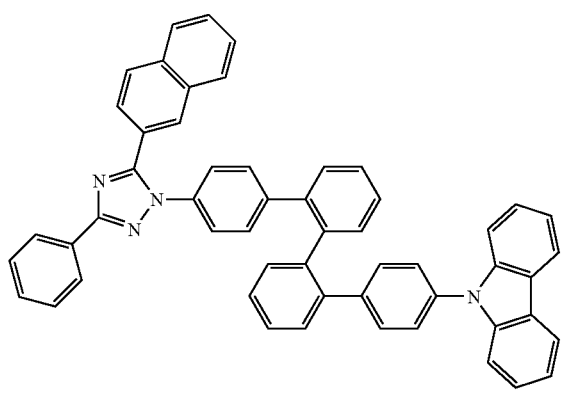
(103)
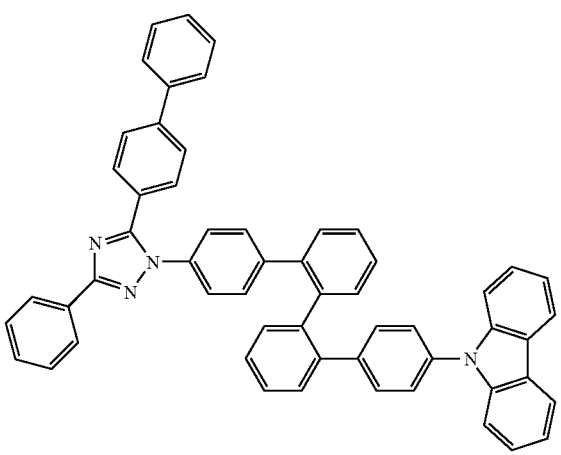

(104)
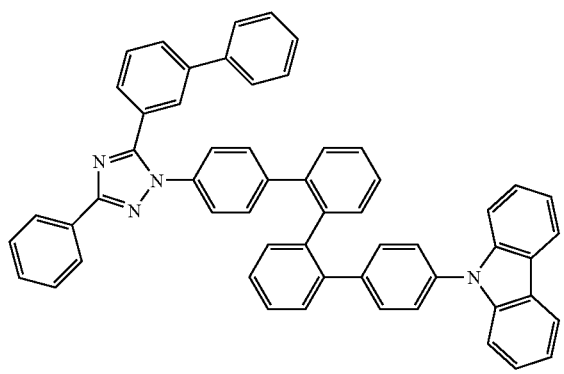
(105)
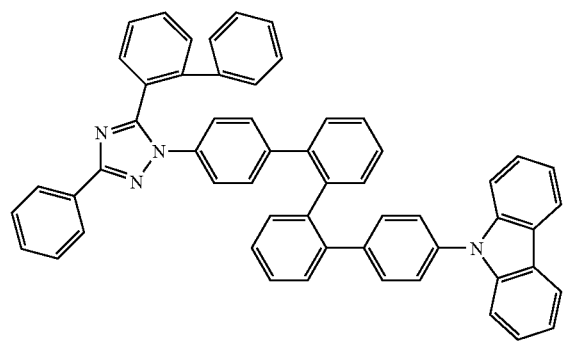
(106)
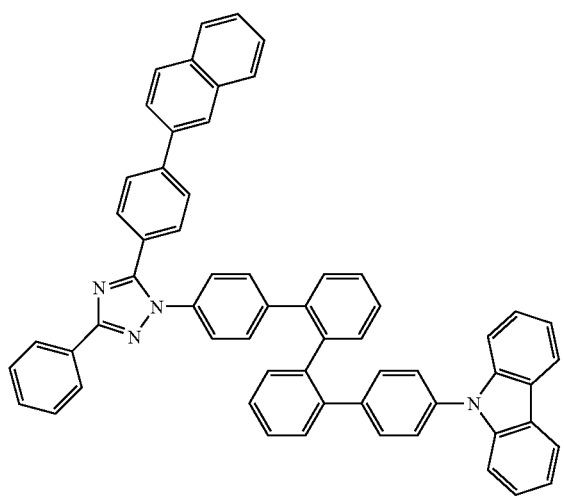
(107)
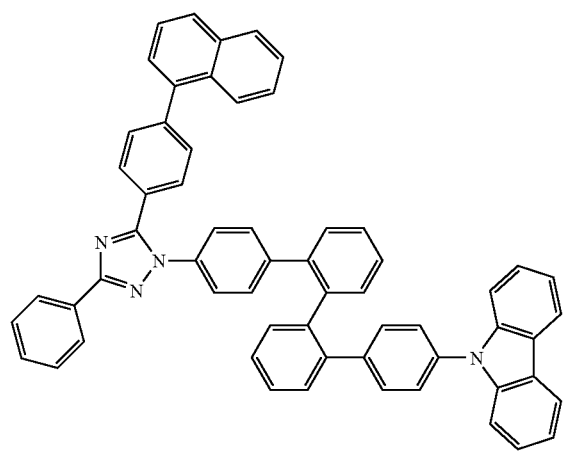
(108)
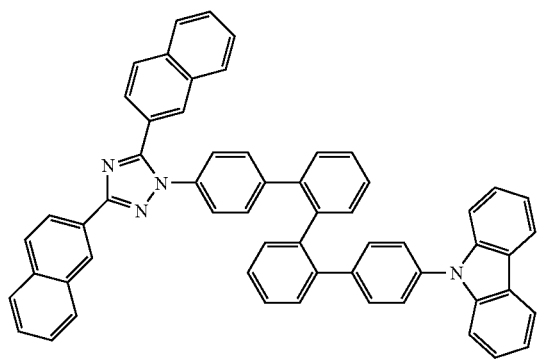
(109)
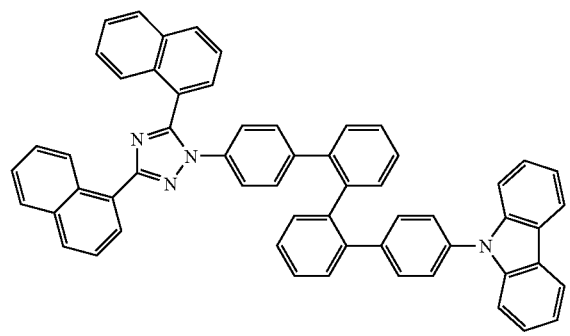

-continued
(110)
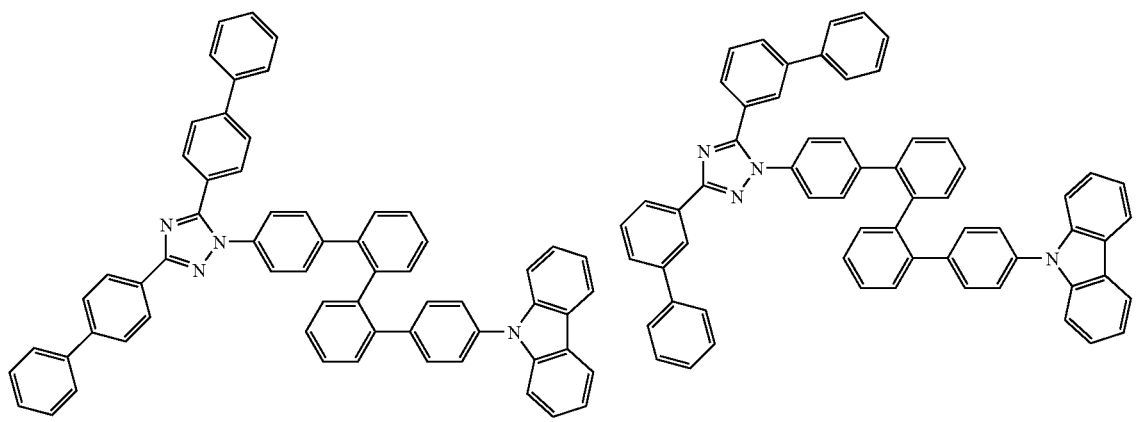
(111)
(112)
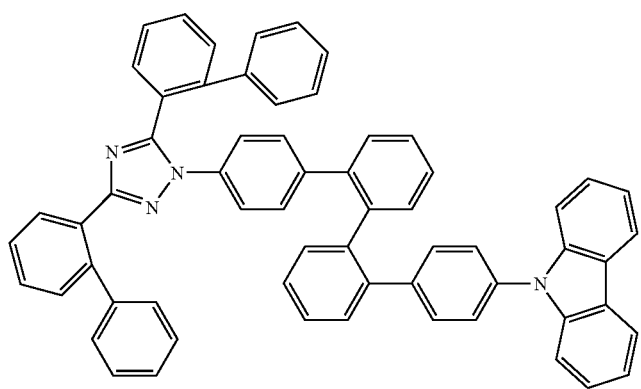
(113)
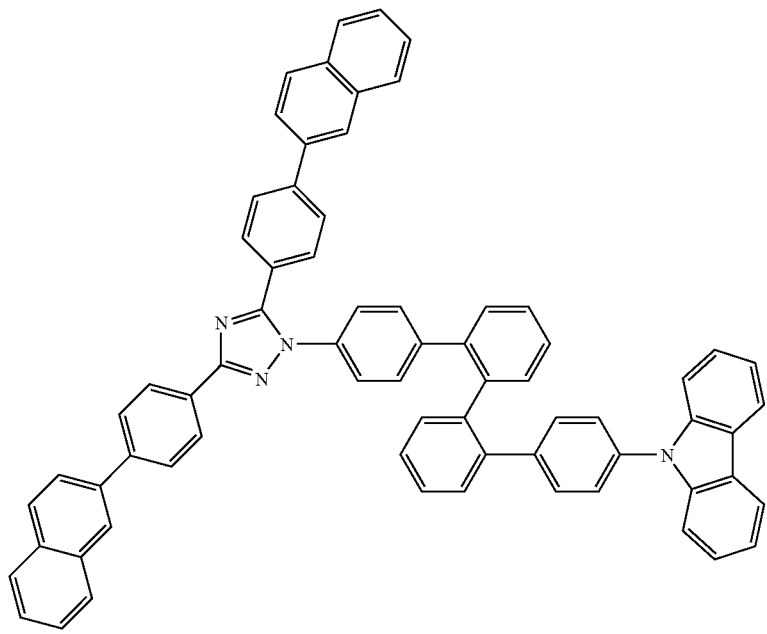

-continued
(114)
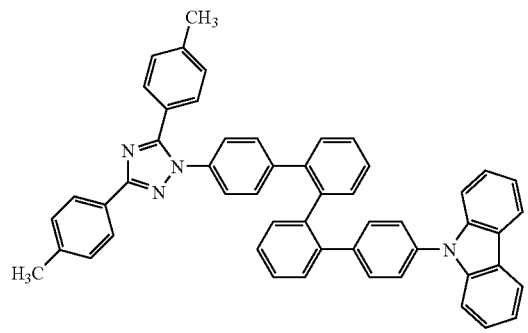
(115)
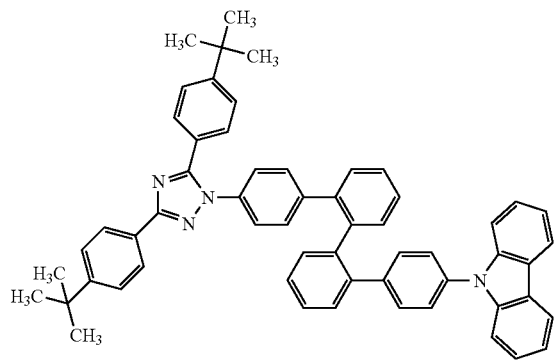
(116)
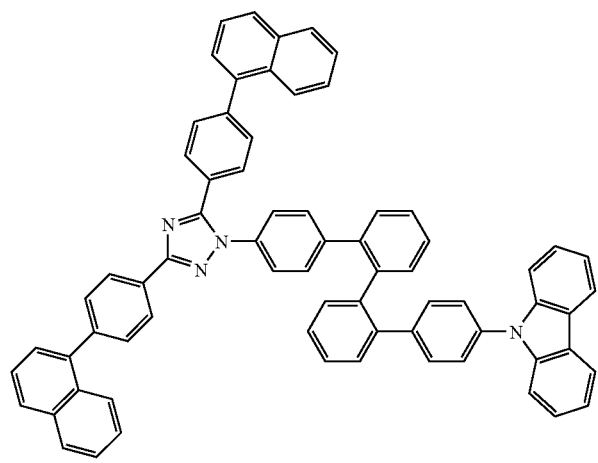
(117)
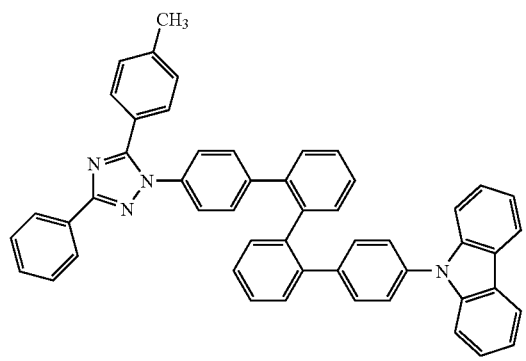
(118)
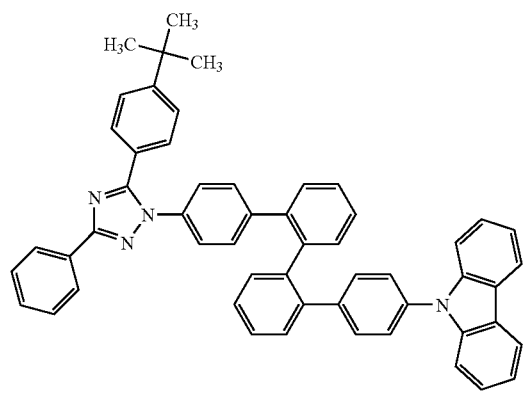
(119)
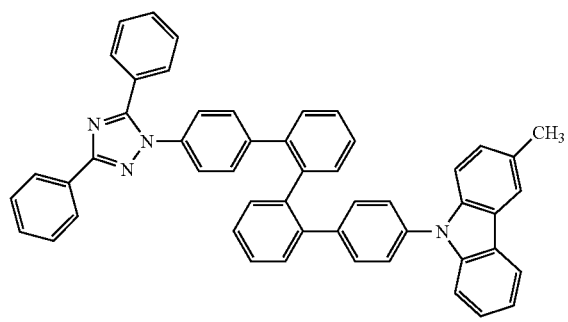
(120)
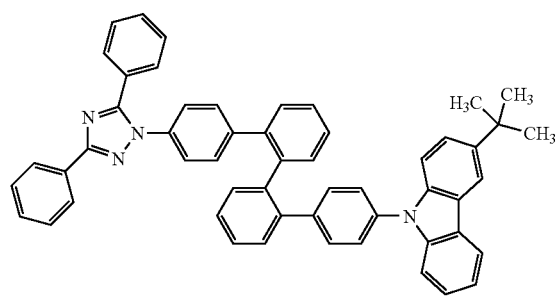
(121)
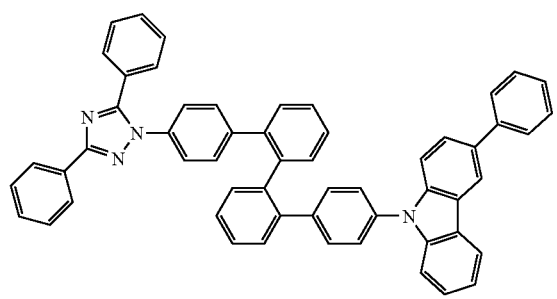

-continued
(122) 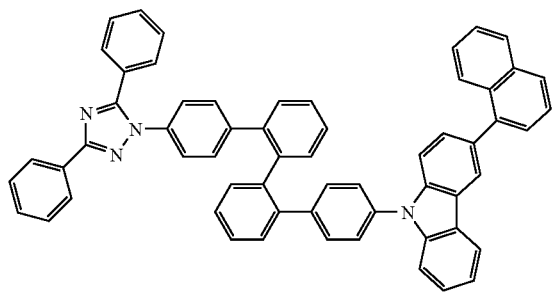
(123) 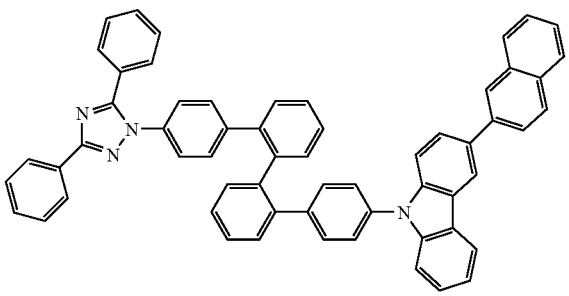
(124) 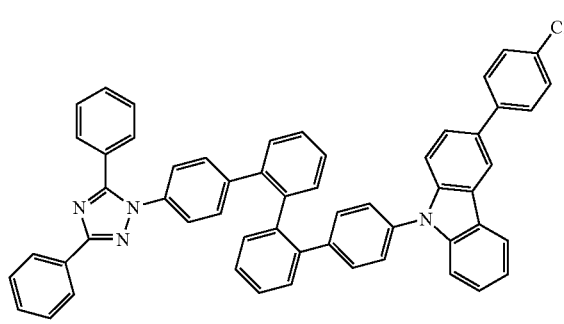
(125) 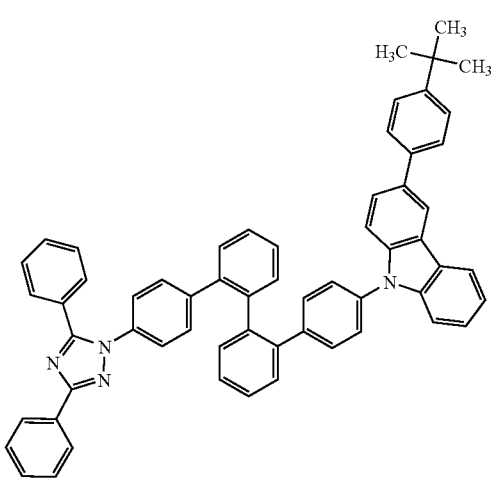
(126) 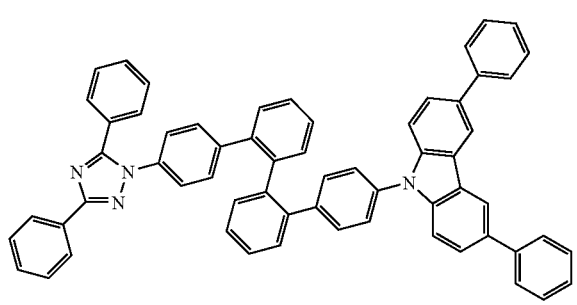
(127) 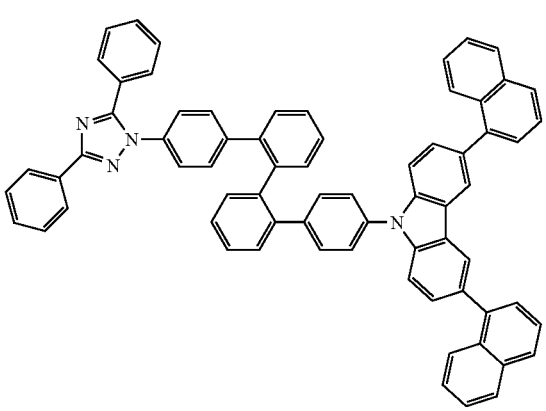

(128)
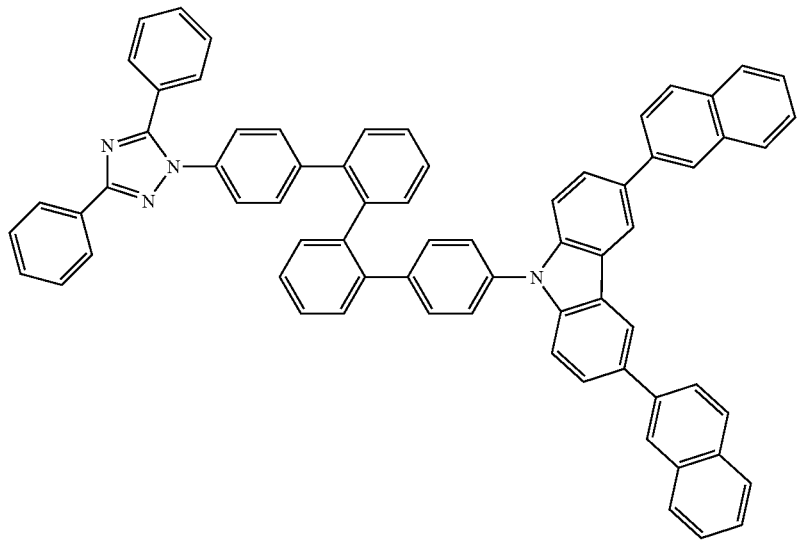
(129)
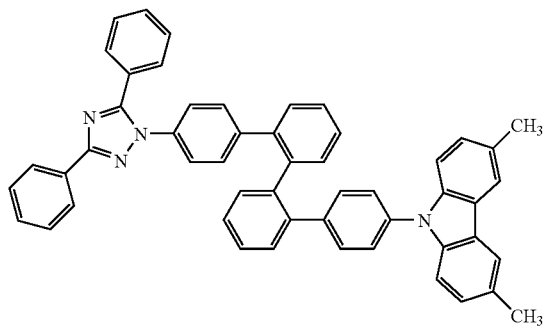
(130)
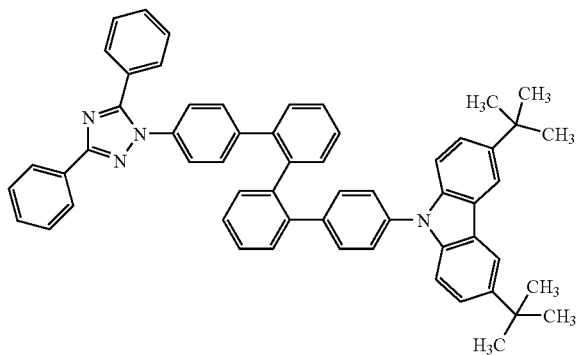
(131)
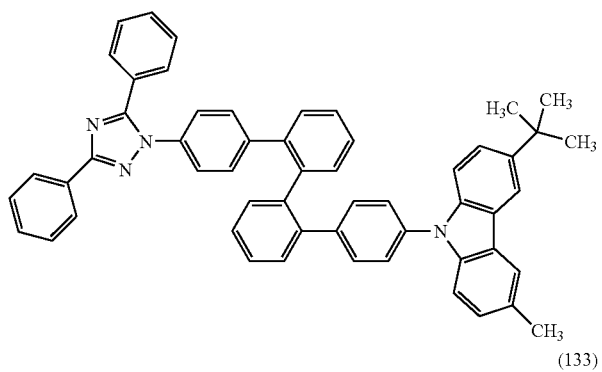
(132)
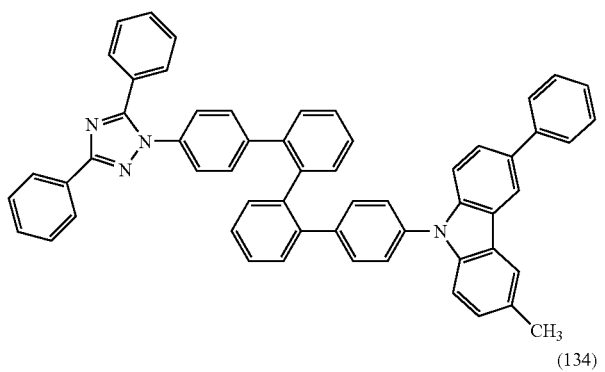
(133)
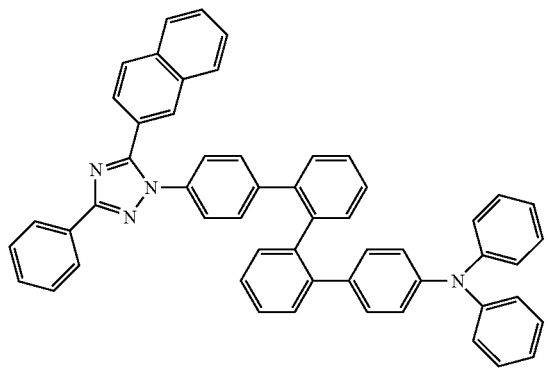
(134)
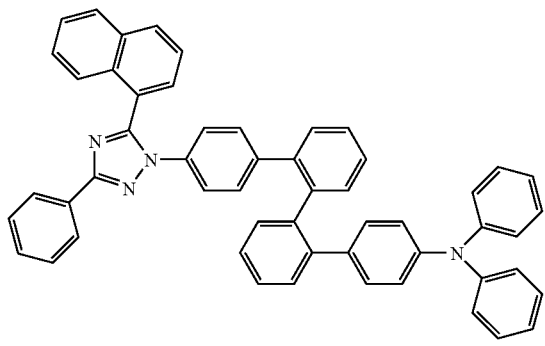

-continued
(135)
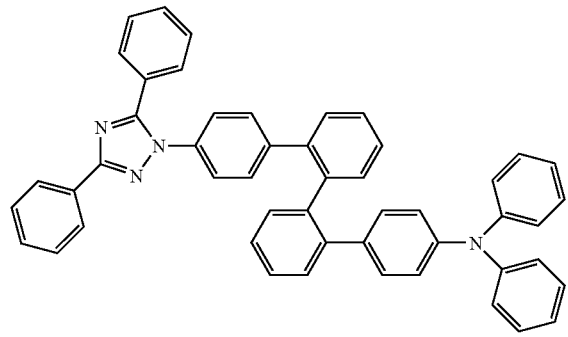
(136)
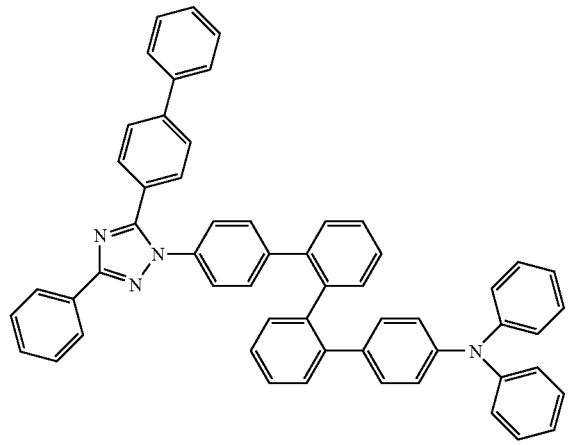
(137)
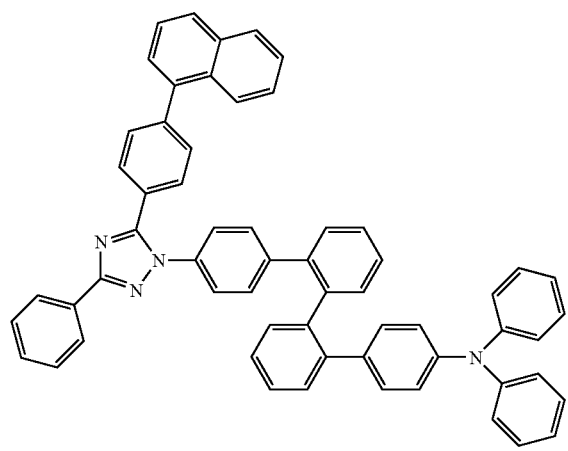
(138)
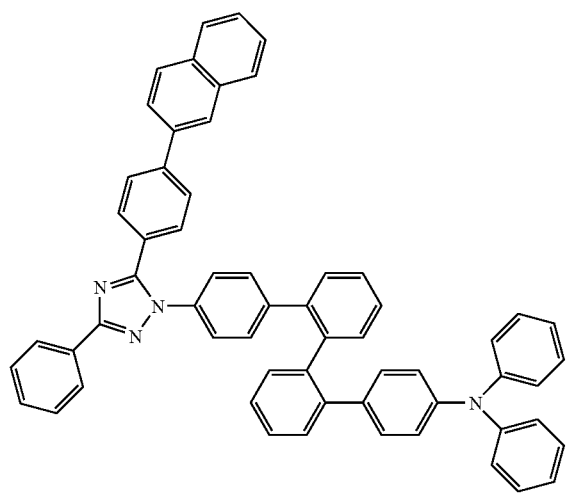
(139)
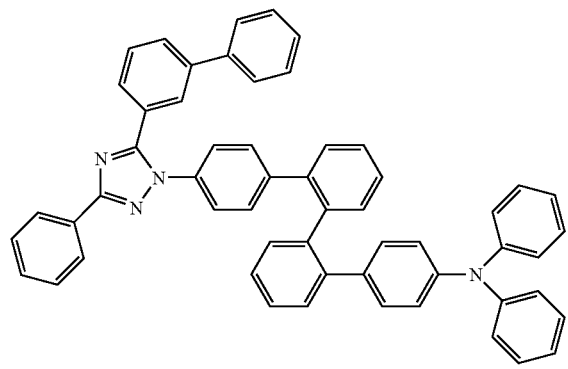
(140)
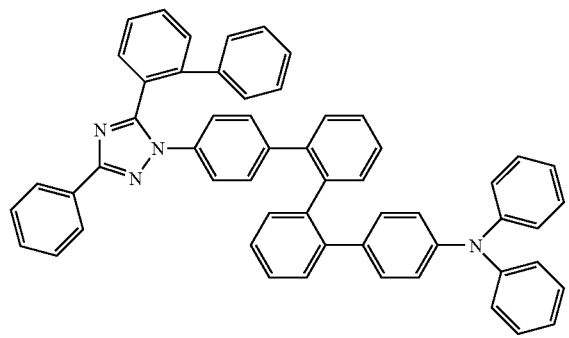

-continued
(141) (142)
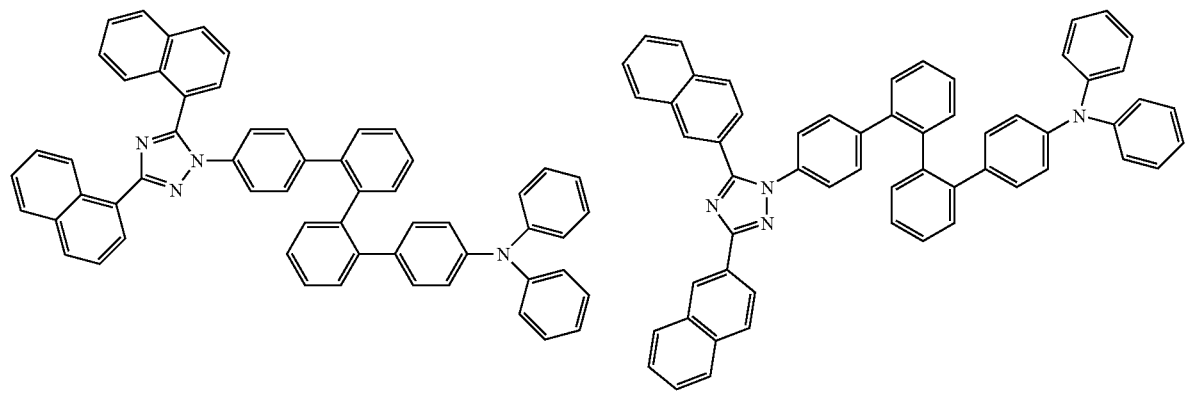
(143) (144)
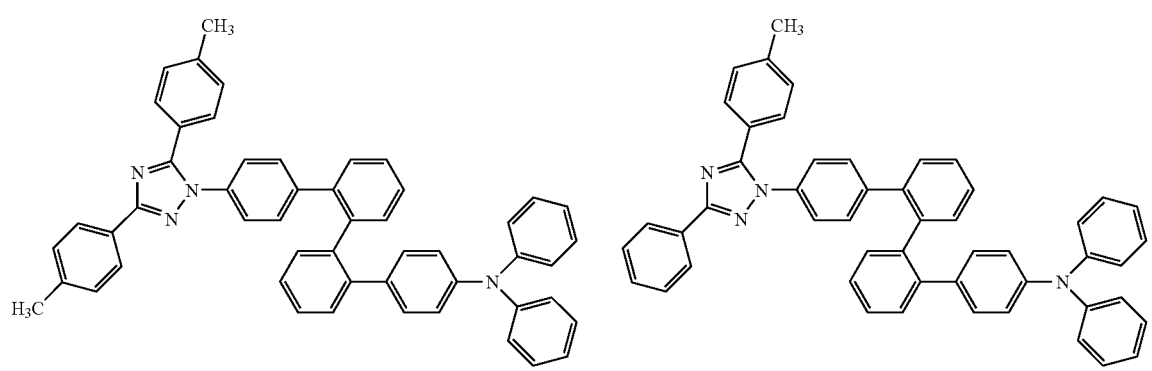
(145) (146)
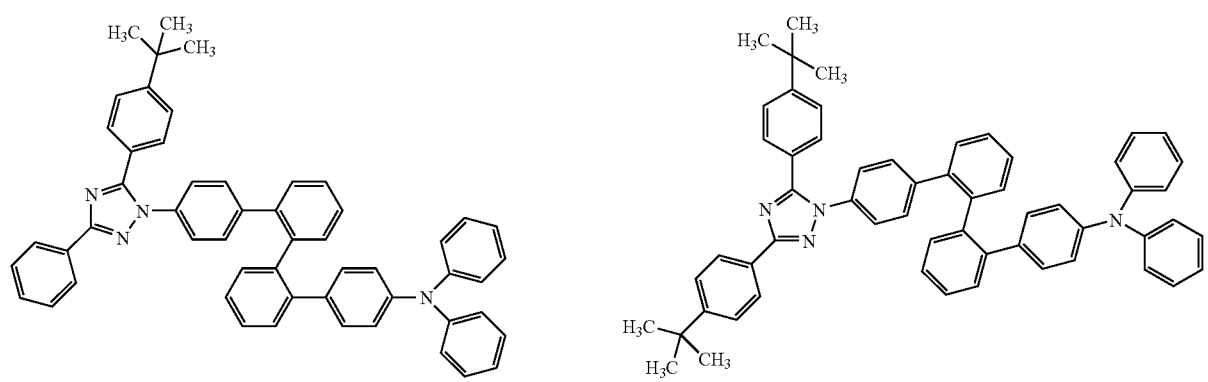

-continued
(147)
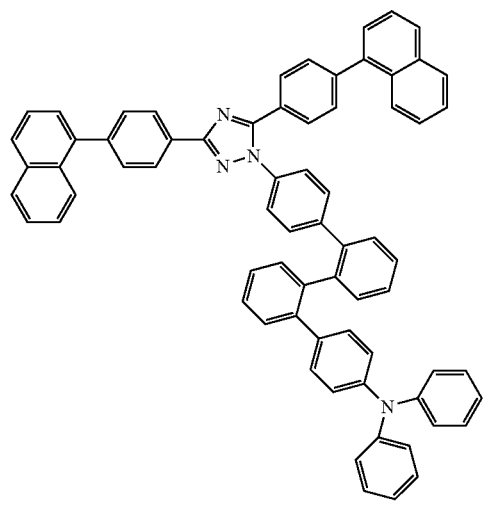
(148)
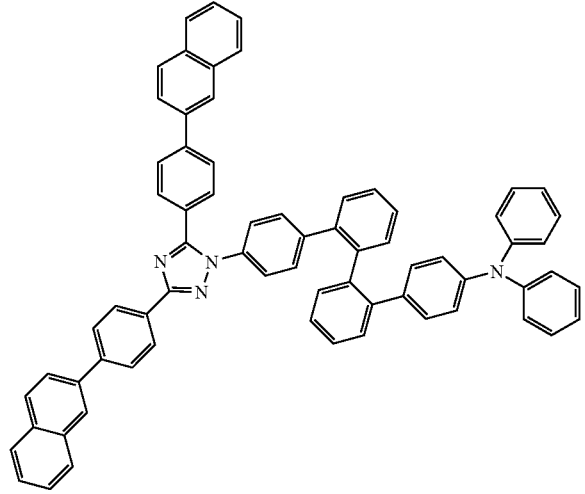
(149)
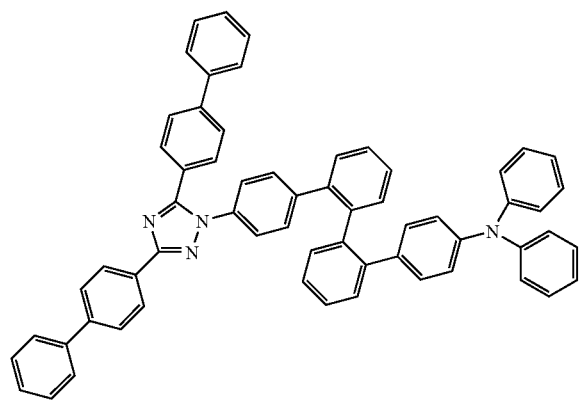
(150)
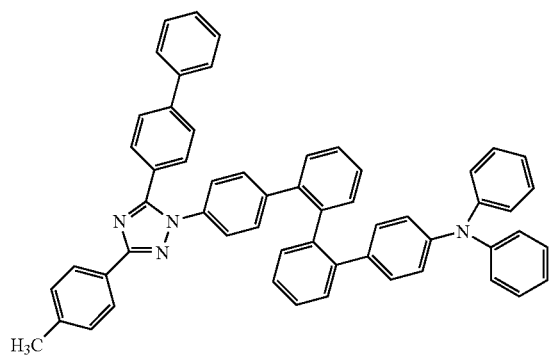
(151)
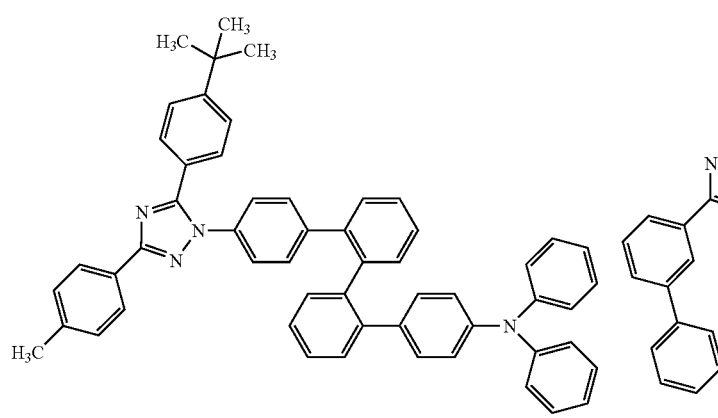
(152)
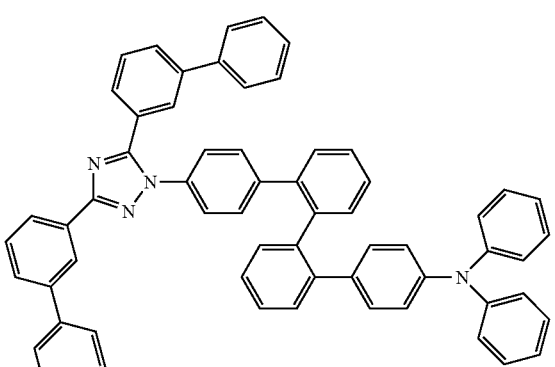

-continued
(153)
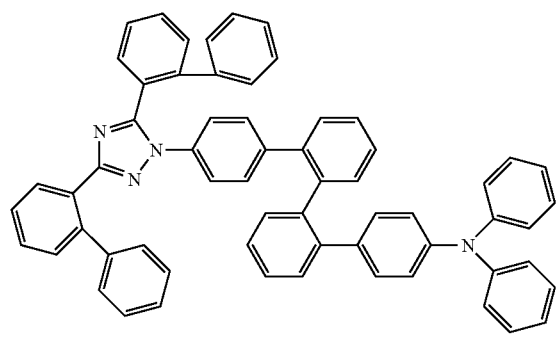
(154)
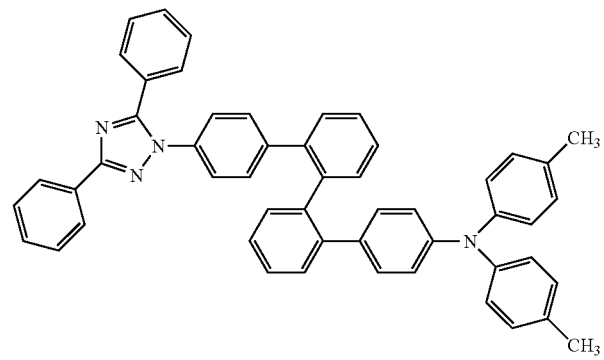
(155)
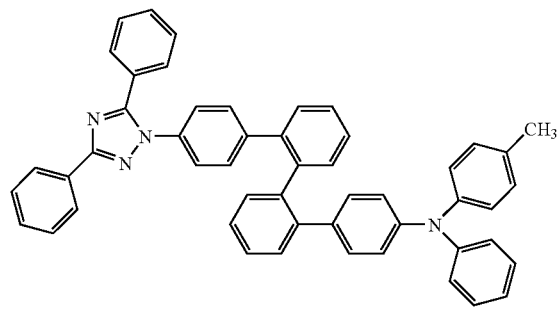
(156)
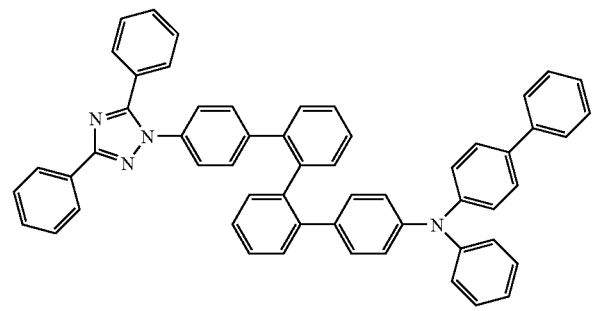
(157)
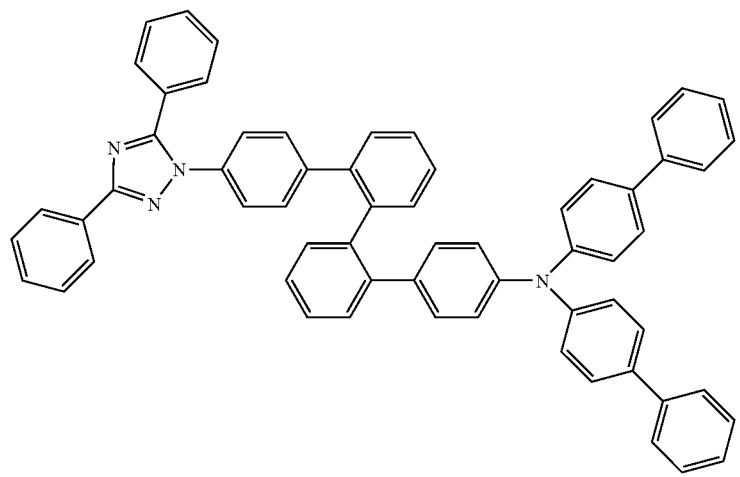
(158)
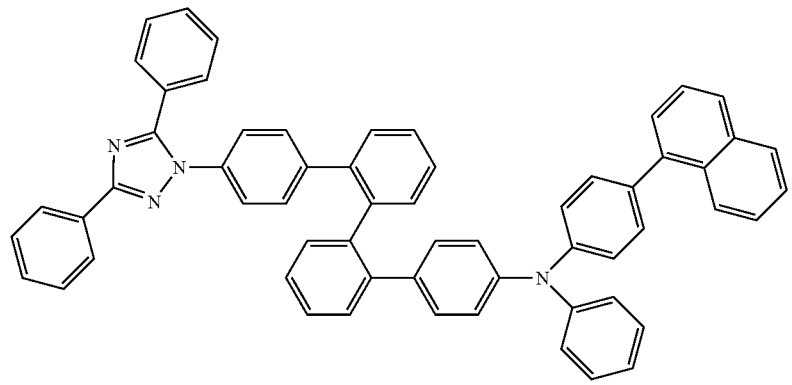

-continued
(159)
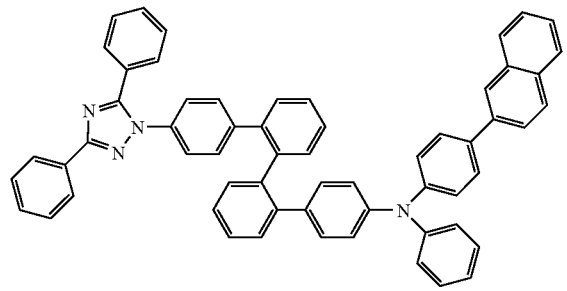
(160)
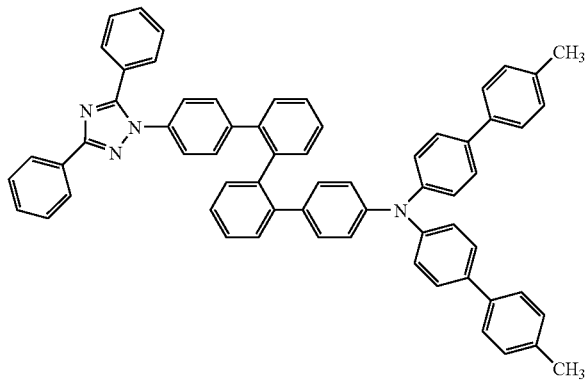
(161)
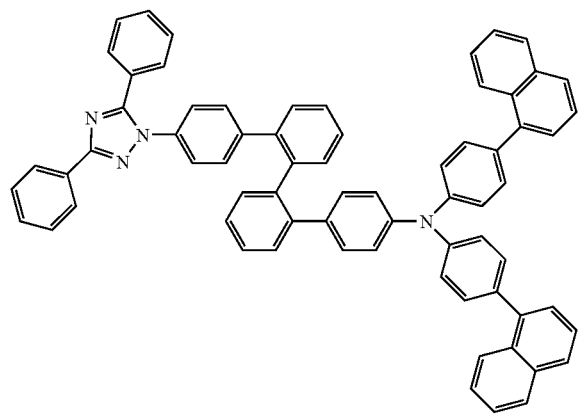
(162)
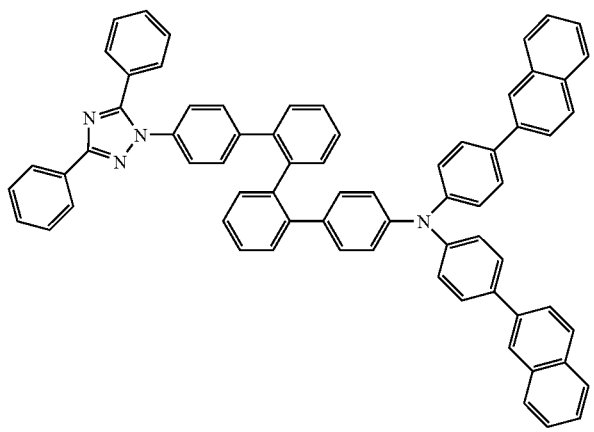
(163)
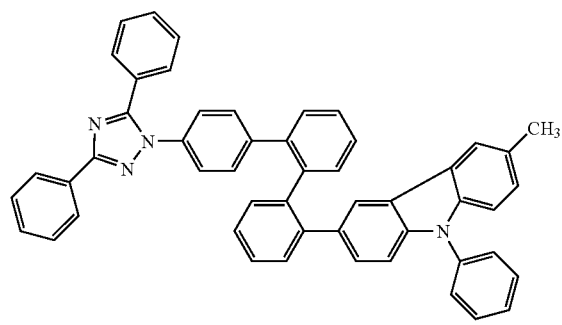
(164)
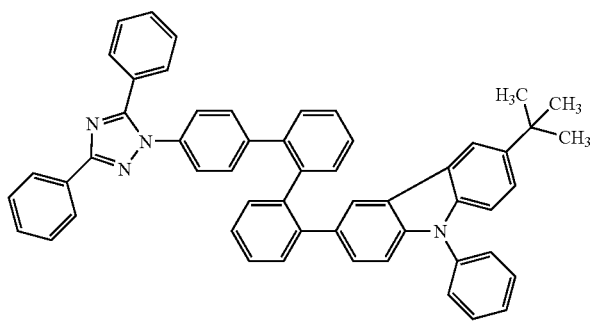
(165)
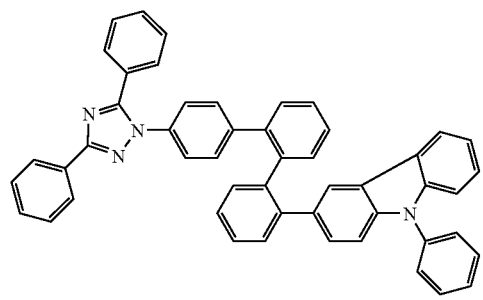
(166)
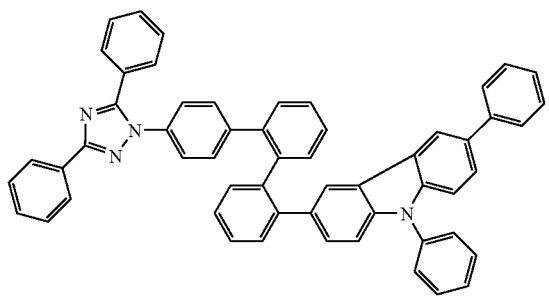

-continued
(167)
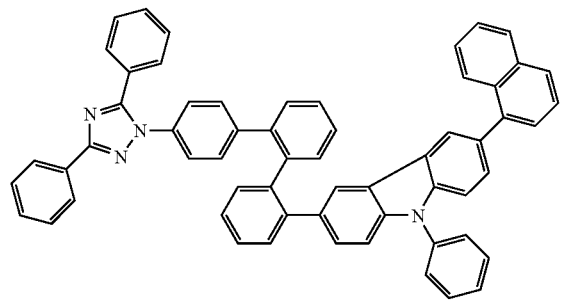
(168)
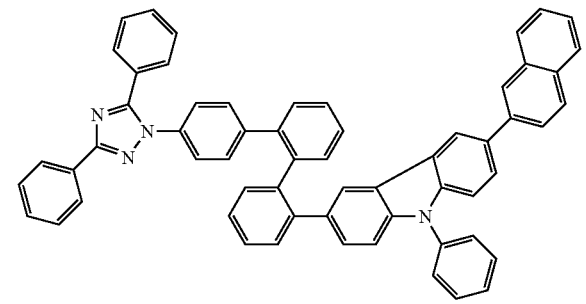
(169)
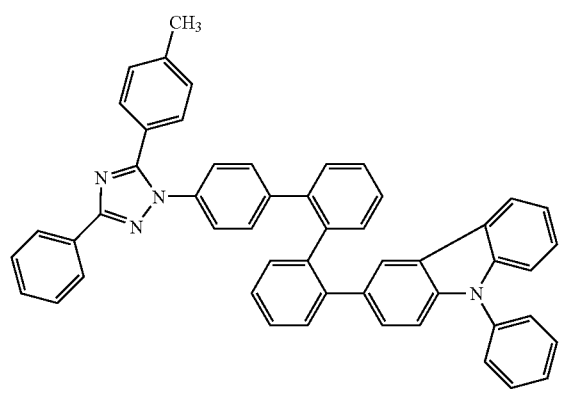
(170)
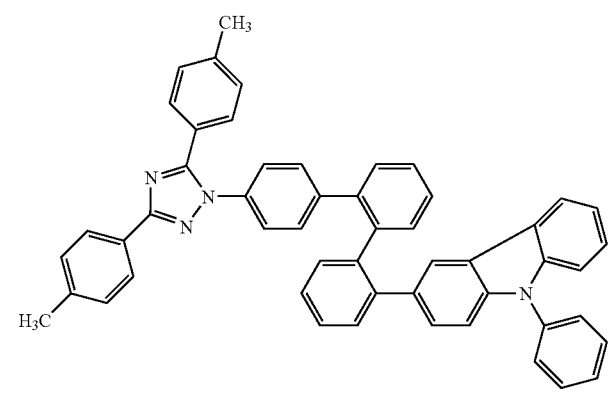
(171)
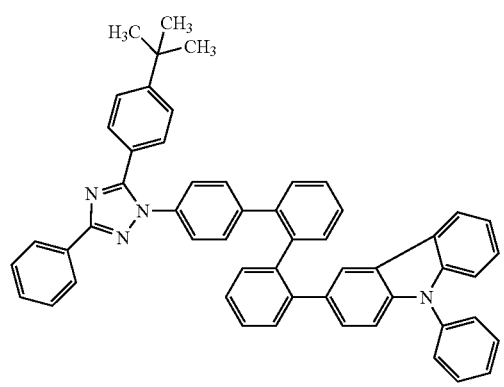
(172)
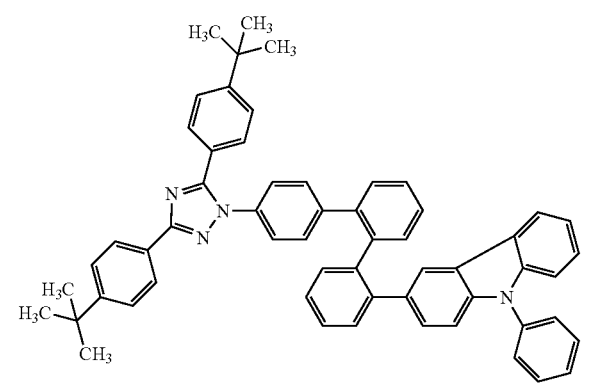
(173)
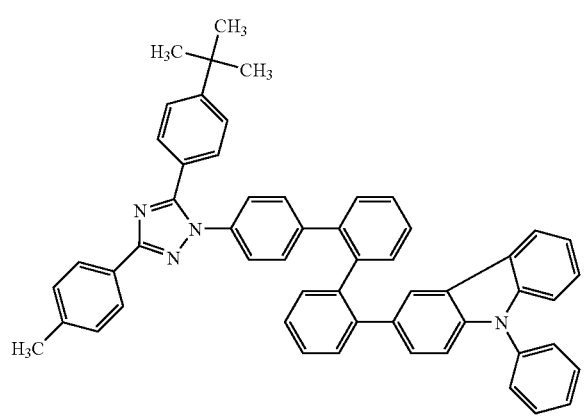
(174)
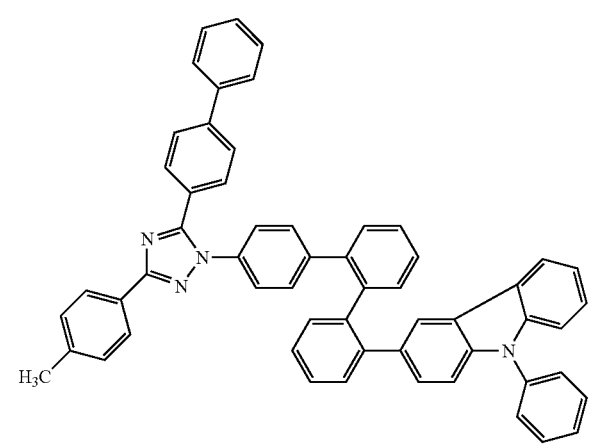

(175)
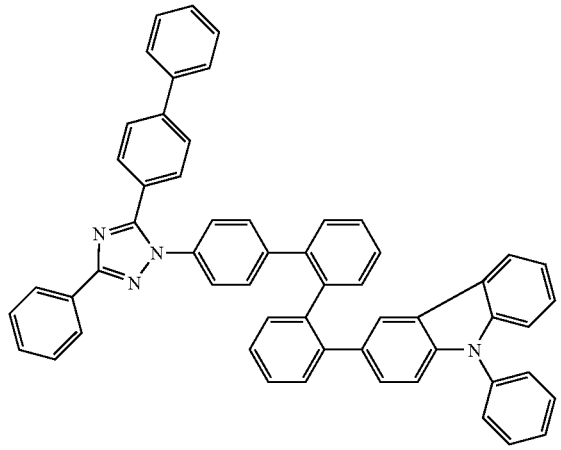
(176)
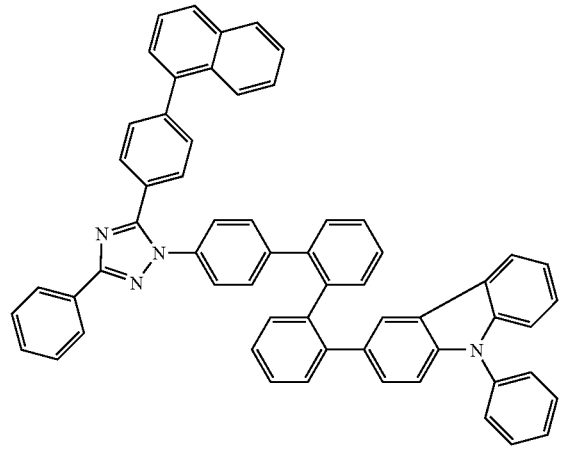
(177)
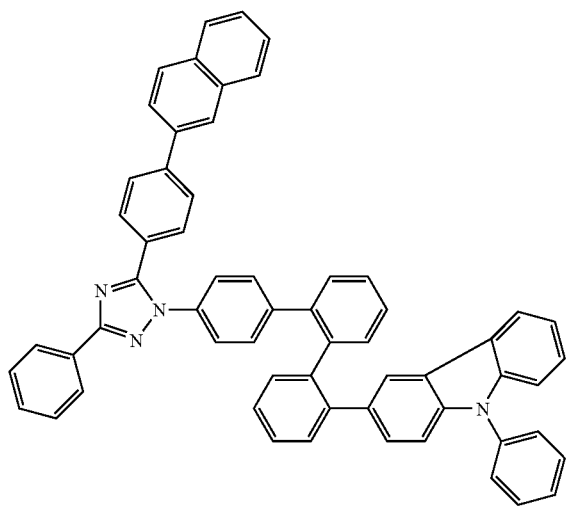
(178)
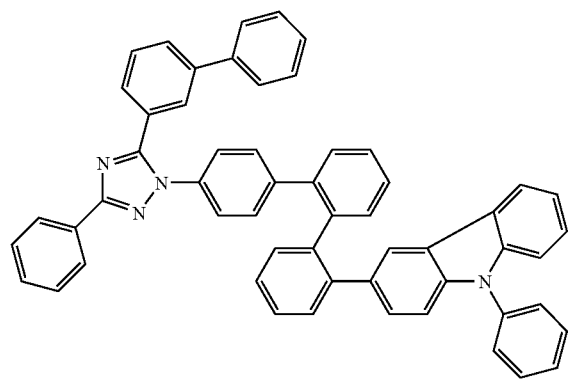
(179)
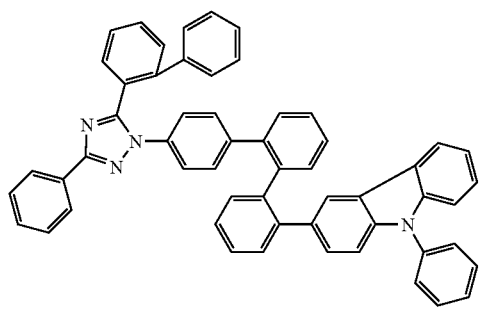
(180)
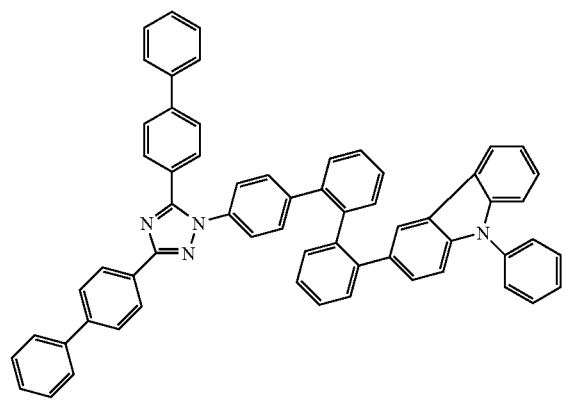

(181)
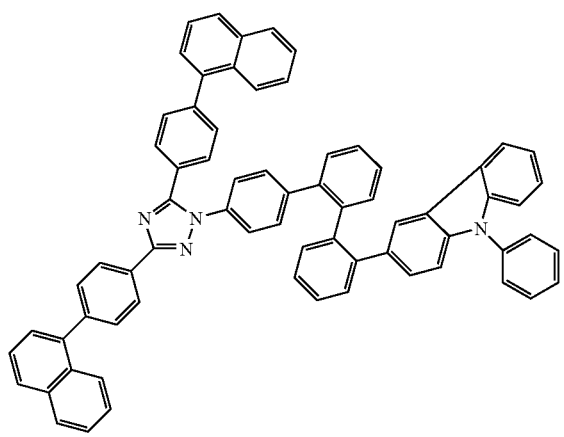
(182)
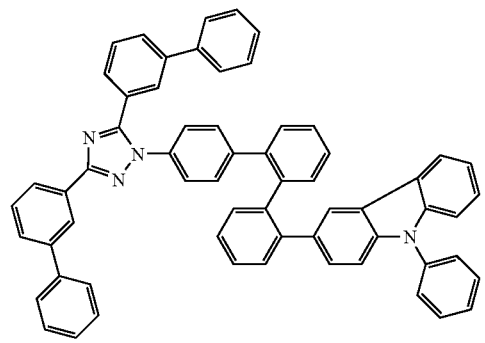
(183)
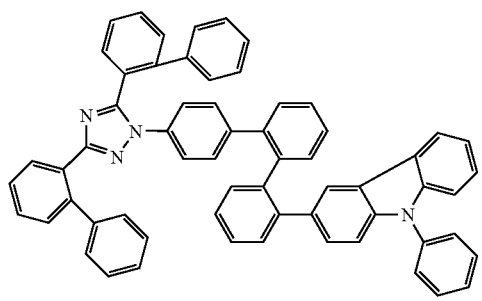
(184)
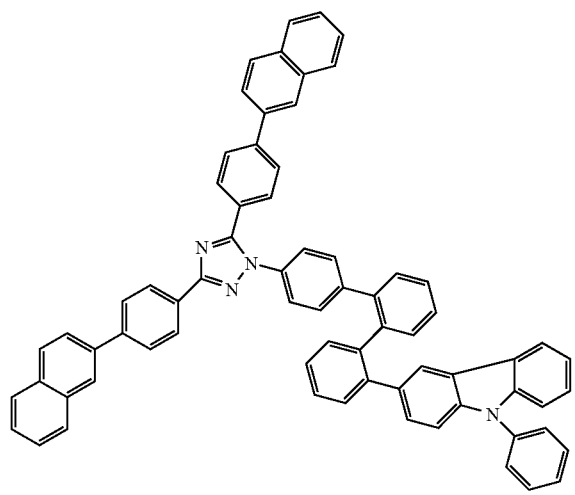
(185)
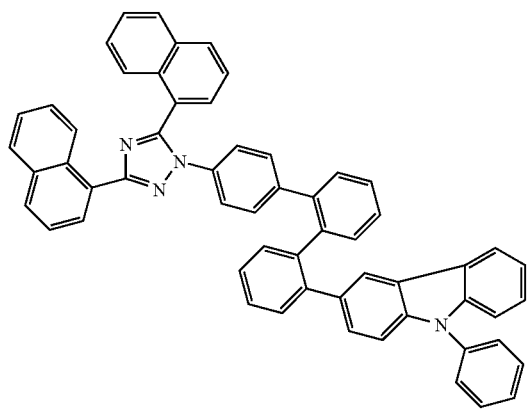
(186)
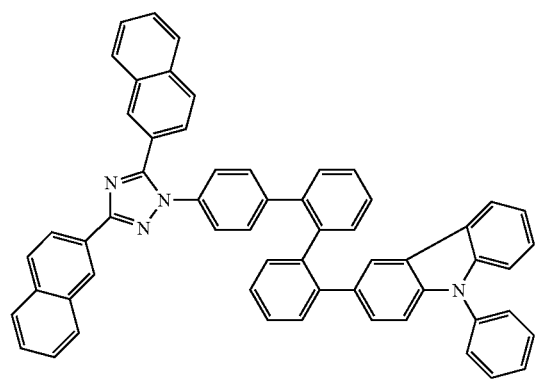

-continued
(187)
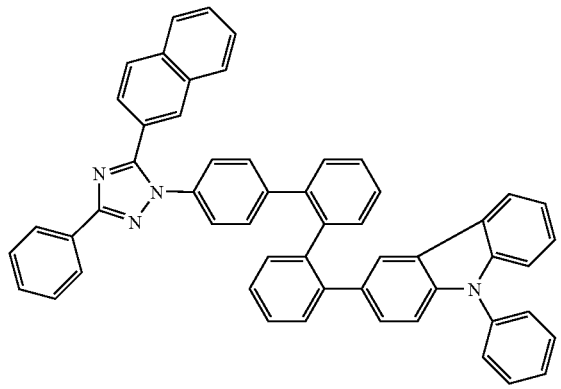
(188)
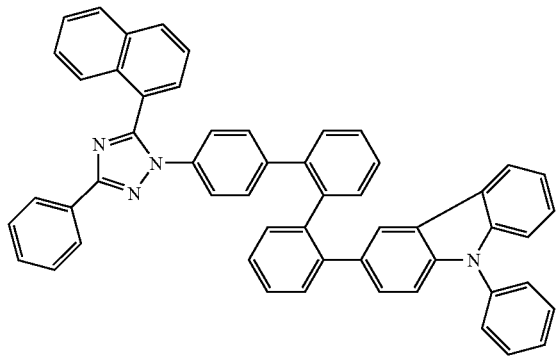
(189)
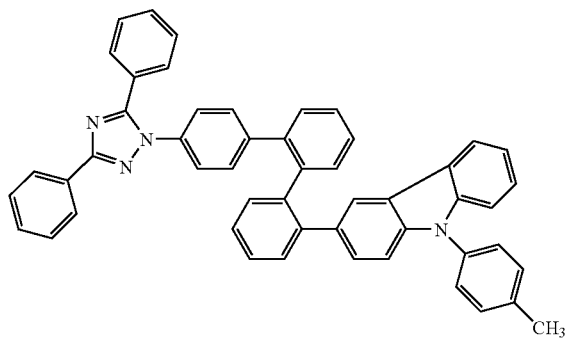
(190)
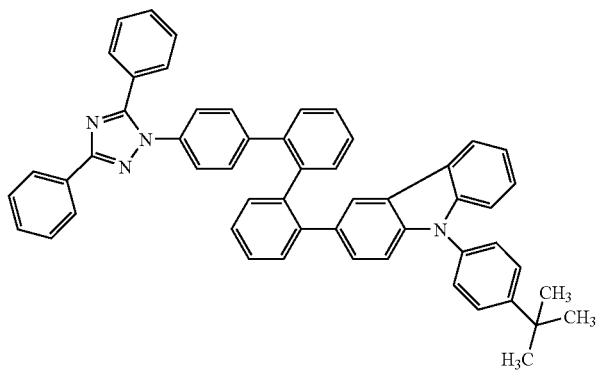
(191)
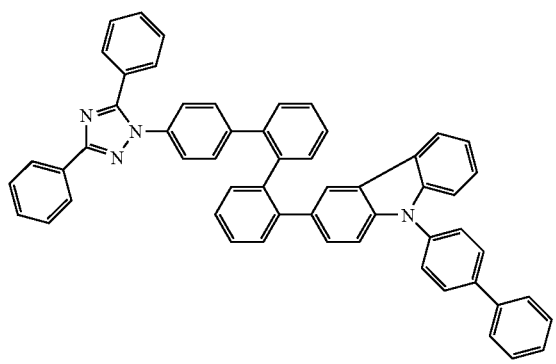
(192)
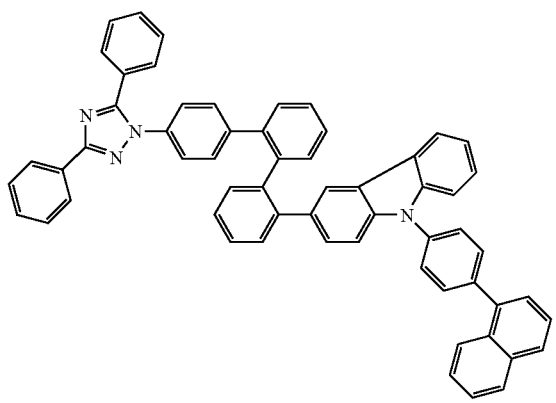
(193)
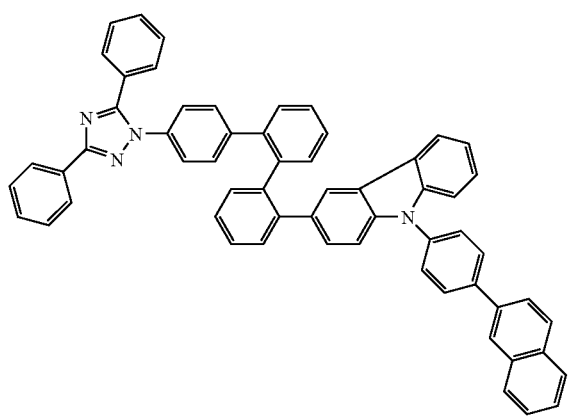
(194)
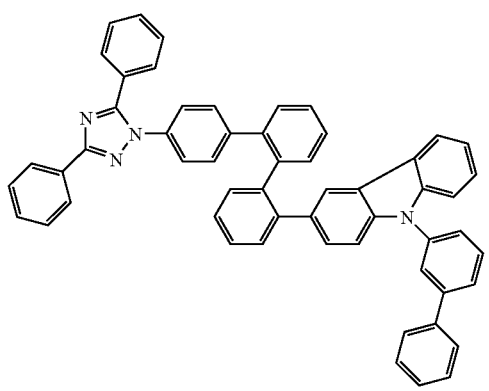

-continued
(195)
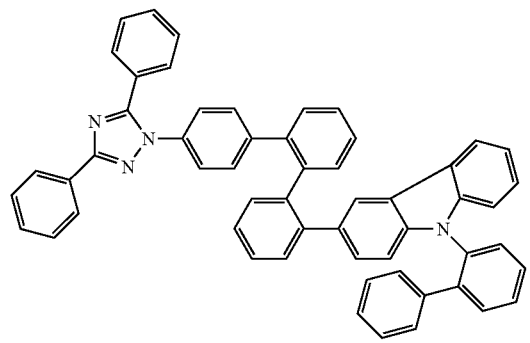
(196)
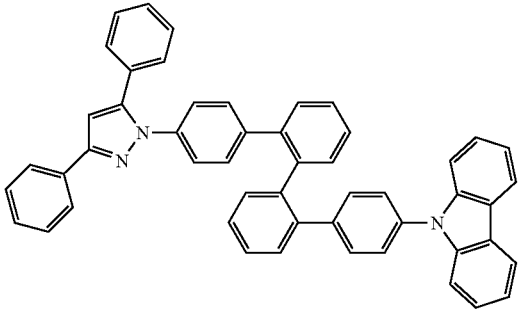
(197)
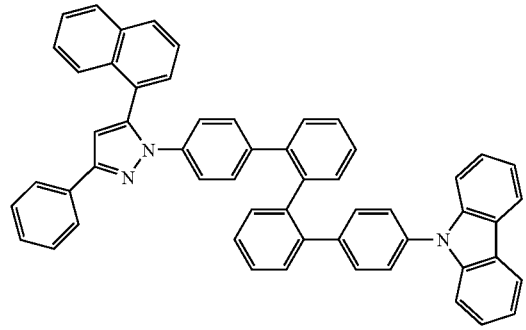
(198)
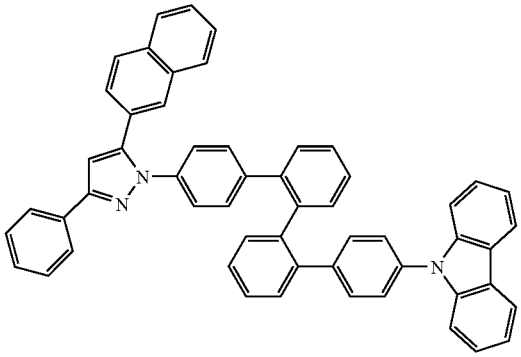
(199)
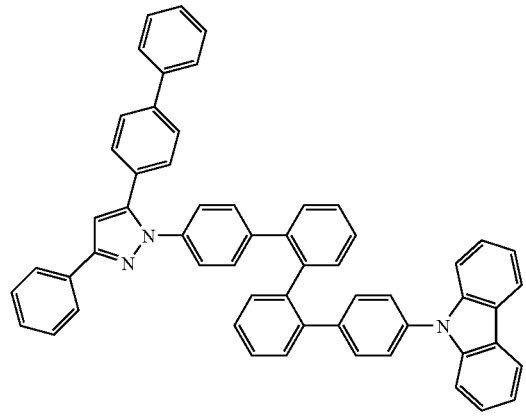
(200)
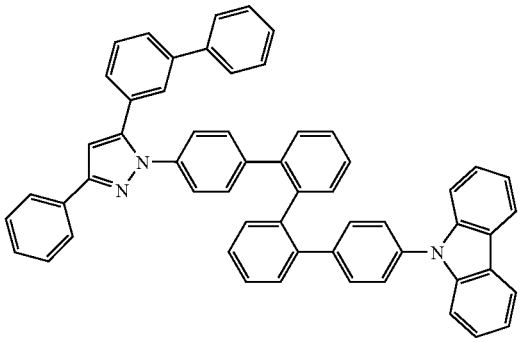
(201)
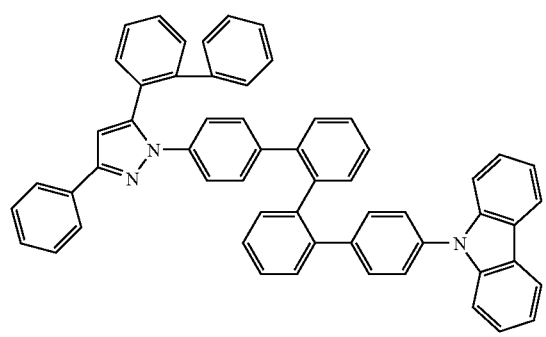
(202)
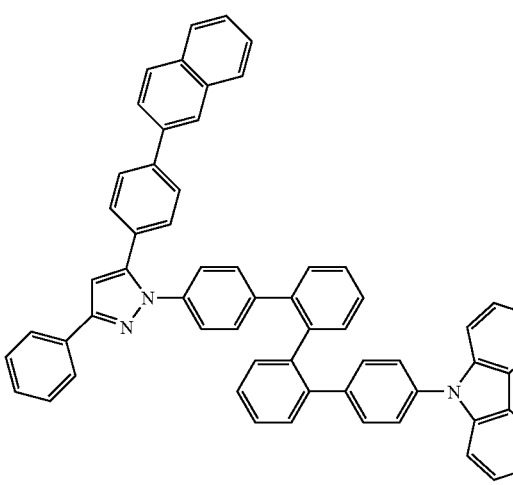

-continued
(203)
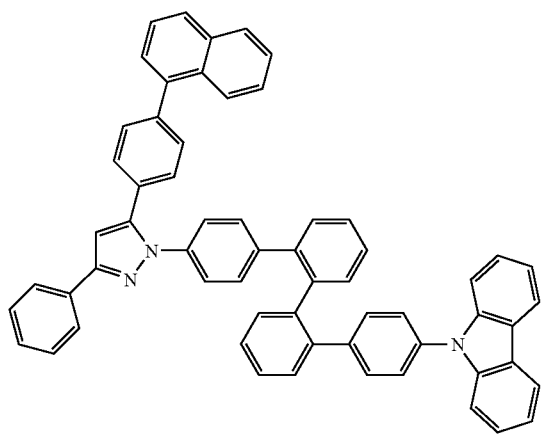
(204)
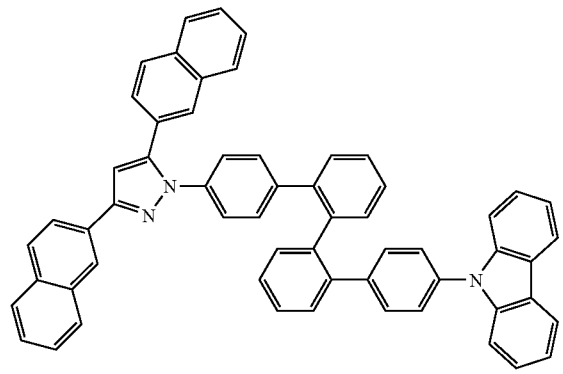
(205)
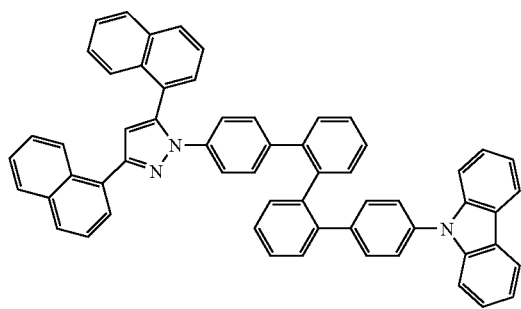
(206)
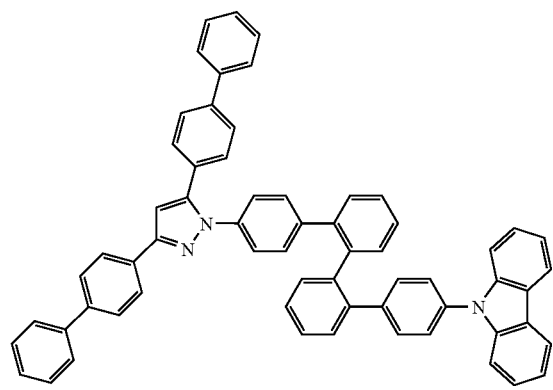
(207)
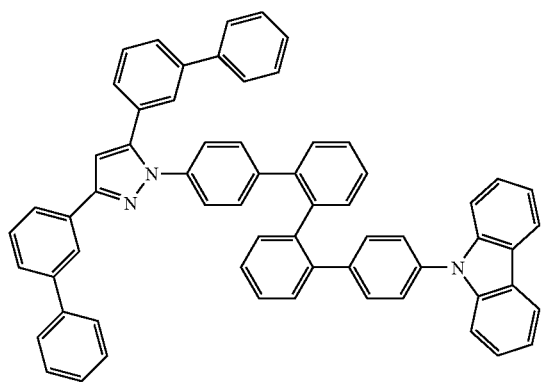
(208)
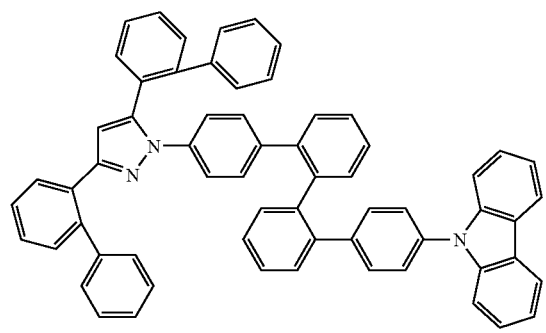

-continued
(209)
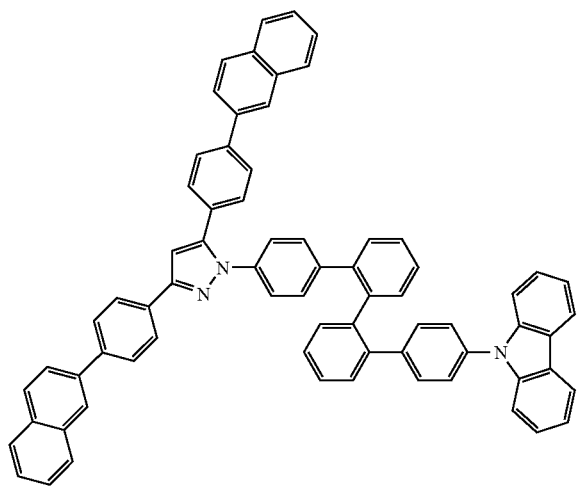
(210)
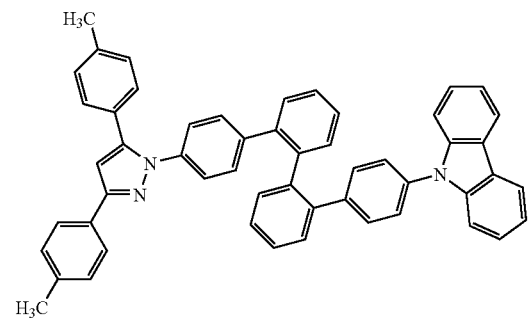
(211)
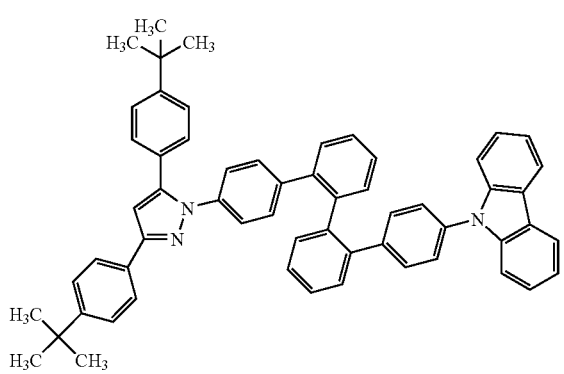
(212)
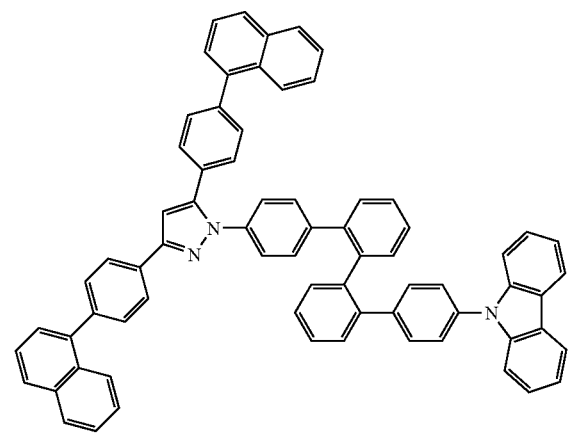
(213)
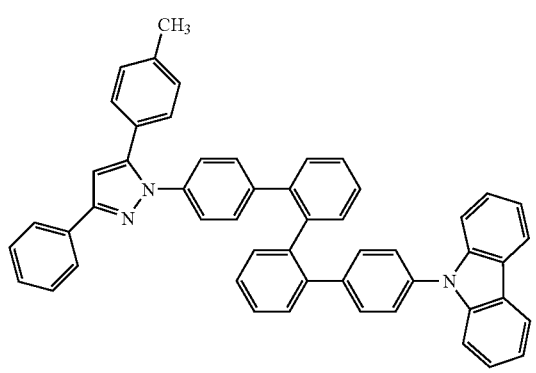
(214)
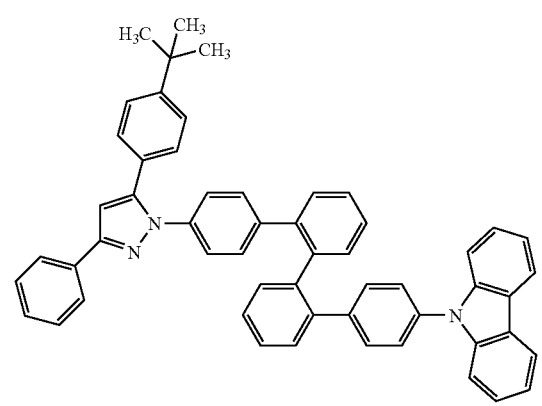

-continued
(215)
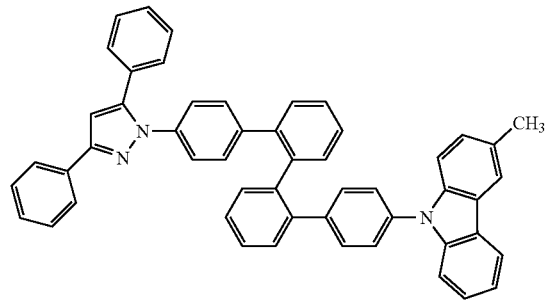
(216)
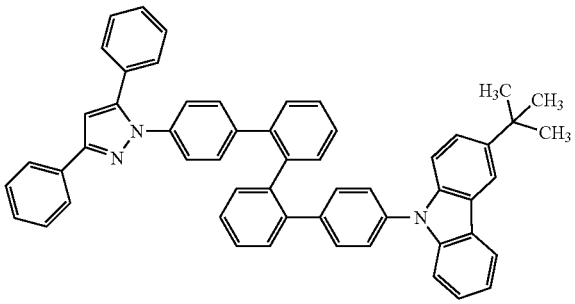
(217)
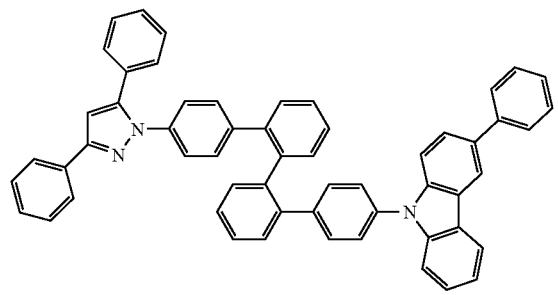
(218)
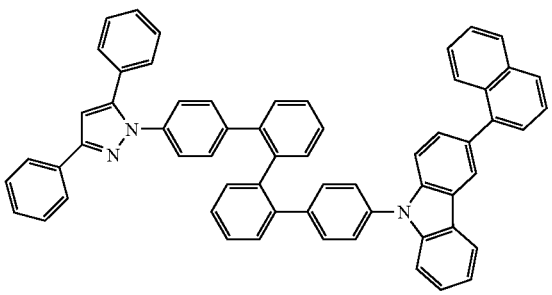
(219)
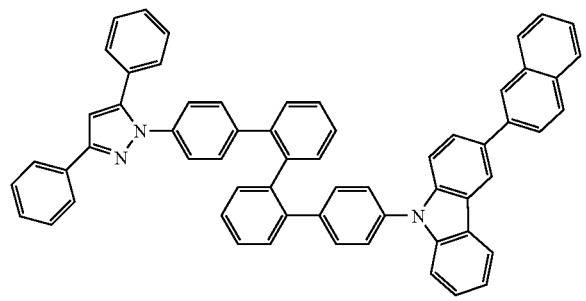
(220)
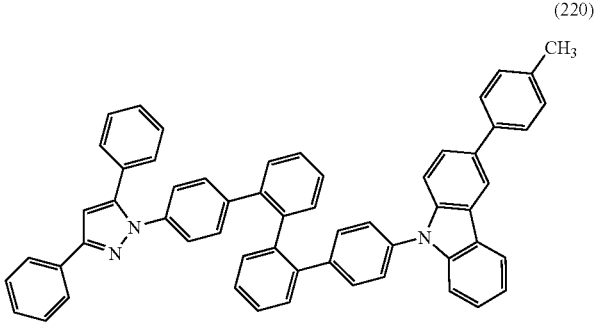
(221)
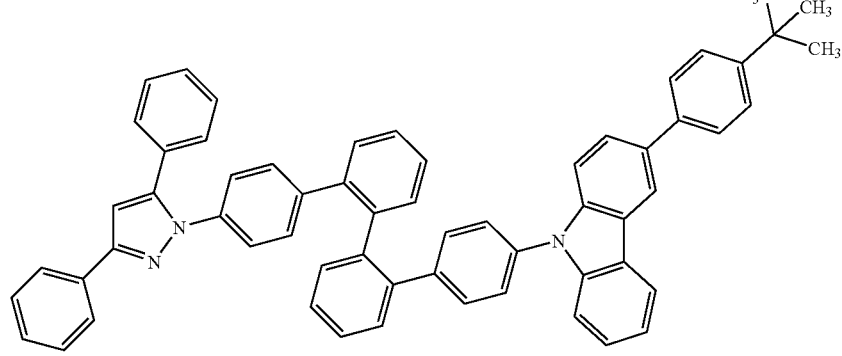

(222)
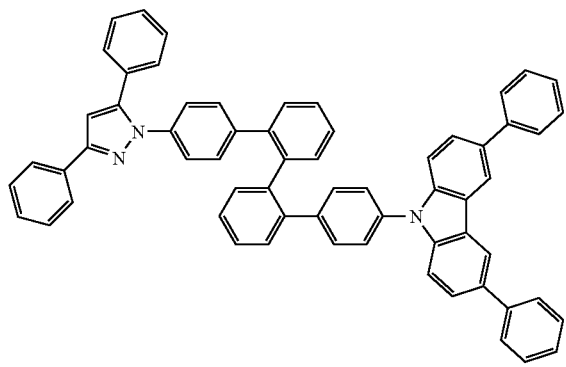
(223)
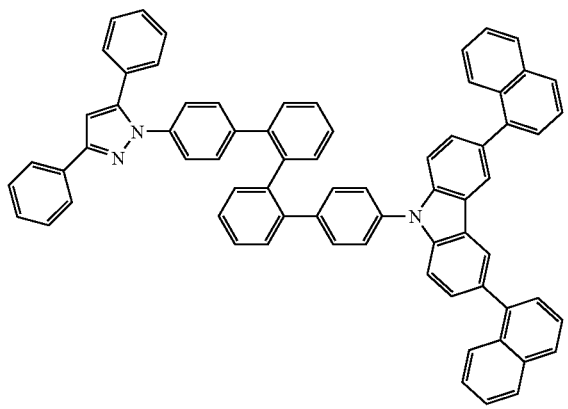
(224)
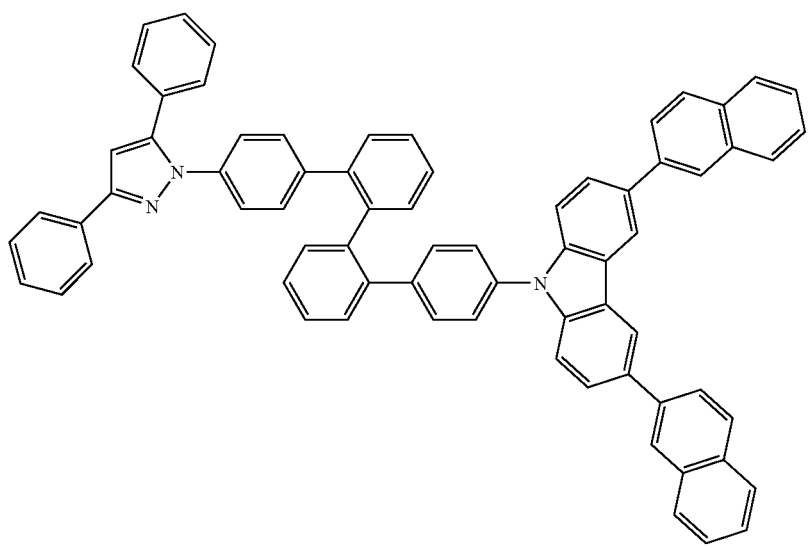
(225)
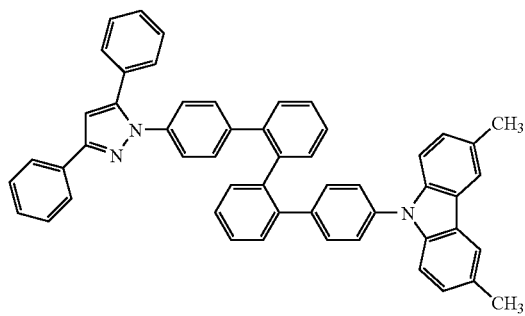
(226)
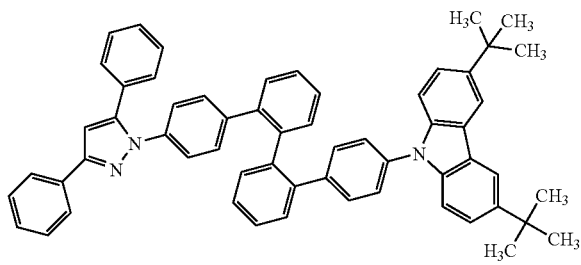

-continued
(227)
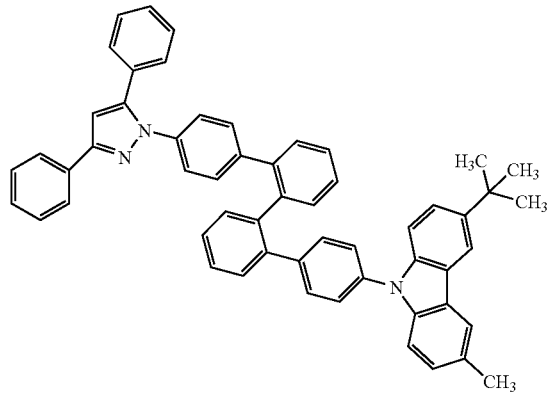
(228)
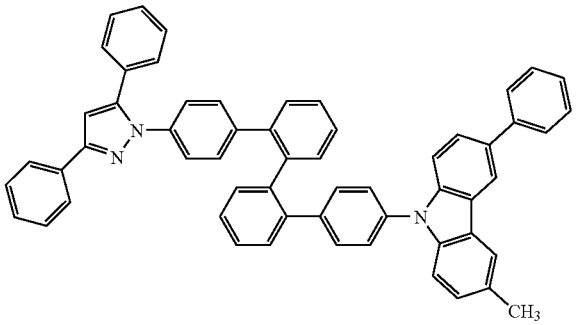
(229)
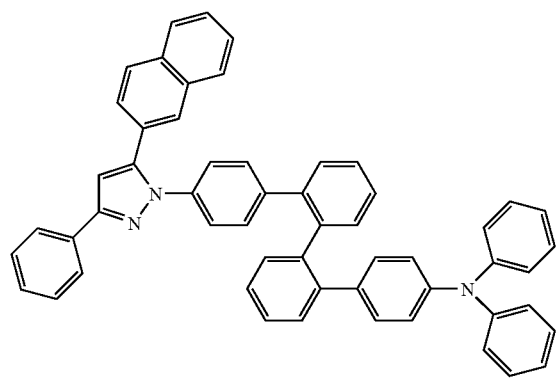
(230)
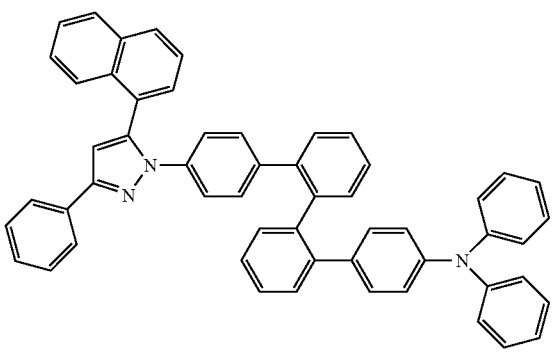
(231)
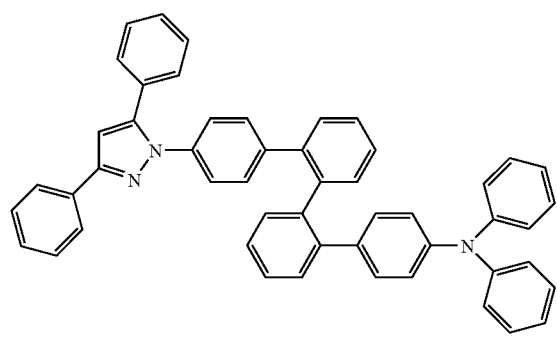
(232)
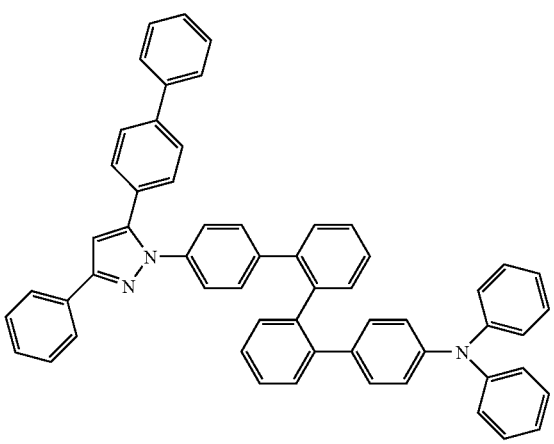

-continued
(233)
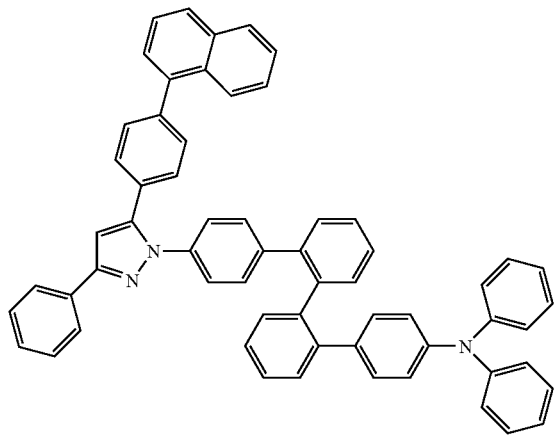
(234)
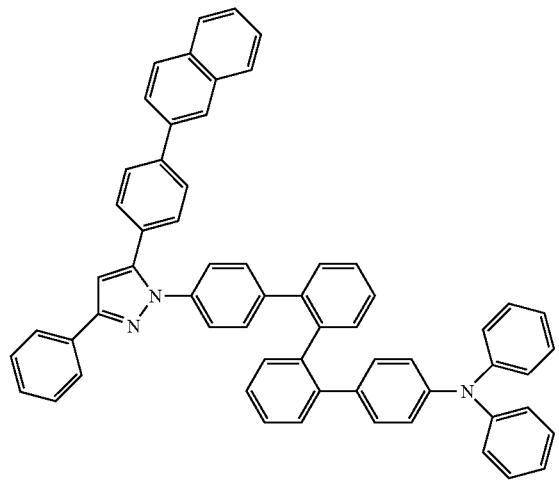
(235)
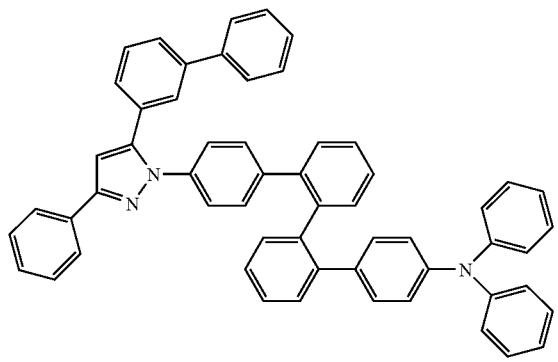
(236)
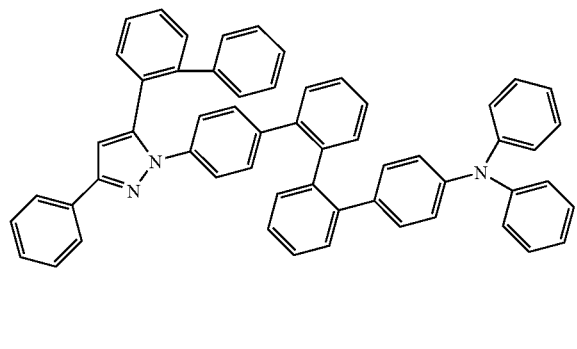
(237)
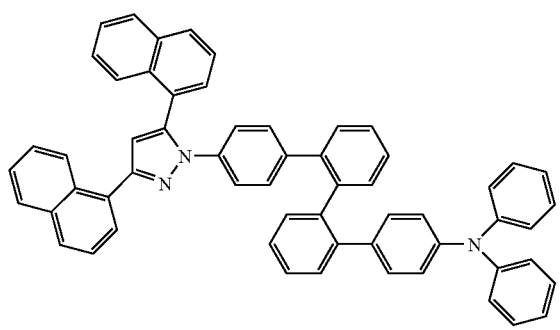
(238)
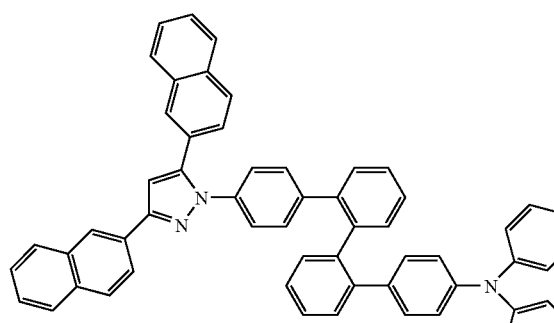
(239)
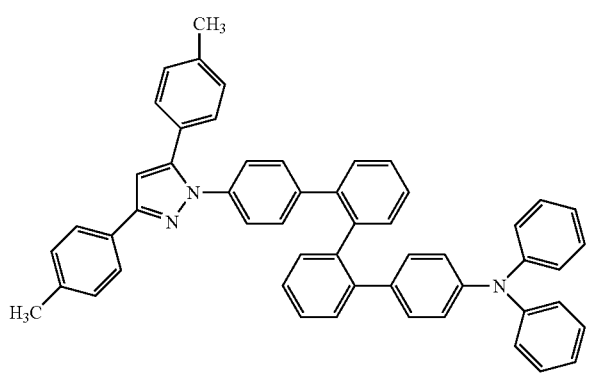
(240)
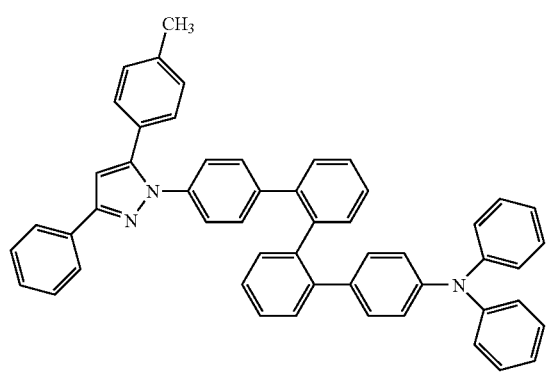

-continued
(241)
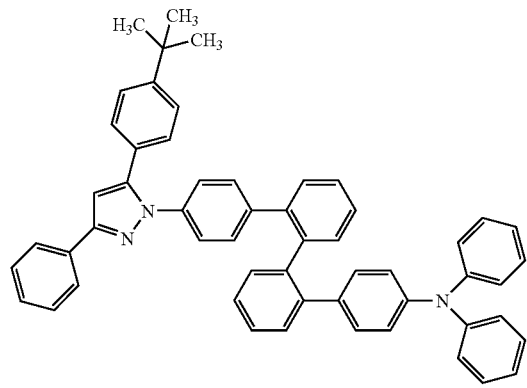
(242)
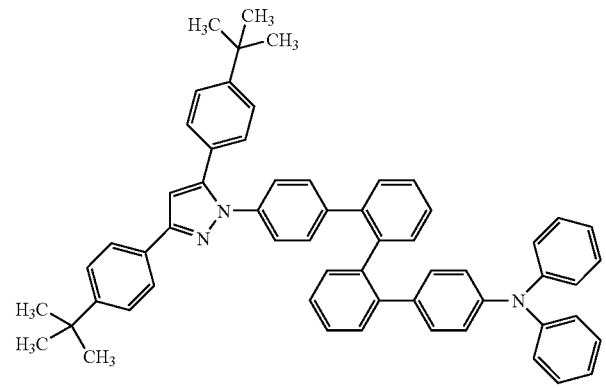
(243)
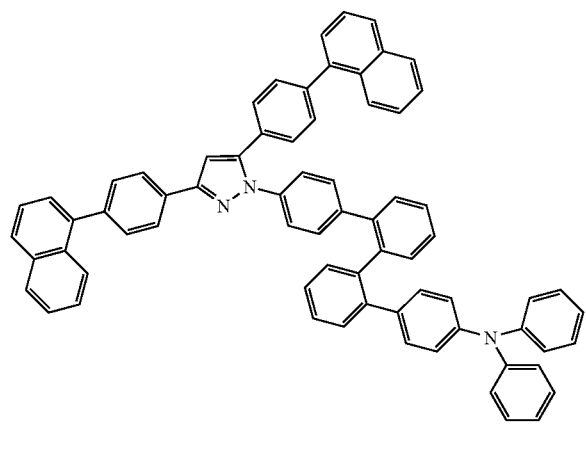
(244)
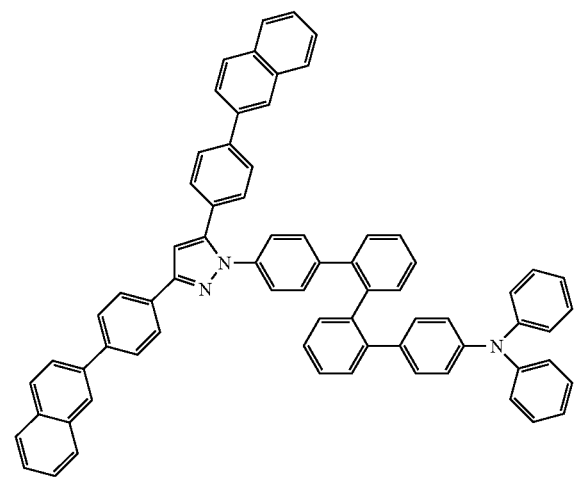
(245)
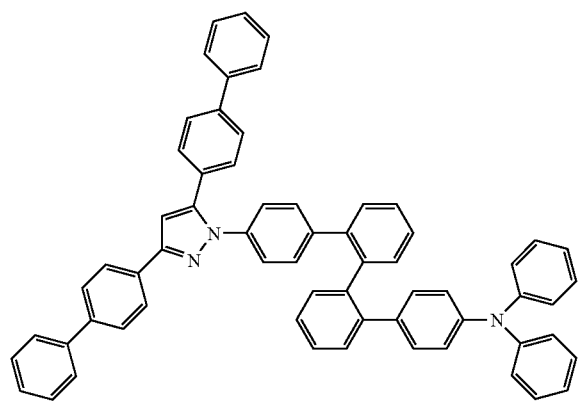
(246)
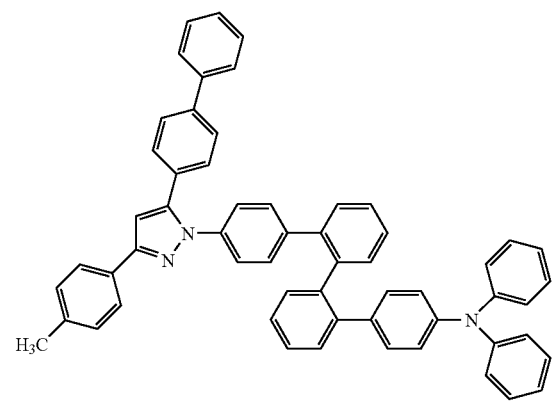

-continued
(247)
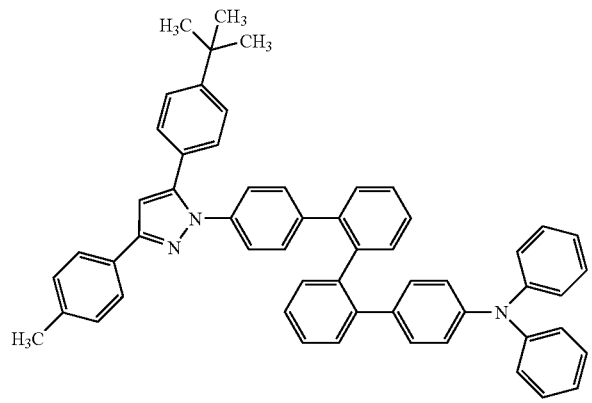
(248)
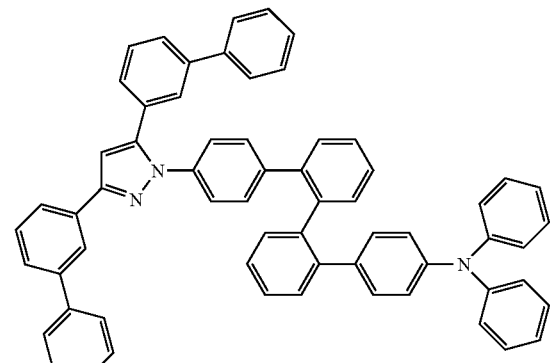
(249)
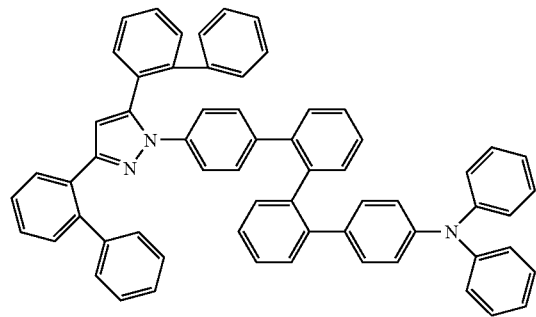
(250)
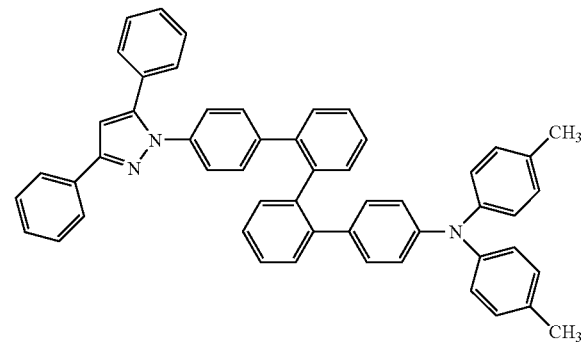
(251)
(252)
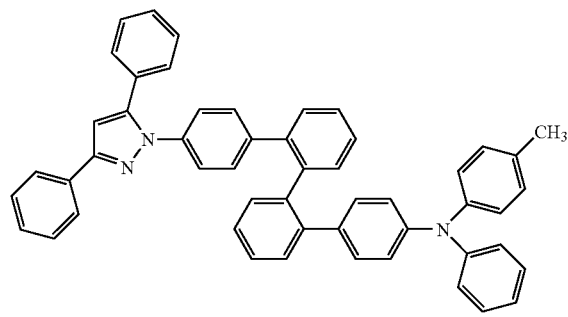
(253)
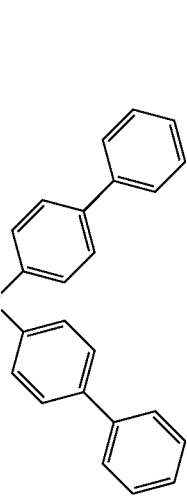

(254)
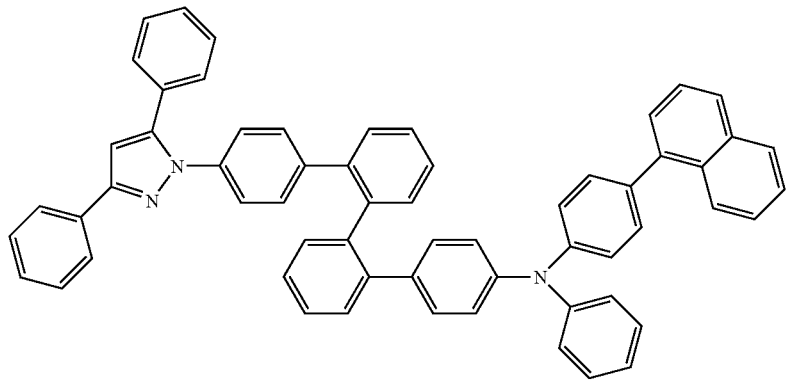
(255)
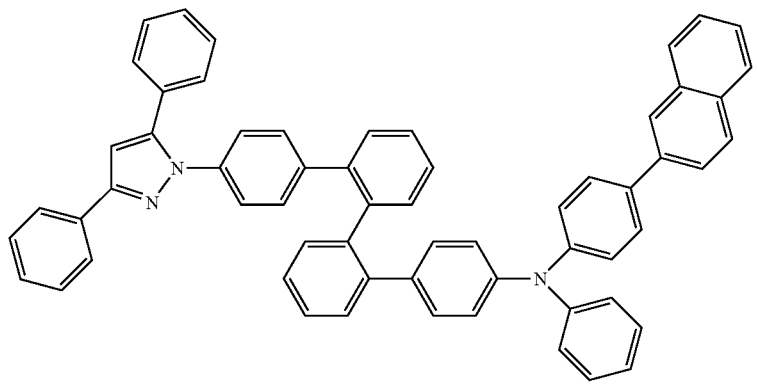
(256)
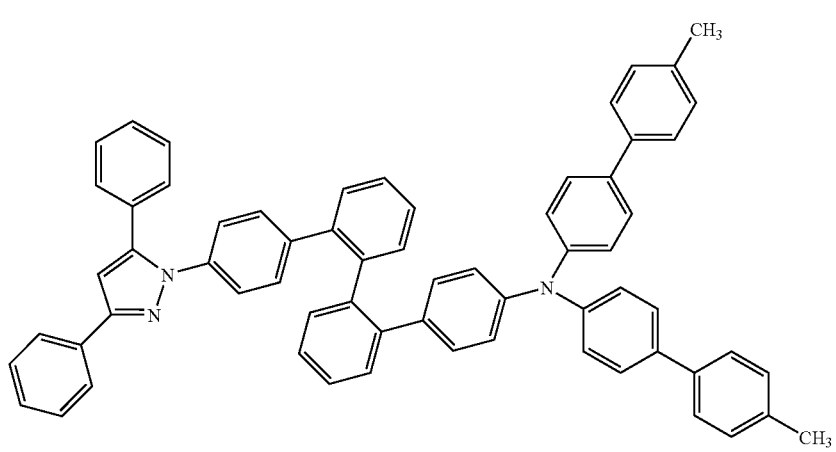
(257)
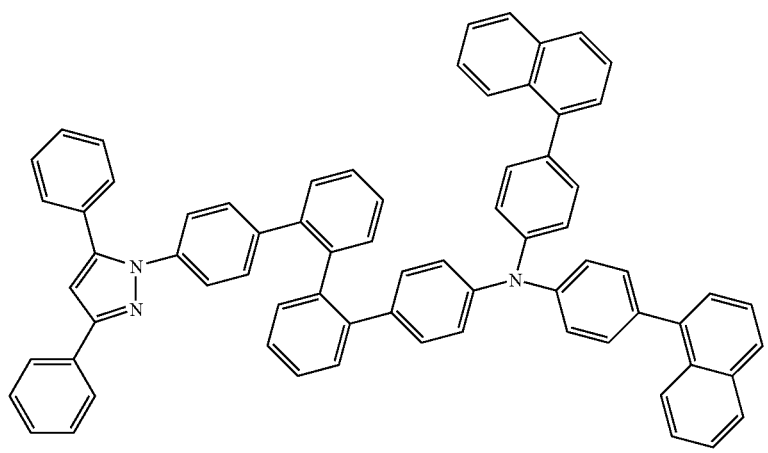

-continued
(258)
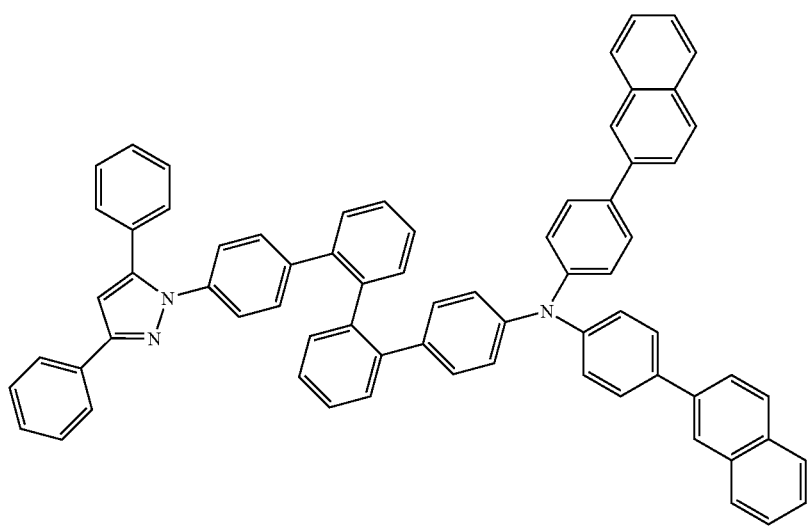
(259)
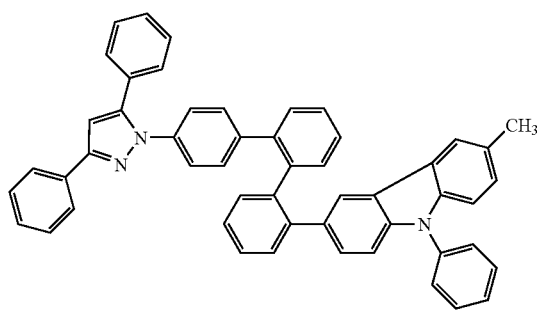
(260)
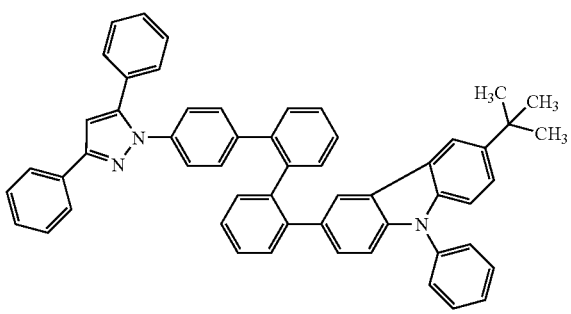
(261)
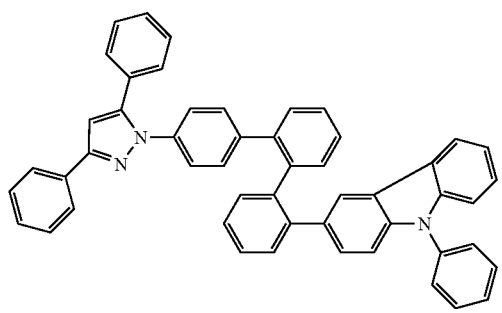
(262)
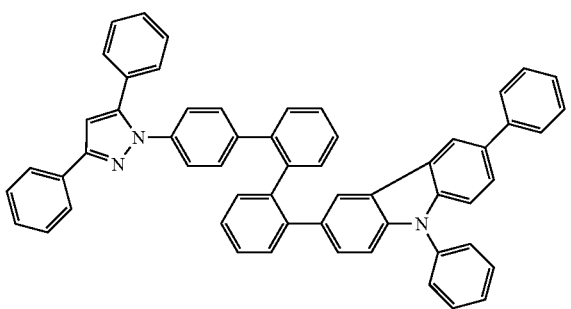
(263)
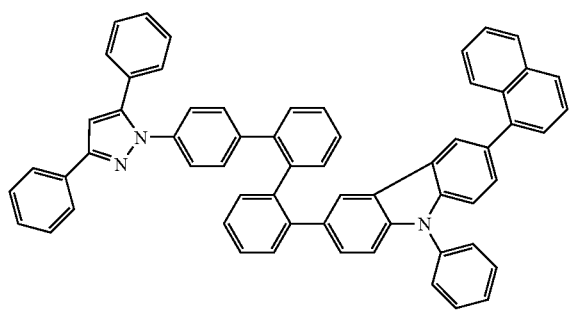
(264)
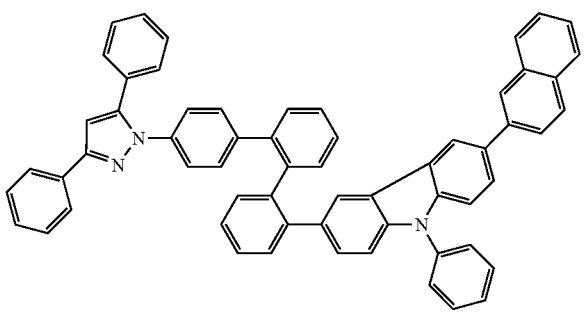

(265) 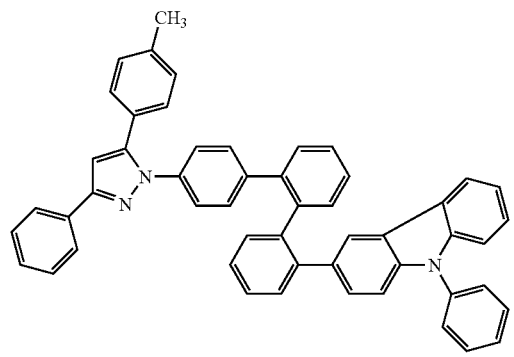
(266) 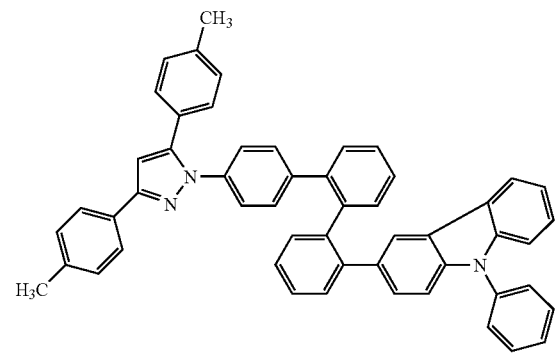
(267) 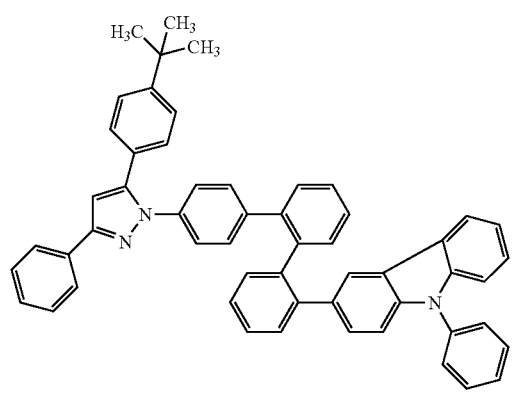
(268) 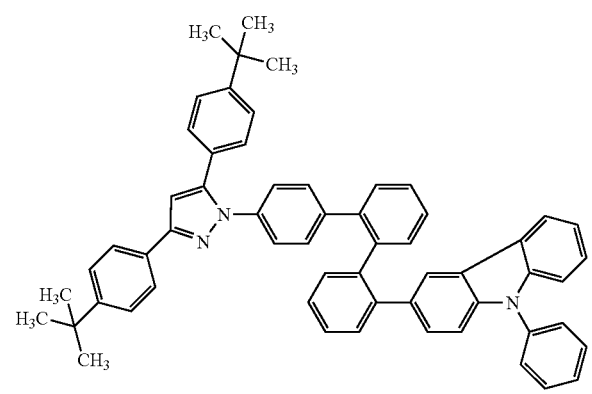
(269) 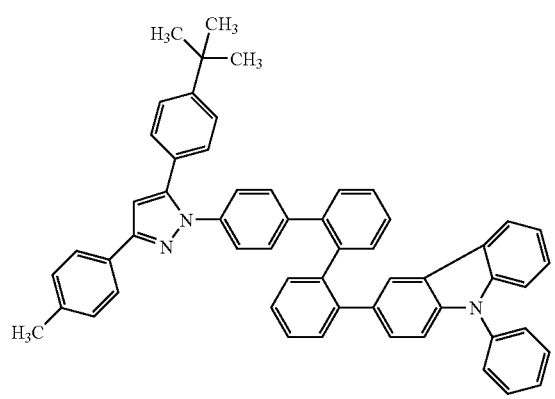
(270) 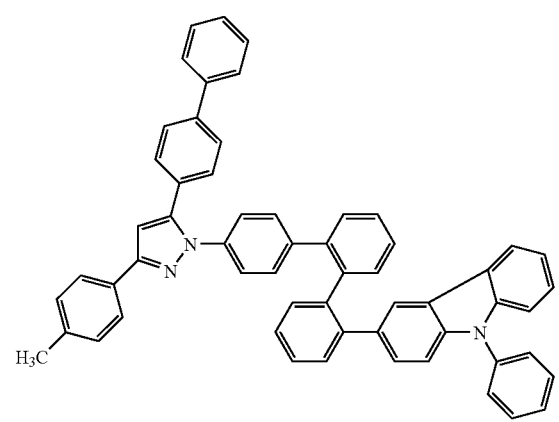

-continued
(271)
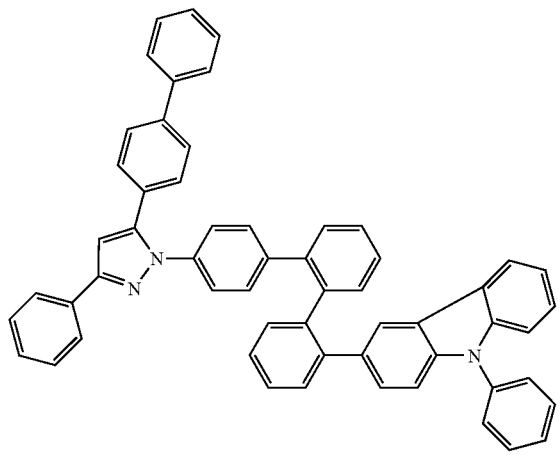
(272)
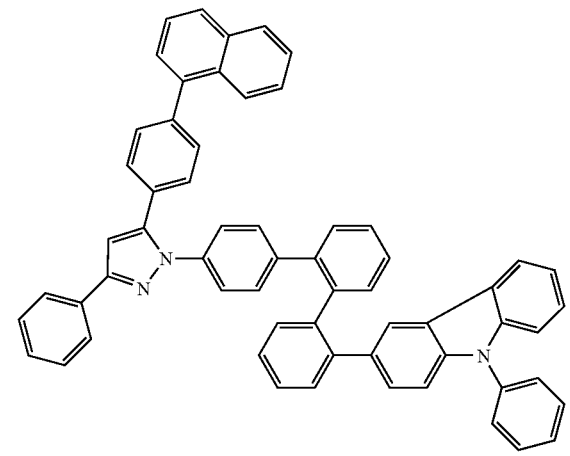
(273)
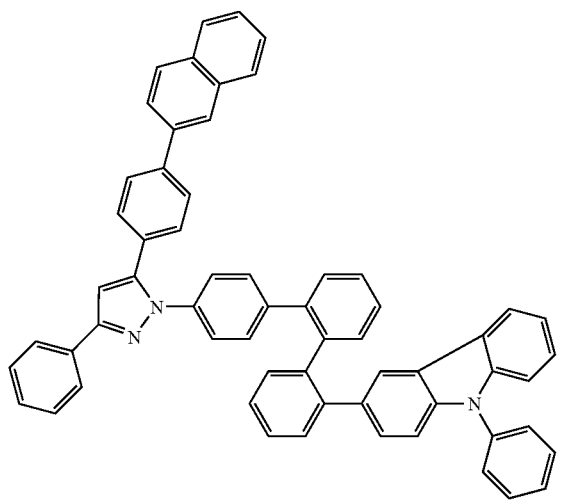
(274)
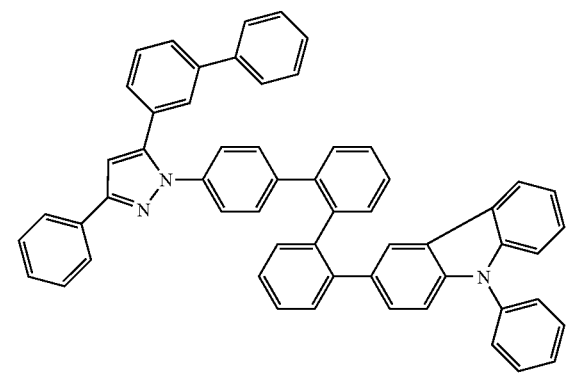
(275)
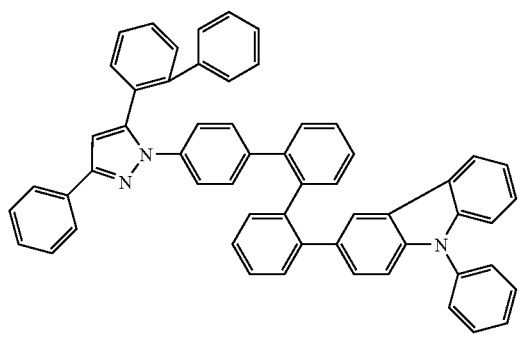
(276)
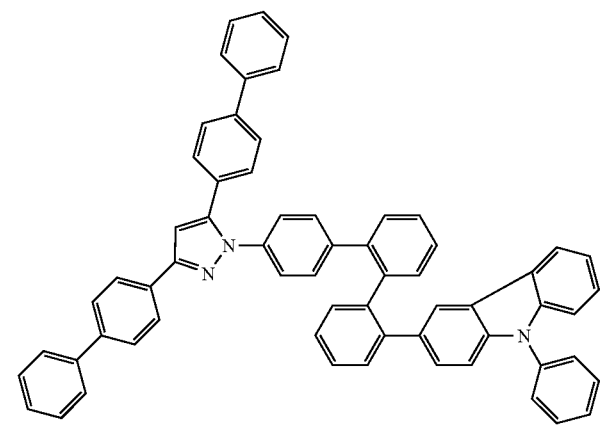

-continued
(277)
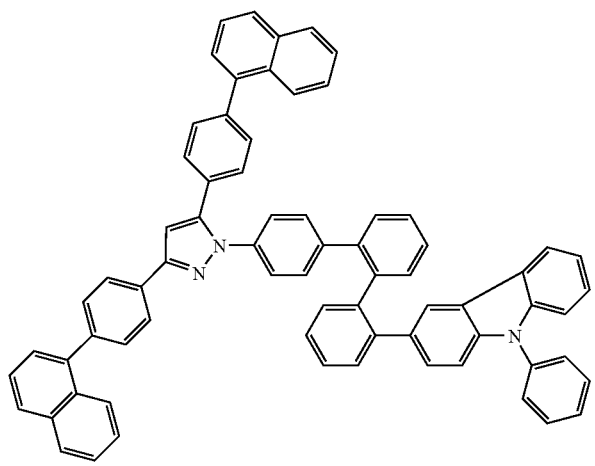
(278)
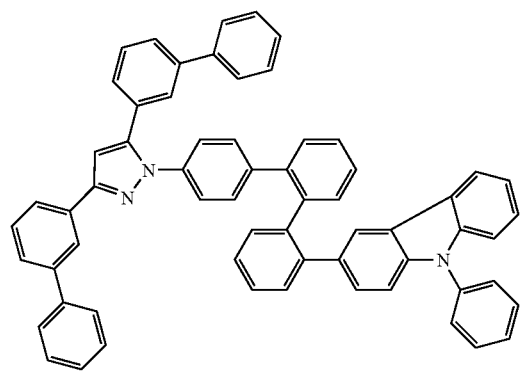
(279)
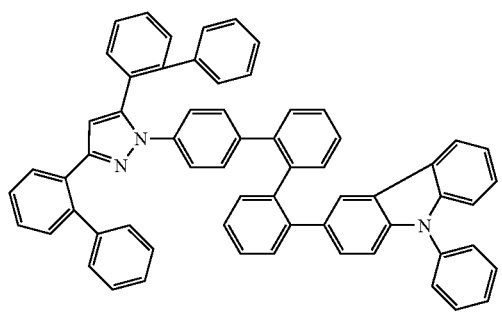
(280)
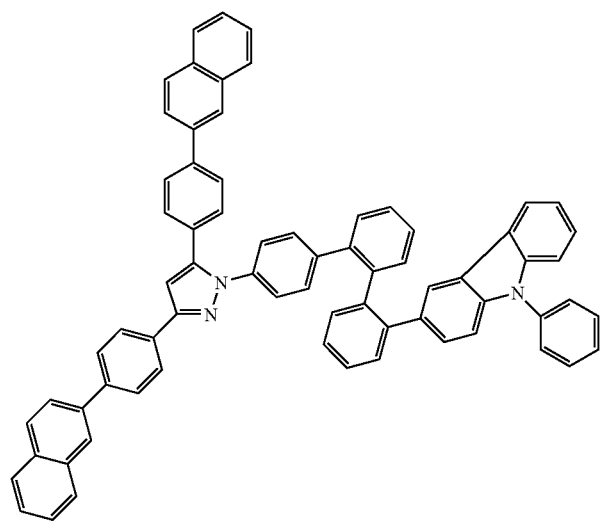
(281)
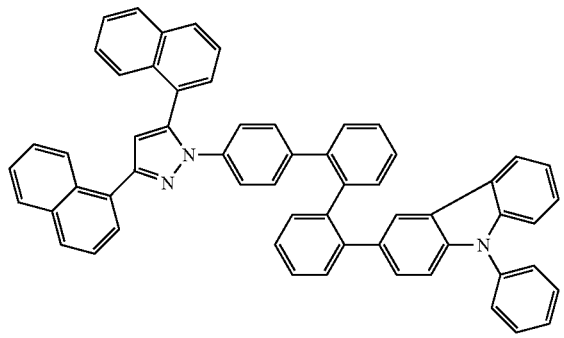
(282)
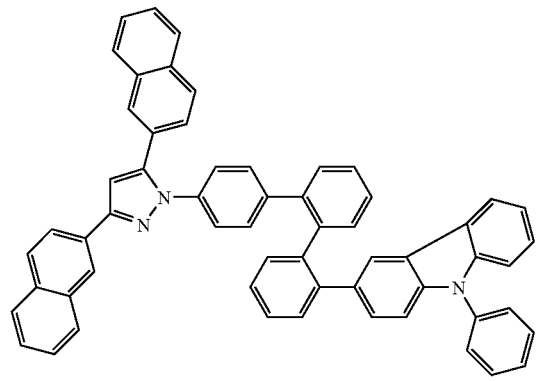

(283)
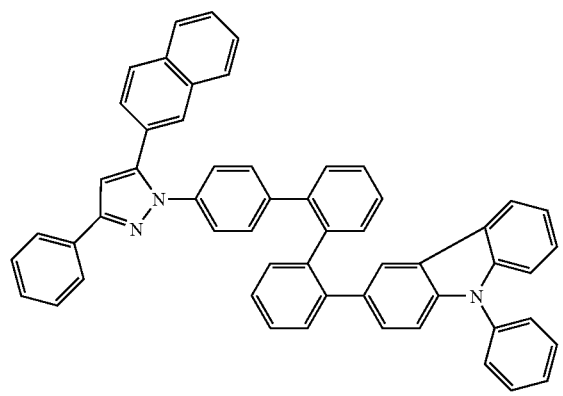
(284)
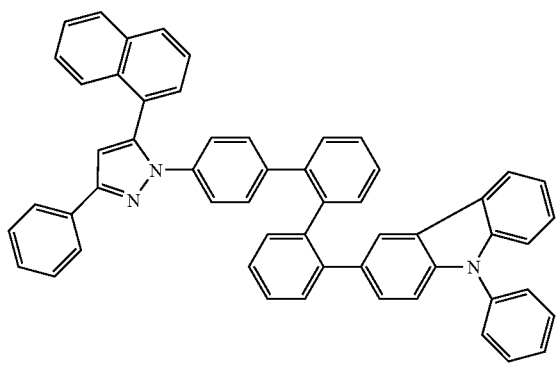
(285)
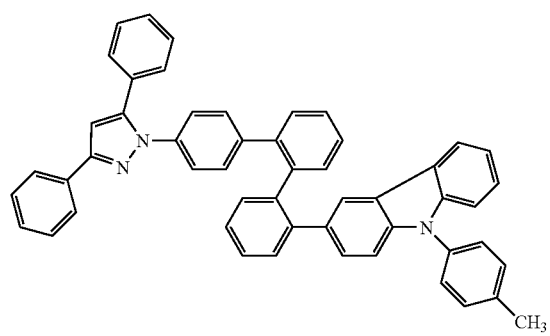
(286)
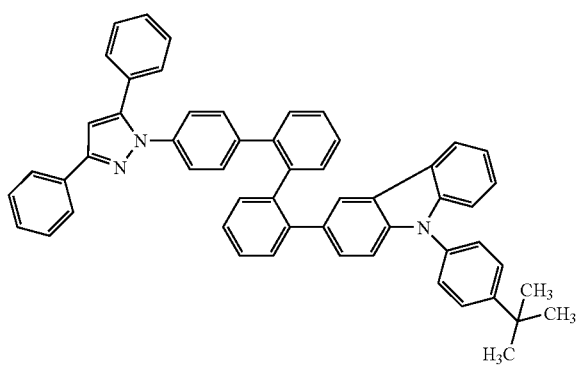
(287)
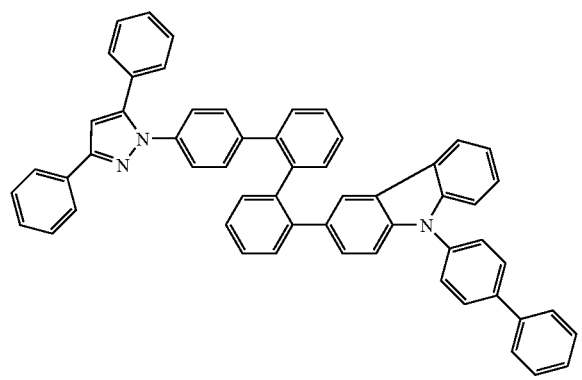
(288)
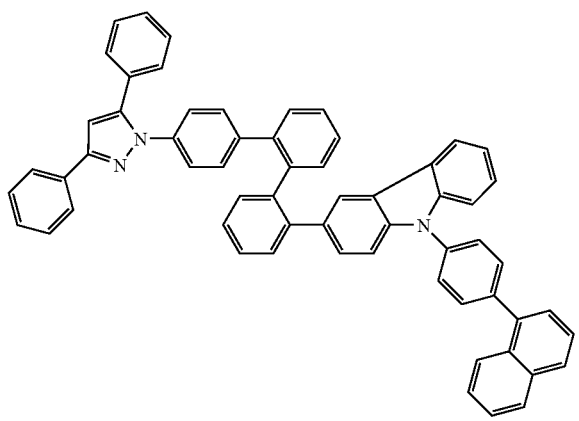

-continued
(289)
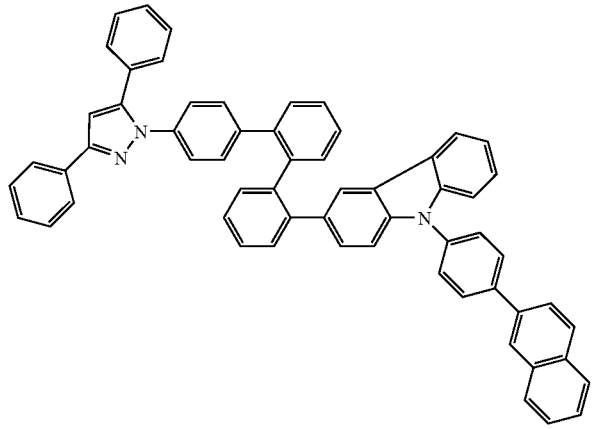
(290)
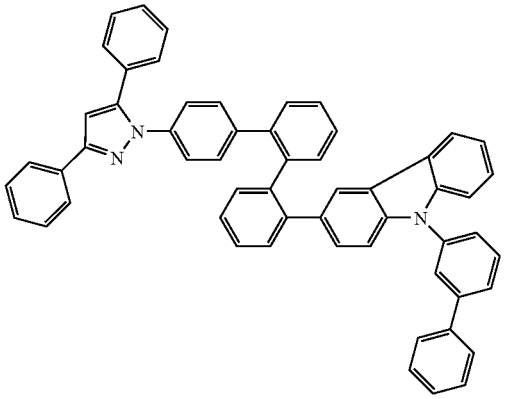
(291)
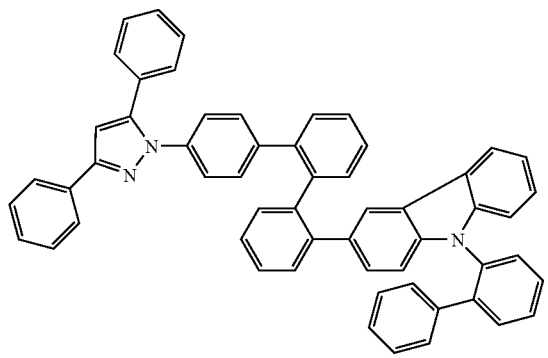
(292)
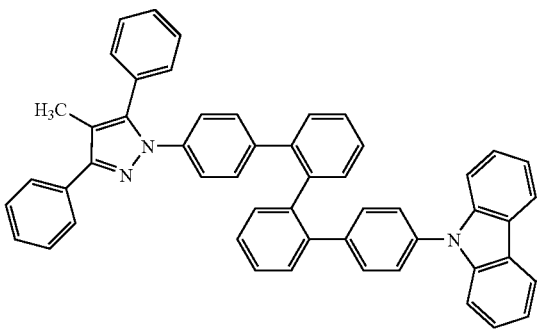
(293)
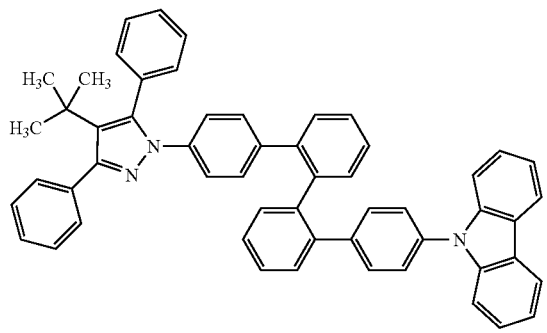
(294)
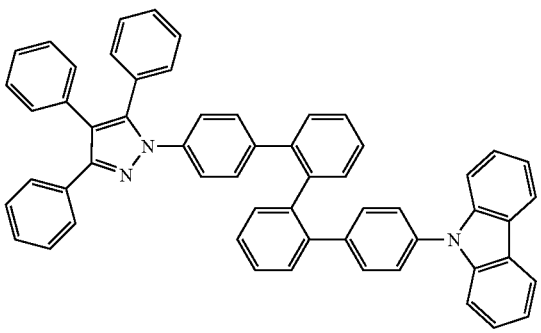
(295)
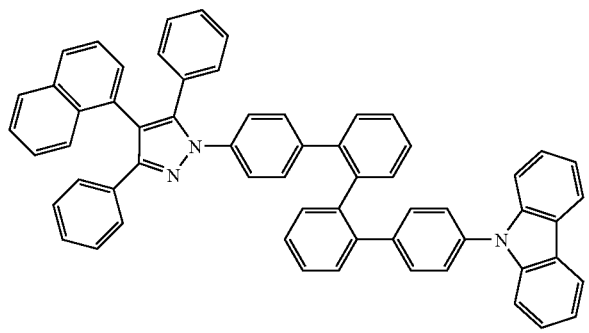
(296)
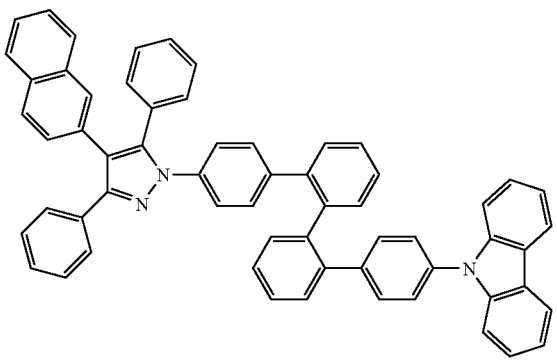

-continued
(297)
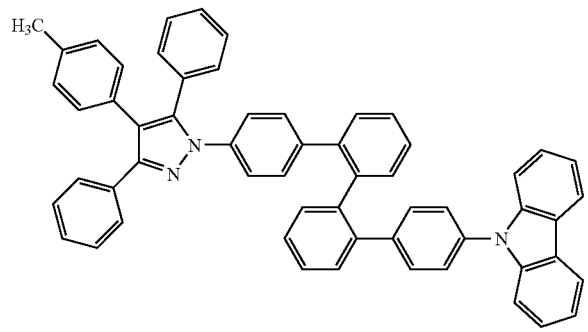
(298)
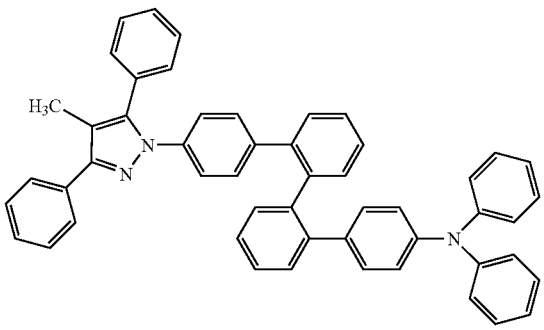
(299)
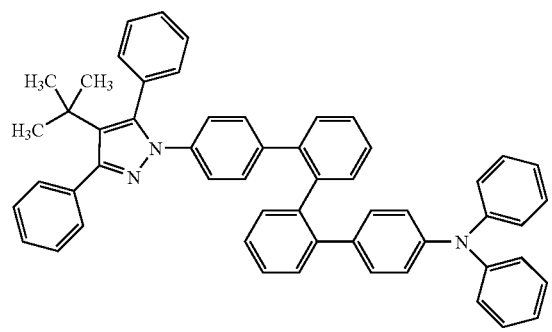
(300)
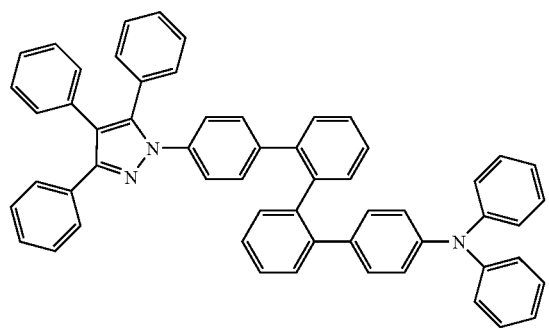
(301)
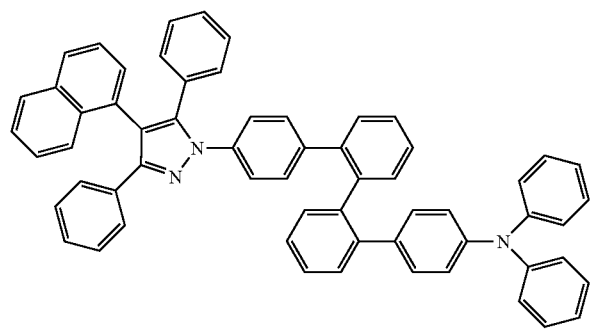
(302)
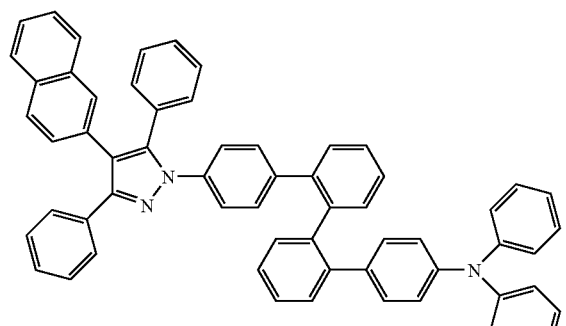
(303)
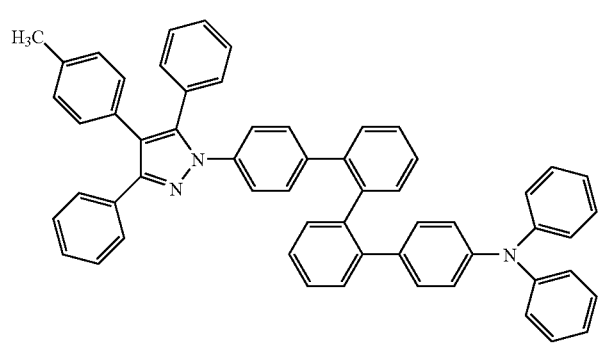
(304)
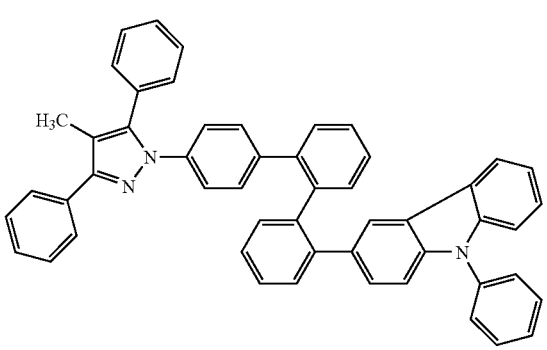

-continued
(305)
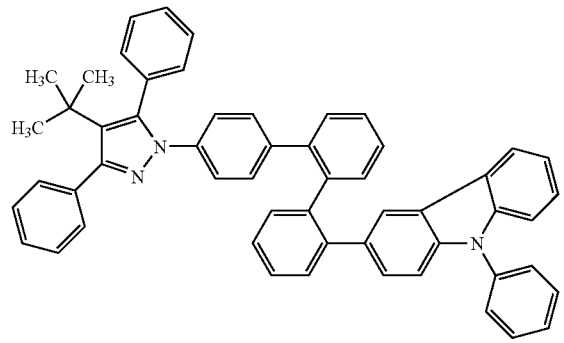
(306)
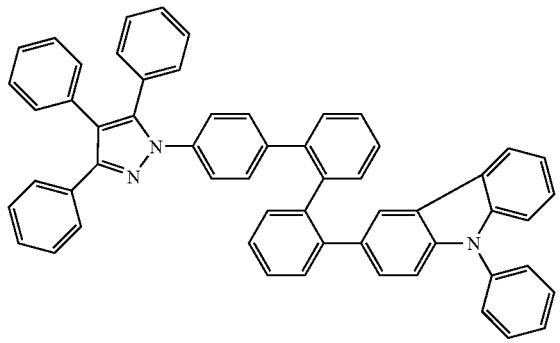
(307)
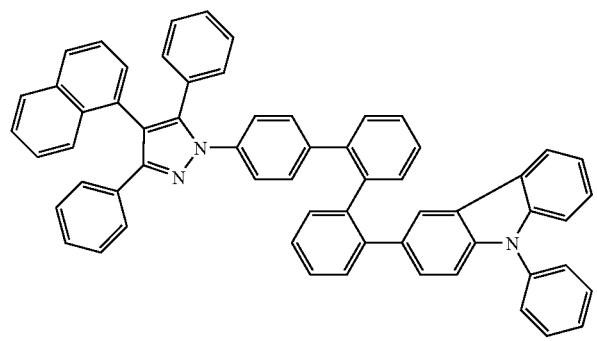
(308)
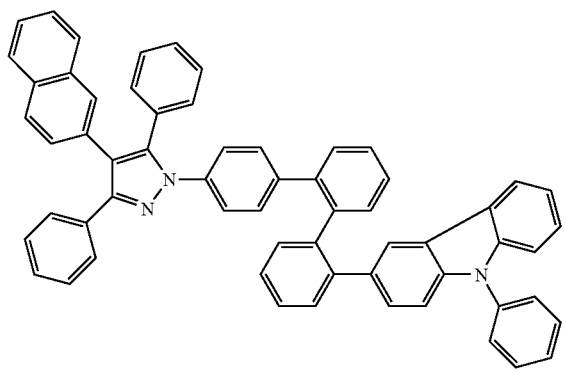
(309)
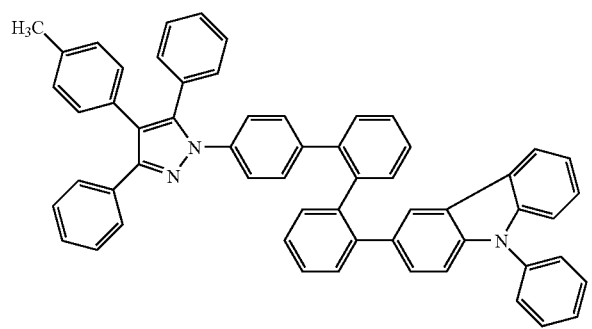
(310)
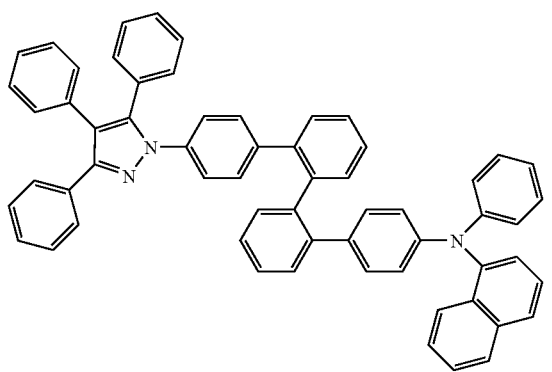
(311)
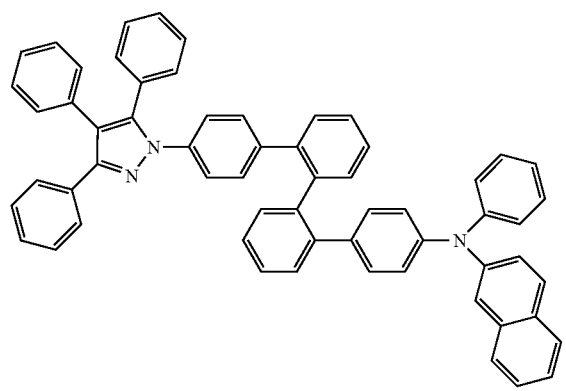
(312)
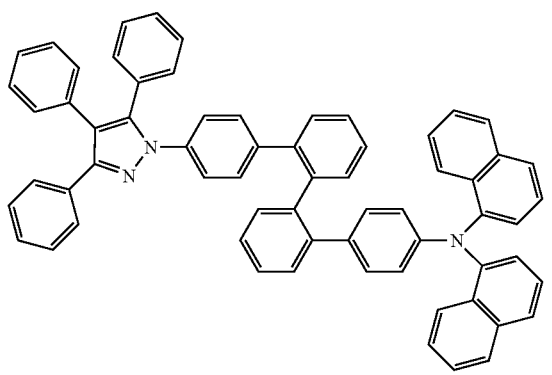

(313)

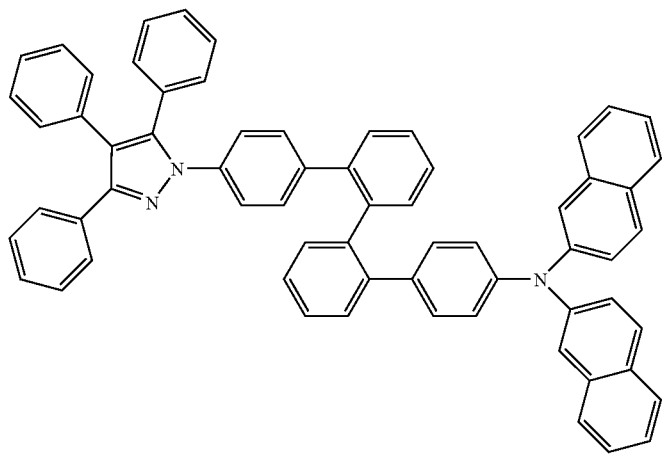

The heterocyclic compound represented by the general formula (G1) can be synthesized by synthesis methods represented by synthesis schemes (M-1) to (M-5) below. Hereinafter, an example of a synthesis method of the heterocyclic compound of this embodiment will be described.

First, a halogenated amine compound (Compound A) is synthesized. The synthesis scheme (M-1) is shown below.

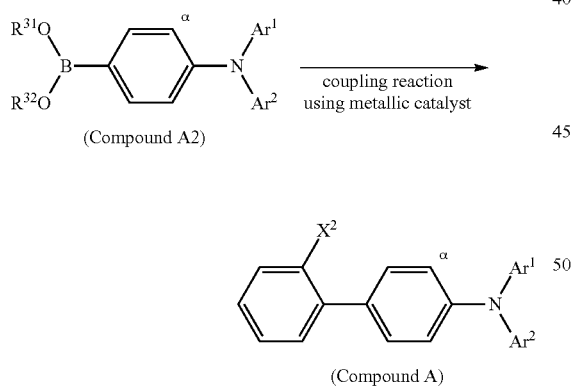

The halogenated amine compound (Compound A) can be synthesized as in the synthesis scheme (M-1). In other words, the halogenated amine compound (Compound A) can be obtained in such a manner that dihalogenated benzene (Compound A1) and an arylamine compound with a boronic acid or organoboron (Compound A2) are coupled employing the Suzuki-Miyaura coupling using a palladium catalyst in the presence of a base.

In the synthetic scheme (M-1), $X^1$ and $X^2$ independently represent halogen or a triflate group, and iodine, bromine, and chlorine are preferable as the halogen. In the synthetic scheme (M-1), $R^{31}$ and $R^{32}$ independently represent a hydrogen atom or an alkyl group having 1 to 6 carbon atoms, and $R^{31}$ and $R^{32}$ may be bonded to each other to form a ring structure.

In the synthetic scheme (M-1), $Ar^1$ and $Ar^2$ independently represent an aryl group having 6 to 10 carbon atoms in a ring and may each have a substituent.

Examples of a palladium catalyst which can be used in the synthetic scheme (M-1) include palladium(II) acetate and tetrakis(triphenylphosphine)palladium(0). As a ligand of the palladium catalyst that can be used in the synthesis scheme (M-1), tri(o-tolyl)phosphine, triphenylphosphine, tricyclohexylphosphine, and the like can be given.

Examples of a base that can be used in the synthesis scheme (M-1) include an organic base such as sodium tert-butoxide and an inorganic base such as potassium carbonate. Examples of solvents that can be used in the synthesis scheme (M-1) include a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of an ether such as 1,2-dimethoxyethane and water; and the like. Use of a mixed solvent of toluene and water or a mixed solvent of toluene, ethanol, and water is more preferable.

Next, the halogenated arylamine compound (Compound A) obtained with the synthesis scheme (M-1) undergoes boron oxidation using an alkyl lithium reagent and a boron reagent, whereby an arylamine compound with a boronic acid or organoboron (Compound B) can be obtained. The synthesis scheme (M-2) is shown below.

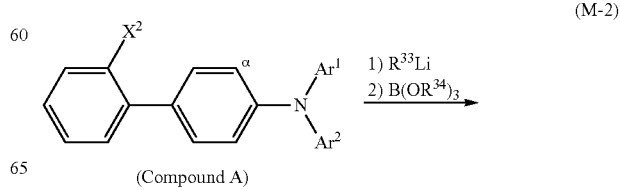

-continued

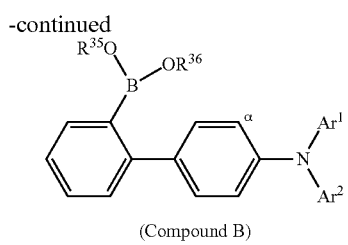

(Compound B)

In the synthetic scheme (M-2), $R^{33}$ and $R^{34}$ independently represent an alkyl group having 1 to 6 carbon atoms. $R^{35}$ and $R^{36}$ independently represent a hydrogen atom or an alkyl group having 1 to 6 carbon atoms. $R^{35}$ and $R^{36}$ may be bonded to each other to form a ring structure.

In the synthesis scheme (M-2), n-butyllithium, methyllithium, or the like can be used as an alkyl lithium reagent. Trimethyl borate, triisopropyl borate, or the like can be used as a boron reagent.

Next, a halogenated amine compound (Compound C) can be obtained in such a manner that dihalogenated benzene (Compound C1) and the arylamine compound with a boronic acid or organoboron obtained with the synthetic scheme (M-2) (Compound B) are coupled employing the Suzuki-Miyaura coupling using a palladium catalyst in the presence of a base. The synthesis scheme (M-3) is shown below.

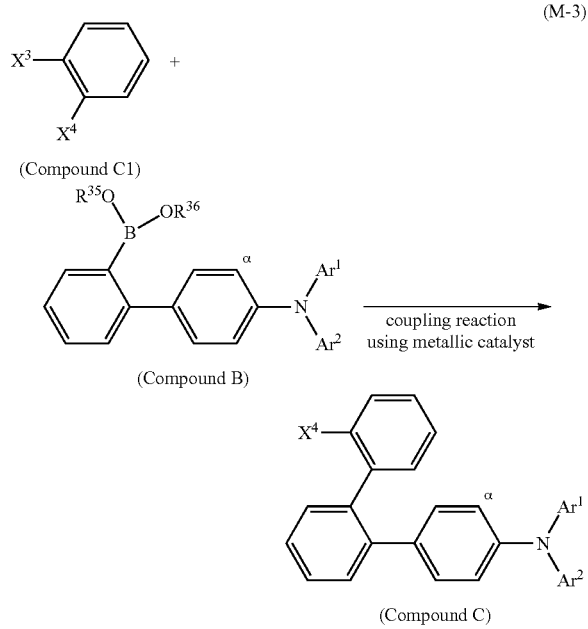

In the synthetic scheme (M-3), $X^3$ and $X^4$ independently represent halogen or a triflate group, and iodine, bromine, or chlorine is preferable as the halogen.

Examples of a palladium catalyst which can be used in the synthetic scheme (M-3) include palladium(II) acetate and tetrakis(triphenylphosphine)palladium(0). Examples of a ligand of the palladium catalyst which can be used in the synthetic scheme (M-3) include tri(o-tolyl)phosphine, triphenylphosphine, and tricyclohexylphosphine.

Examples of a base that can be used in the synthesis scheme (M-3) include an organic base such as sodium tert-butoxide and an inorganic base such as potassium carbonate. Examples of solvents that can be used in the synthesis scheme (M-3) include a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of an ether such as 1,2-dimethoxyethane and water; and the like. Use of a mixed solvent of toluene and water or a mixed solvent of toluene, ethanol, and water is more preferable.

Next, the halogenated arylamine compound (Compound C) obtained with the synthesis scheme (M-3) undergoes boron oxidation using an alkyl lithium reagent and a boron reagent, whereby an arylamine compound with a boronic acid or organoboron (Compound D) can be obtained. The synthesis scheme (M-4) is shown below.

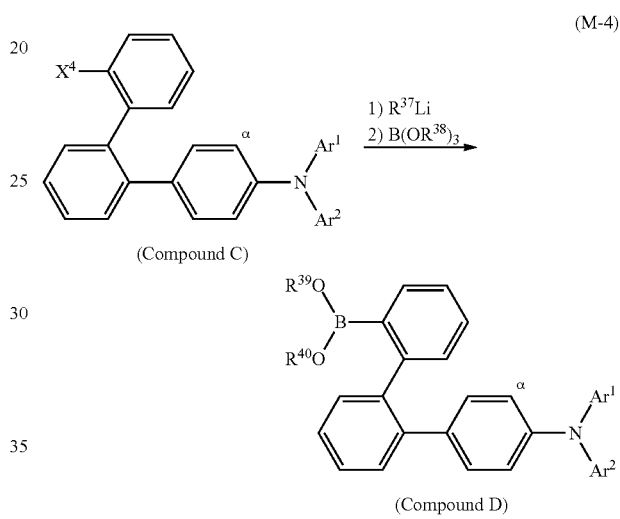

In the synthetic scheme (M-4), $R^{37}$ and $R^{38}$ independently represent an alkyl group having 1 to 6 carbon atoms. $R^{39}$ and $R^{40}$ independently represent a hydrogen atom or an alkyl group having 1 to 6 carbon atoms. $R^{39}$ and $R^{40}$ may be bonded to each other to form a ring structure.

In the synthesis scheme (M-4), n-butyllithium, methyllithium, or the like can be used as the alkyllithium reagent. Trimethyl borate, triisopropyl borate, or the like can be used as the boron reagent.

Next, the heterocyclic compound of this embodiment represented by the general formula (G1) can be obtained in such a manner that a halogenated compound having a heteroaromatic ring (Compound E1) and the arylamine compound with a boronic acid or organoboron obtained with the synthetic scheme (M-4) (Compound D) are coupled employing the Suzuki-Miyaura coupling using a palladium catalyst in the presence of a base. The synthesis scheme (M-5) is shown below.

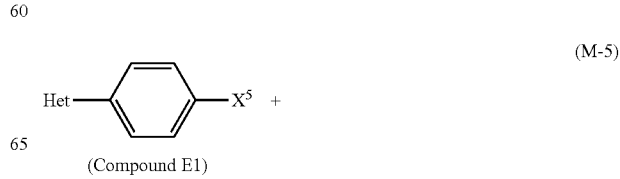

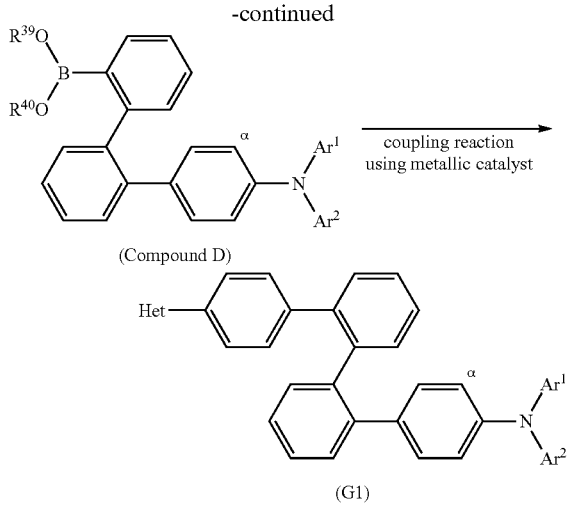

(Compound D)

coupling reaction
using metallic catalyst (G1)

Note that in the synthesis scheme (M-5), Het represents any one of substituents represented by the following general formulae (S1-1) and (S1-2).

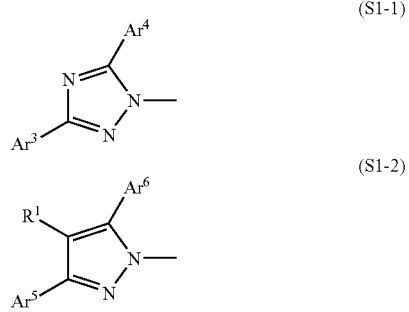

In the general formulae (S1-1) and (S1-2), $Ar^3$ to $Ar^6$ independently represent an aryl group having 6 to 10 carbon atoms in a ring and may each have a substituent. In addition, in the general formula (S1-2), $R^1$ represents any one of a hydrogen atom, an alkyl group having 1 to 4 carbon atoms, and an aryl group having 6 to 10 carbon atoms in a ring.

In the synthesis scheme (M-5), $X^5$ represents halogen or a triflate group, and iodine, bromine, or chlorine is preferable as the halogen.

Examples of a palladium catalyst which can be used in the synthetic scheme (M-5) include palladium(II) acetate and tetrakis(triphenylphosphine)palladium(0). Examples of a ligand of the palladium catalyst which can be used in the synthetic scheme (M-5) include tri(o-tolyl)phosphine, triphenylphosphine, and tricyclohexylphosphine.

Examples of a base that can be used in the synthesis scheme (M-5) include an organic base such as sodium tert-butoxide and an inorganic base such as potassium carbonate. Examples of solvents that can be used in the synthesis scheme (M-5) include a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of an ether such as 1,2-dimethoxyethane and water; and the like. Use of a mixed solvent of toluene and water or a mixed solvent of toluene, ethanol, and water is more preferable.

Thus, the heterocyclic compound of this embodiment can be synthesized.

Any of the heterocyclic compounds in this embodiment has high triplet excitation energy, and an electron-transporting property and a hole-transporting property. Thus, any of the heterocyclic compounds can be favorably used for a light-emitting element. Since the balance between injected electrons and holes is important particularly for a light-emitting layer of a light-emitting element, any of the heterocyclic compounds in this embodiment is preferably used for a light-emitting layer. Since any of the heterocyclic compounds in this embodiment has high triplet excitation, energy, it can be used for a light-emitting layer together with a substance which emits phosphorescence.

Furthermore, since the singlet excitation energy (the difference in energy between the ground state and the singlet excited state) is greater than the triplet excitation energy, a substance that has high triplet excitation energy also has high singlet excitation energy. Therefore, any of the heterocyclic compounds in this embodiment, which has high triplet excitation energy, is useful even in the case of being used for a light-emitting layer, together with a substance that emits fluorescence.

Further, in any of the heterocyclic compounds in this embodiment, a heteroaromatic ring skeleton having an electron-transporting property and a skeleton having a hole-transporting property are bonded to each other with a twisted quaterphenylene skeleton that inhibits extension of conjugation therebetween, whereby the molecular weight can be increased with high triplet excitation energy maintained. Thus, the heterocyclic compound can have high thermal stability.

Further, any of the heterocyclic compounds in this embodiment can transport carriers and thus can be used for a carrier-transporting layer in a light-emitting element. In particular, any of the heterocyclic compounds in this embodiment has high triplet excitation energy; therefore, energy transfer from a light-emitting layer does not easily occur even in the case where the heterocyclic compound is used for a layer in contact with a light-emitting layer. Accordingly, high emission efficiency can be achieved.

Embodiment 2

An embodiment of a light-emitting element using any of the heterocyclic compounds of Embodiment 1 will be described with reference to FIG. 1A.

In the light-emitting element of this embodiment, an EL layer having at least a layer that includes a light-emitting substance (also referred to as a light-emitting layer) is interposed between a pair of electrodes. The EL layer may also have a plurality of layers in addition to the layer that includes a light-emitting substance. The plurality of layers are a combination of layers formed of a substance having a high carrier-injecting property and a substance having a high carrier-transporting property, which are stacked so that a light-emitting region can be formed in a region away from the electrodes, that is, so that carriers can be recombined in an area away from the electrodes. In this specification, the layer formed of a substance having a high carrier-injecting property or a substance having a high carrier-transporting property is also referred to as a functional layer functioning to inject or transport carriers or the like. For the functional layer, it is possible to use a layer that includes a substance having a high hole-injecting property (also referred to as a hole-injecting layer), a layer that includes a substance having a high hole-transporting property (also referred to as a hole-transporting layer), a layer that includes a substance having a high electron-injecting property (also referred to as an electron-injecting layer), a layer that includes a substance having a high electron-transporting property (also referred to as an electron-transporting layer), and the like.

Figure 1B:
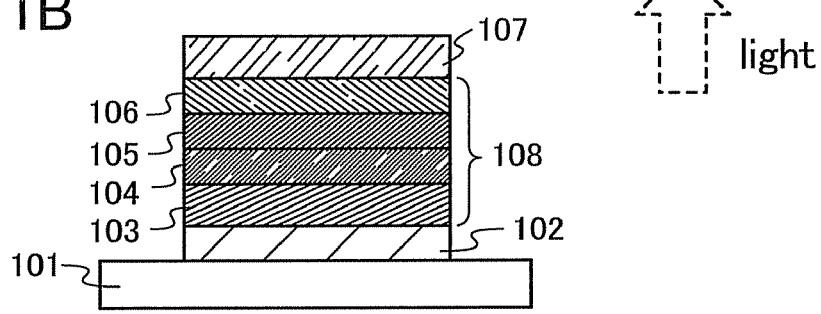
Figure 1C:
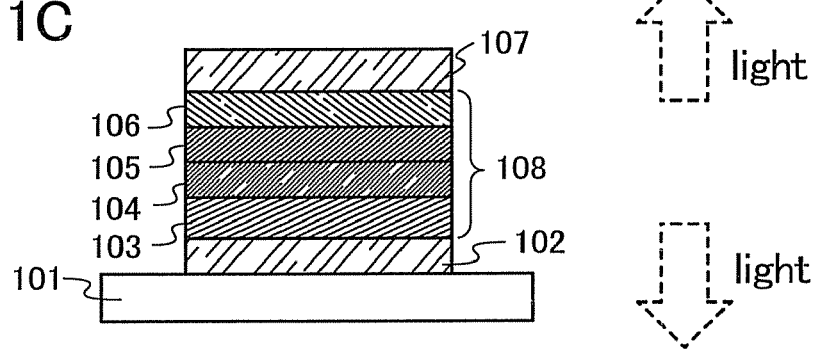

In a light-emitting element of this embodiment in each of FIGS. 1A to 1C, an EL layer 108 is provided between a pair of electrodes: a first electrode 102 and a second electrode 107. The EL layer 108 has a first layer 103, a second layer 104, a third layer 105, and a fourth layer 106. In the light-emitting element of each of FIGS. 1A to 1C, the first electrode 102 is formed over a substrate 101; the first layer 103, the second layer 104, the third layer 105, and the fourth layer 106 are stacked over the first electrode 102 in this order; and the second electrode 107 is provided over the fourth layer 106. In description of this embodiment, the first electrode 102 functions as an anode and the second electrode 107 functions as a cathode.

The substrate 101 is used as a support of the light-emitting element. For the substrate 101, a glass substrate, a quartz substrate, a plastic substrate, or the like can be used. Furthermore, a flexible substrate may be used. The flexible substrate is a substrate that can be bent, such as a plastic substrate made of polycarbonate, polyarylate, or polyether sulfone. Alternatively, a film (made of polypropylene, polyester, vinyl, polyvinyl fluoride, vinyl chloride, or the like), or an inorganic film formed by evaporation can be used. Note that any other material can be used as long as it can function as a support of a light-emitting element in a manufacturing process of the light-emitting element.

The first electrode 102 is preferably formed of a metal, an alloy, a conductive compound, a mixture of any of these, or the like each having a high work function (specifically, a work function of 4.0 eV or higher). Specifically, for example, indium tin oxide (ITO), indium tin oxide including silicon or silicon oxide, indium zinc oxide (IZO), indium oxide including tungsten oxide and zinc oxide (IWZO), and the like can be given. Films of these conductive metal oxides are usually formed by sputtering; however, a sol-gel method or the like may be used. For example, indium zinc oxide (IZO) can be formed by a sputtering method using indium oxide to which 1 wt % to 20 wt % of zinc oxide is added, as a target. Moreover, indium oxide including tungsten oxide and zinc oxide (IWZO) can be formed by a sputtering method using indium oxide including 0.5 wt % to 5 wt % of tungsten oxide and 0.1 wt % to 1 wt % of zinc oxide, as a target. In addition, gold (Au), platinum (Pt), nickel (Ni), tungsten (W), chromium (Cr), molybdenum (Mo), iron (Fe), cobalt (Co), copper (Cu), palladium (Pd), nitride of a metal material (such as titanium nitride), and the like can be given.

The first layer 103 includes a substance having a high hole-injecting property. As the substance having a high hole-injecting property, molybdenum oxide, vanadium oxide, ruthenium oxide, tungsten oxide, manganese oxide, or the like can be used. Alternatively, the first layer 103 can be formed using phthalocyanine (abbreviation: H$_2$Pc); a phthalocyanine-based compound such as copper phthalocyanine (CuPc); an aromatic amine compound such as 4,4'-bis[N-(4-diphenylaminophenyl)-N-phenylamino]biphenyl (abbreviation: DPAB) or N,N''-bis[4-[bis(3-methylphenyl)amino]phenyl]-N,N'-diphenyl-[1,1'-biphenyl]-4,4'-diamine (abbreviation: DNIPD); a macromolecular material such as poly(3,4-ethylene dioxythiophene)/poly(styrenesulfonic acid) (PEDOT/PSS); or the like.

In addition, the first layer 103 can be formed using a composite material including an organic compound and an inorganic compound. In particular, the composite material including an organic compound and an inorganic compound showing an electron-accepting property to the organic compound has a high hole-injecting property and a high hole-transporting property, because electron transfer is conducted between the organic compound and the inorganic compound, so that carrier density increases.

In the case where the first layer 103 is formed using a composite material including an organic compound and an inorganic compound, ohmic contact with the first electrode 102 becomes possible, and thus the material for the first electrode can be selected regardless of its work function.

As the inorganic compound used for the composite material, oxide of a transition metal is preferably used. In addition, oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable since their electron-accepting property is high. Among them, molybdenum oxide is particularly preferable since it is stable in the air, has a low hygroscopic property, and is easily handled.

As the organic compound used for the composite material, any of various compounds such as an aromatic amine compound, carbazole derivatives, aromatic hydrocarbon, and a macromolecular compound (including oligomer and dendrimer) can be used. The organic compound used for the composite material is preferably an organic compound having a high hole-transporting property. Specifically, a substance having a hole mobility of $10^{-6}$ cm$^2$/Vs or higher is preferably used. The organic compounds which can be used for the composite material will be specifically given below.

Examples of the aromatic amine compound include N,N''-di(p-tolyl)-N,N''-diphenyl-p-phenylenediamine (abbreviation: DTDPPA); 4,4'-bis[N-(4-diphenylaminophenyl)-N-phenylamino]biphenyl (abbreviation: DPAB); N,N'-bis[4-[bis(3-methylphenyl)amino]phenyl]-N,N'-diphenyl-[1,1'-biphenyl]-4,4'-diamine (abbreviation: DNTPD), and 1,3,5-tris[N-(4-diphenylaminophenyl)-N-phenylamino]benzene (abbreviation: DPA3B).

As carbazole derivatives which can be used for the composite material, 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3[N-(1-naphthyl)-N-(9-phenylcarbazol-3-yl)amino]-9-phenylcarbazole (abbreviation: PCzPCN1); and the like can specifically be given.

Moreover, 4,4'-di(N-carbazolyl)biphenyl (abbreviation: CBP); 1,3,5-tris[4-(N-carbazolyl)phenyl]benzene (abbreviation: TCPB); 9-[4-(N-carbazolyl)]phenyl-10-phenylanthracene (abbreviation: CzPA); 1,4-bis[4-(N-carbazolyl)phenyl]-2,3,5,6-tetraphenylbenzene; and the like can also be given.

Examples of the aromatic hydrocarbon which can be used for the composite material include 2-tert-butyl-9,10-di(2-naphthyl)anthracene (abbreviation: t-BuDNA); 2-tert-butyl-9,10-di(1-naphthyl)anthracene; 9,10-bis(3,5-diphenylphenyl)anthracene (abbreviation: DPPA); 2-tert-butyl-9,10-bis(4-phenylphenyl)anthracene (abbreviation: t-BuDBA); 9,10-di(2-naphthyl)anthracene (abbreviation: DNA); 9,10-diphenylanthracene (abbreviation: DPAnth); 2-tert-butylanthracene (abbreviation: t-BuAnth); 9,10-bis(4-methyl-1-naphthyl)anthracene (abbreviation: DMNA); 2-tert-butyl-9,10-bis[2-(1-naphthyl)phenyl]anthracene; 9,10-bis[2-(1-naphthyl)phenyl]anthracene; 2,3,6,7-tetramethyl-9,10-di(1-naphthyl)anthracene; 2,3,6,7-tetramethyl-9,10-di(2-naphthyl)anthracene; 9,9'-bianthryl; 10,10'-diphenyl-9,9'-bianthryl; 10,10'-bis(2-phenylphenyl)-9,9'-bianthryl; 10,10'-bis[(2,3,4,5,6-pentaphenyl)phenyl]-9,9'-bianthryl; anthracene; tetracene; rubrene; perylene; and 2,5,8,11-tetra(tert-butyl)perylene. Besides those, pentacene, coronene, or the like can also be used. In particular, the aromatic hydrocarbon which has a hole mobility of $1\times10^{-6}$ cm$^2$/Vs or higher and which has 14 to 42 carbon atoms is preferable.

Any of the heterocyclic compounds described in Embodiment 1 may be used for the composite material.

The aromatic hydrocarbon which can be used for the composite material may have a vinyl skeleton. As the aromatic hydrocarbon having a vinyl group, 4,4'-bis(2,2-diphenylvinyl)biphenyl (abbreviation: DPVBi); 9,10-bis[4-(2,2-diphenylvinyl)phenyl]anthracene (abbreviation: DPVPA); and the like can be given.

Moreover, a macromolecular compound such as poly(N-vinylcarbazole) (abbreviation: PVK) or poly(4-vinyltriphenylamine) (abbreviation: PVTPA) may be used.

As a substance for forming the second layer 104, a substance having a high hole-transporting property, specifically, an aromatic amine compound (that is, a compound having a benzene ring-nitrogen bond) is preferably used. As examples of the material widely used, 4,4'-bis[N-(3-methylphenyl)-N-phenylamino]biphenyl; a derivative thereof such as 4,4'-bis[N-(1-napthyl)-N-phenylamino]biphenyl (hereinafter referred to as NPB); and a starburst aromatic amine compound such as 4,4',4''-tris(N,N-diphenyl-amino)triphenylamine, 4,4',4''-tris[N-(3-methylphenyl)-N-phenylamino]triphenylamine, and the like can be given. The substances mentioned here are mainly ones that have a hole mobility of $10^{-6}$ cm$^2$/Vs or higher. Note that the second layer 104 is not limited to a single layer, but may be a mixed layer or a stacked layer of two or more layers, which is formed with the substances.

Any of the heterocyclic compounds described in Embodiment 1 can be used as a hole-transporting material.

Alternatively, a material having a hole-transporting property may be added to a macromolecular compound that is electrically inactive, such as polymethyl methacrylate (abbreviation: PMMA).

Still alternatively, a macromolecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide](abbreviation: PTPDMA), or poly[N,N'-bis(4-butylphenyl)-N,N'-bis(phenyl)benzidine (abbreviation: poly-TPD) may be used, and further, the material having a hole-transporting property may be added to the macromolecular compound, as appropriate.

The third layer 105 is a layer including a light-emitting substance (also referred to as a light-emitting layer). In this embodiment, the third layer 105 is formed using any of the heterocyclic compounds described in Embodiment 1. For example, each heterocyclic compound described in Embodiment 1 exhibits light emission ranging from purple to blue, and thus can be favorably used for the light-emitting element as a light-emitting substance.

Further, any of the heterocyclic compounds of Embodiment 1 may be used as a host of the third layer 105, and with a structure in which a dopant serving as a light-emitting substance is dispersed in the heterocyclic compound of Embodiment 1, light emission from the dopant serving as a light-emitting substance can be obtained. Since any of the heterocyclic compounds of Embodiment 1 has high excitation energy, it is particularly preferable to apply the structure in which a light-emitting substance is dispersed in the heterocyclic compound.

When any of the heterocyclic compounds of Embodiment 1 is used as a material in which another light-emitting substance is dispersed, an emission color depending on the light-emitting substance can be obtained. Further, it is also possible to obtain an emission color that is a mixture of an emission color depending on the heterocyclic compound in Embodiment 1 and the emission color depending on the light-emitting substance dispersed in the heterocyclic compound.

As the light-emitting substance which is dispersed in the heterocyclic compound described in Embodiment 1, a substance that emits fluorescence or a substance that emits phosphorescence can be used.

When a substance that emits phosphorescence (a phosphorescent compound) is used, it is possible to use any of a variety of substances without particular limitation; however, a substance having triplet excitation energy lower than that of any of the heterocyclic compounds described in Embodiment 1 is preferably used. Since any of the heterocyclic compounds described in Embodiment 1 has high triplet excitation energy, there are a variety of choices of phosphorescent compounds which can be used for the light-emitting layer.

As a phosphorescent compound which can be used for the light-emitting layer in addition to any of the heterocyclic compounds described in Embodiment 1, the following can be given, for example: iridium complexes such as tris(2-phenylpyridinato)iridium(III) (abbreviation: Ir(ppy)$_3$), bis(2-phenylpyridinato)iridium(III) acetylacetonato (abbreviation: Ir(ppy)$_2$(acac)), bis{2-(p-tolyl)pyridinato}iridium(III) acetylacetonate (abbreviation: Ir(tpy)$_2$(acac)), bis{2-(2'-benzothienyl)pyridinato}iridium(III)acetylacetonate (abbreviation: Ir(btp)$_2$(acac)), and bis[2-(4',6'-difluorophenyl)pyridinato-N,C$^{2'}$]iridium(III) picolinate (abbreviation: FIrpic); platinum complexes such as a 2,3,7,8,12,13,17,18-octaethyl-21H,23H-porphyrin-platinum complex (Pt(OEP)); and rare-earth complexes such as 4,7-diphenyl-1,10-phenanthrolinetris(2-tenoyltrifluoroacetonato)europium(III).

When a substance that emits fluorescent is used, it is possible to use any of a variety of materials without particular limitation; however, a substance having singlet excitation energy lower than that of any of the heterocyclic compounds described in Embodiment 1 is preferably used. Since any of the heterocyclic compounds described in Embodiment 1 has high singlet excitation energy, there are a variety of choices of fluorescent compounds which can be used for the light-emitting layer.

As a fluorescent compound which can be used for the light-emitting layer in addition to any of the heterocyclic compounds described in Embodiment 1, the following can be given, for example: coumarin derivatives such as coumarin 6 and coumarin 545T; quinacridone derivatives such as N,N'-dimethylquinacridone and N,N'-diphenylquinacridone; acridone derivatives such as N-phenylacridone and N-methylacridone; condensed aromatic compounds such as 2-tert-butyl-9,10-di(2-naphthyl)anthracene (abbreviation: t-BuDNA), 9,10-diphenylanthracene (abbreviation: DPhA), rubrene, periflanthene, and 2,5,8,11-tetra(tert-butyl)perylene (abbreviation: TBP); pyran derivatives such as 4-dicyanomethylene-2-[p-(dimethylamino)styryl]-6-methyl-4H-pyran; and amine derivatives such as 4-(2,2-diphenylvinyl)triphenylamine, 9-(4-{N-[4-(carbazol-9-yl)phenyl]-N-phenylamino}phenyl)-10-phenylanthracene (abbreviation: YGAPA), and 4-(10-phenyl-9-anthryl)-4'-(9-phenyl-9H-carbazol-3-yl)triphenylamine (abbreviation: PCBAPA).

By formation of a light-emitting element in which any of the heterocyclic compounds described in Embodiment 1 is added to a layer including a material (host) that has a band gap larger than the heterocyclic compound, light emission from any of the heterocyclic compounds described in Embodiment 1 can be obtained. In other words, any of the heterocyclic compounds described in Embodiment 1 can serve as a dopant.

The fourth layer 106 can be formed using a substance having a high electron-transporting property. For example, a layer including a metal complex or the like having a quinoline skeleton or a benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo[h]-quinolinato)beryllium (abbreviation: BeBq$_2$), or bis(2-methyl-8-quinolinolato)(4-phenylphenolato)aluminum (abbreviation: BAlq), or the like can be used. Alternatively, a metal complex or the like including an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$) can be used. Other than the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like may be used. The substances mentioned here are mainly ones each having an electron mobility of $10^{-6}$ cm$^2$/Vs or higher. Furthermore, the electron-transporting layer is not limited to a single layer, and two or more layers made of any of the substances may be stacked.

Any of the heterocyclic compounds described in Embodiment 1 may be used for an electron-transporting material.

Further, a layer having a function of promoting electron injection (an electron-injecting layer) may be provided between the fourth layer 106 and the second electrode 107. As the layer having a function of promoting electron injection, an alkali metal, an alkaline-earth metal, or a compound thereof such as lithium fluoride (LiF), cesium fluoride (CsF), or calcium fluoride (CaF$_2$) can be used. An alkali metal, an alkaline-earth metal, or a compound thereof may be included in a layer formed using an electron-transporting substance; for example, a layer in which magnesium (Mg) is included in Alq, or the like can be used as the electron-injecting layer. Note that it is preferable to use the layer formed using a substance having an electron-transporting property, which includes an alkali metal or an alkaline-earth metal, as the electron-injecting layer, because electrons can be efficiently injected from the second electrode 107.

A composite material may be used for the electron-injecting layer. As an organic compound which can be used for the composite material, any of the heterocyclic compounds described in Embodiment 1 may be used.

As a substance for forming the second electrode 107, a metal, an alloy, a conductive compound, a mixture thereof, or the like having a low work function (specifically, of 3.8 eV or less) can be used. As specific examples of such a cathode material, an element belonging to Group 1 or Group 2 of the periodic table, that is, an alkali metal such as lithium (Li) or cesium (Cs); an alkaline-earth metal such as magnesium (Mg), calcium (Ca), or strontium (Sr); an alloy thereof (MgAg, AlLi); a rare-earth metal such as europium (Eu) or ytterbium (Yb); an alloy thereof; and the like can be given. However, by providing a layer having a function of promoting electron injection between the second electrode 107 and the fourth layer 106 so that it is stacked with the second electrode, various conductive materials such as Al, Ag, ITO, or ITO including silicon or silicon oxide can be used for the second electrode 107 regardless of the work function.

Further, since the heterocyclic compounds described in Embodiment 1 are bipolar materials each have a high electron-transporting property and a high hole-transporting property, any of the heterocyclic compounds may be used as a carrier-transport material for a functional layer of a light-emitting element. Since any of the heterocyclic compounds described in Embodiment 1 has high excitation energy, any of the heterocyclic compounds is used for the functional layer of the light-emitting element, so that the diffusion of excitons generated in the light-emitting layer to other layers can be prevented. As a result, a light-emitting element having a high light emission efficiency can be obtained.

Further, for the formation of the first layer 103, the second layer 104, the third layer 105, and the fourth layer 106, any of a variety of methods such as an evaporation method, a sputtering method, a droplet discharging method (an inkjet method), a spin coating method, and a printing method can be employed. A different formation method may be employed for each electrode or each layer.

In the case where a thin film is formed by a wet process using a liquid composition in which any of the heterocyclic compounds described in Embodiment 1 is dissolved in a solvent, a material for forming the thin film which includes the heterocyclic compound described in Embodiment 1 is dissolved in the solvent, the liquid composition is attached to a region where the thin film is to be fowled, and then the solvent is removed and solidification is performed, whereby the thin film is formed.

For the wet process, any of the following methods can be employed: a spin coating method, a roll coat method, a spray method, a casting method, a dipping method, a droplet discharging (ejecting) method (an ink-jet method), a dispenser method, a variety of printing methods (a method by which a thin film can be formed in a desired pattern, such as screen (stencil) printing, offset (planographic) printing, letterpress printing, or gravure (intaglio) printing), and the like. Note that the wet process is not limited to the above methods as long as the liquid composition of this embodiment is used.

In the composition, any of a variety of solvents can be used. For example, the heterocyclic compounds can be dissolved in solvents that have aromatic rings (e.g., a benzene ring), such as toluene, xylene, methoxybenzene (anisole), dodecylbenzene, or a mixed solvent of dodecylbenzene and tetralin. Further, any of the heterocyclic compounds can also be dissolved in an organic solvent that does not have an aromatic ring, such as dimethylsulfoxide (DMSO), dimethylformamide (DMF), or chloroform.

As other solvents, ketone solvents such as acetone, methyl ethyl ketone, diethyl ketone, n-propyl methyl ketone, and cyclohexanone; ester solvents such as ethyl acetate, n-propyl acetate, n-butyl acetate, ethyl propionate, γ-butyrolactone, and diethyl carbonate; ether solvents such as diethylether, tetrahydrofuran and dioxane; alcohol solvents such as ethanol, isopropanol, 2-methoxyethanol, and 2-ethoxyethanol; and the like can also be given.

Further, the composition described in this embodiment may also include another organic material. As the organic material, any of aromatic compounds or heteroaromatic compounds which are solid at room temperature can be used. For the organic material, any of low molecular compounds or macromolecular compounds can be used. When a low molecular compound is used, a low molecular compound having a substituent that is capable of increasing the solubility in a solvent (also referred to as a medium molecular compound) is preferably used.

The composition may further include a binder in order to improve quality of the film formed. For the binder, a macromolecular compound that is electrically inactive is preferable. Specifically, polymethylmethacrylate (abbreviation: PMMA), polyimide, or the like can be used.

In the light-emitting element of this embodiment which has the structure described above, the potential difference generated between the first electrode 102 and the second electrode 107 makes current flow, whereby holes and electrons recombine in the third layer 105 that includes a substance having a high light-emitting property and accordingly light is emitted. That is, a light-emitting region is formed in the third layer 105.

Light emission is extracted to the outside through one of or both the first electrode 102 and the second electrode 107. Accordingly, one of or both the first electrode 102 and the second electrode 107 include(s) a light-transmitting substance. When only the first electrode 102 is formed using a light-transmitting substance, light emission is extracted from the substrate side through the first electrode 102, as illustrated in FIG. 1A. In contrast, when only the second electrode 107 is formed using a light-transmitting substance, light emission is extracted from a side opposite to the substrate side through the second electrode 107, as illustrated in FIG. 1B. When both the first electrode 102 and the second electrode 107 are formed using a light-transmitting substance, light is extracted from both the substrate side and the side opposite to the substrate side through the first electrode 102 and the second electrode 107, as illustrated in FIG. 1C.

Note that the structure of the layers provided between the first electrode 102 and the second electrode 107 is not limited to the above. A structure other than the structure may be used as long as the light-emitting region in which holes and electrons are recombined is located away from the first electrode 102 and the second electrode 107 so that the quenching due to proximity of the light-emitting region and metal can be prevented.

In other words, a layered structure of the layer is not particularly limited, and a layer formed using a substance having a high electron-transporting property, a substance having a high hole-transporting property, a substance having a high electron-injecting property, a substance having a high hole-injecting property, a bipolar substance (a substance having a high electron-transporting property and a high hole-transporting property), a hole blocking material, or the like may freely be combined with a light-emitting layer including any of the heterocyclic compounds described in Embodiment 1.

Figure 2:
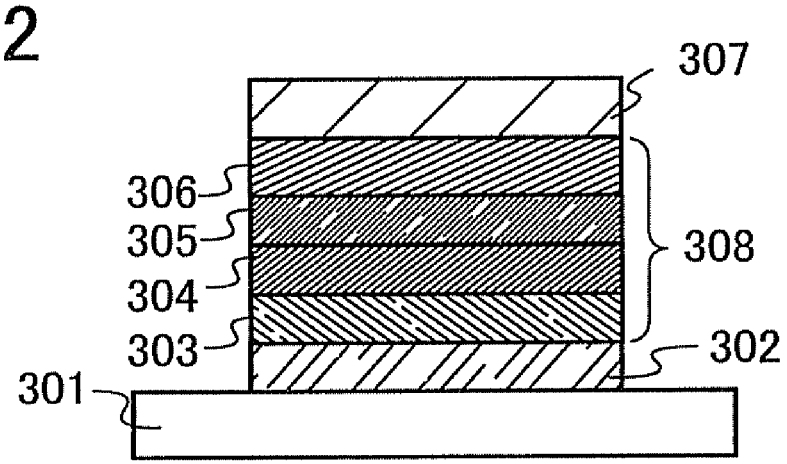
FIG. 2 illustrates a light-emitting element according to an embodiment of the present invention.

In a light-emitting element illustrated in FIG. 2, an EL layer 308 is provided between a pair of electrodes over a substrate 301: a first electrode 302 and a second electrode 307. The EL layer 308 includes a first layer 303 that includes a substance having a high electron-transporting property, a second layer 304 that includes a light-emitting substance, a third layer 305 that includes a substance having a high hole-transporting property, and a fourth layer 306 that includes a substance having a high hole-injecting property. The first electrode 302 that functions as a cathode, the first layer 303 that includes a substance having a high electron-transporting property, the second layer 304 that includes a light-emitting substance, the third layer 305 that includes a substance having a high hole-transporting property, the fourth layer 306 that includes a substance having a high hole-injecting property, and the second electrode 307 that functions as an anode are stacked in this order.

Hereinafter, a specific formation method of a light-emitting element will be described.

The light-emitting element of this embodiment has a structure in which an EL layer is interposed between a pair of electrodes. The EL layer at least has a layer that includes a light-emitting substance (also referred to as a light-emitting layer) and is formed using any of the heterocyclic compounds described in Embodiment 1. Furthermore, in addition to a layer that includes a light-emitting substance, the EL layer may include a functional layer (e.g., a hole-injecting layer, a hole-transporting layer, an electron-transporting layer, or an electron-injecting layer). The electrodes (the first electrode and the second electrode), the layer that includes a light-emitting substance, and the functional layer may be formed by any of the wet processes such as a droplet discharging method (an inkjet method), a spin coating method, and a printing method, or by any of the dry processes such as a vacuum evaporation method, a CVD method, and a sputtering method. The use of a wet process enables the formation at atmospheric pressure using a simple device and a simple process, thereby having the effects of simplifying the process and increasing the productivity. In contrast, in a dry process, dissolution of a material is not needed; therefore, a material that has low solubility in a solution can be used and thus there are a variety of choices of materials.

All the thin films included in the light-emitting element may be formed by a wet process. In that case, the light-emitting element can be formed with only facilities needed for a wet process. Alternatively, the stacked layers up to the layer that includes a light-emitting substance may be formed by a wet process whereas the functional layer, the second electrode, and the like which are stacked over the layer that includes a light-emitting substance may be formed by a dry process. Still alternatively, the first electrode and the functional layer may be formed by a dry process before the formation of the layer that includes a light-emitting substance whereas the layer that includes a light-emitting substance, the functional layer stacked thereover, and the second electrode may be formed by a wet process. Needless to say, this embodiment is not limited to this, and the light-emitting element can be formed by appropriate selection from a wet method and a dry method depending on a material to be used, necessary film thickness, and the interface state.

In this embodiment, the light-emitting element is formed over a substrate made of glass, plastic or the like. A plurality of such light-emitting elements are formed over one substrate, whereby a passive matrix light-emitting device is formed. In addition, for example, a thin film transistor (TFT) may be formed over a substrate formed of glass, plastic, or the like, and a light-emitting element may be formed over an electrode electrically connected to the TFT. Thus, an active matrix light-emitting device in which the TFT controls the drive of the light-emitting element can be formed. Note that there is no particular limitation on the structure of the TFT. Either a staggered TFT or an inverted staggered TFT may be employed. In addition, crystallinity of a semiconductor used for the TFT is not particularly limited either; an amorphous semiconductor or a crystalline semiconductor may be used. In addition, a driver circuit formed over a TFT substrate may be formed using n-channel and p-channel TFTs, or using either n-channel or p-channel TFTs.

Further, the heterocyclic compounds described in Embodiment 1 each have a wide band gap and are bipolar materials which have a high electron-transporting property and a high hole-transporting property. Accordingly, with the use of any of the heterocyclic compounds described in Embodiment 1 for a light-emitting element, the light-emitting element can have a good carrier balance.

Furthermore, with the use of any of the heterocyclic compounds described in Embodiment 1, a highly efficient light-emitting device and a highly efficient electronic appliance can be obtained.

Embodiment 3

Figure 3A:
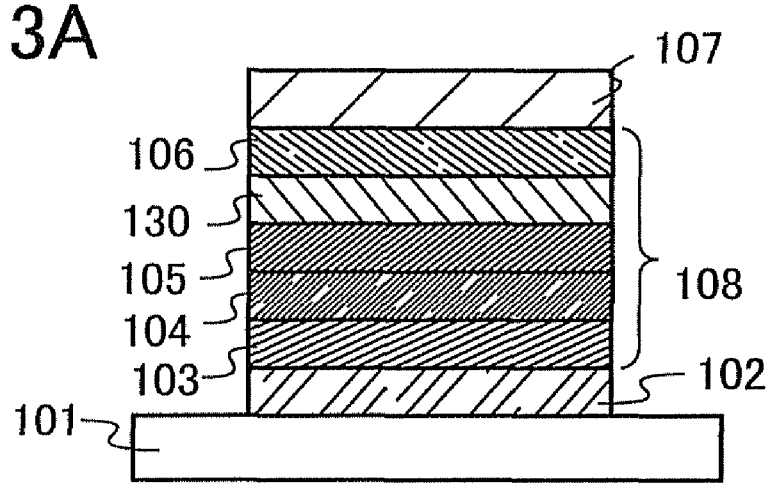
FIGS. 3A and 3B each illustrate a light-emitting element according to an embodiment of the present invention.
Figure 3B:
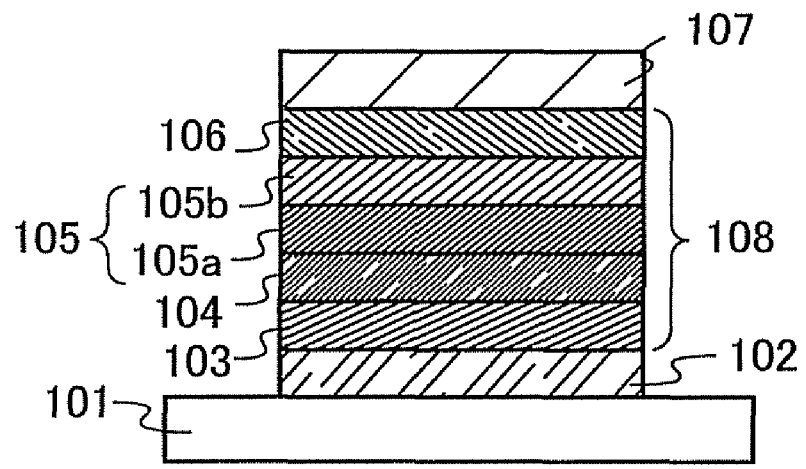

In this embodiment, light-emitting elements having structures that are different from those of the light-emitting elements described in Embodiment 2 will be described with reference to FIGS. 3A and 3B.

A layer for controlling transport of electron carriers may be provided between an electron-transporting layer and a light-emitting layer. In FIG. 3A, a structure in which a layer 130 for controlling transport of electron carriers is provided between the fourth layer 106 that is an electron-transporting layer and the third layer 105 that is a light-emitting layer (also referred to as the light-emitting layer 105). This layer for controlling transport of electron carriers is formed by adding a small amount of substance having a high electron-trapping property to a material having a high electron-transporting property described above, or alternatively, by adding a material having a low LUMO (lowest unoccupied molecular orbital) energy level and a hole-transporting property to a material having a high electron-transporting property. By suppressing transport of electron carriers, the carrier balance can be adjusted. Such a structure is very effective in suppressing problems (e.g., shortening of element lifetime) caused when electrons pass through the third layer 105.

As another structure, the light-emitting layer 105 may include a plurality of layers which are two or more layers. FIG. 3B illustrates an example in which the light-emitting layer 105 includes a plurality of layers which are two layers: a first light-emitting layer 105a and a second light-emitting layer 105b.

For example, when the first light-emitting layer 105a and the second light-emitting layer 105b are stacked in this order from the side of the second layer 104 which is a hole-transporting layer to form the light-emitting layer 105, a structure in which a substance having a hole-transporting property is used as the host material of the first light-emitting layer 105a and a substance having an electron-transporting property is used as the host material of the second light-emitting layer 105b may be employed.

Any of the heterocyclic compounds described in Embodiment 1 can be used alone for a light-emitting layer or as a host or even as a dopant.

In the case where any of the heterocyclic compounds described in Embodiment 1 is used as a host, light emission from a dopant which is a light-emitting substance can be obtained with a structure in which the dopant which is the light-emitting substance is dispersed in the heterocyclic compound described in Embodiment 1.

On the other hand, in the case where any of the heterocyclic compounds described in Embodiment 1 is used as a dopant, light emission from the heterocyclic compound described in Embodiment 1 can be obtained with a structure in which the heterocyclic compound described in Embodiment 1 is added to a layer formed using a material (a host) which has a larger band gap than the heterocyclic compound described in Embodiment 1.

Further, the heterocyclic compounds described in Embodiment 1 are bipolar substances each have a hole-transporting property and an electron-transporting property. Therefore, in the case of utilizing the hole-transporting property, the heterocyclic compound can be used for the first light-emitting layer 105a, or in the case of utilizing the electron-transporting property, any of the heterocyclic compounds can be used for the second light-emitting layer 105b. In the case where any of the heterocyclic compounds described in Embodiment 1 is used alone for the light-emitting layer or as a host material, which of the first light-emitting layer 105a having a hole-transporting property and the second light-emitting layer 105b having an electron-transporting property includes the heterocyclic compound may depend on the carrier-transporting property of the heterocyclic compound.

Note that this embodiment can be combined with any of the other embodiments, as appropriate.

Embodiment 4

In this embodiment, an embodiment of a light-emitting element having a structure in which a plurality of light-emitting units (EL layers) are stacked (hereinafter referred to as a stack element) will be described with reference to FIG. 4. This light-emitting element is a light-emitting element including a plurality of light-emitting units between a first electrode and a second electrode.

Figure 4:
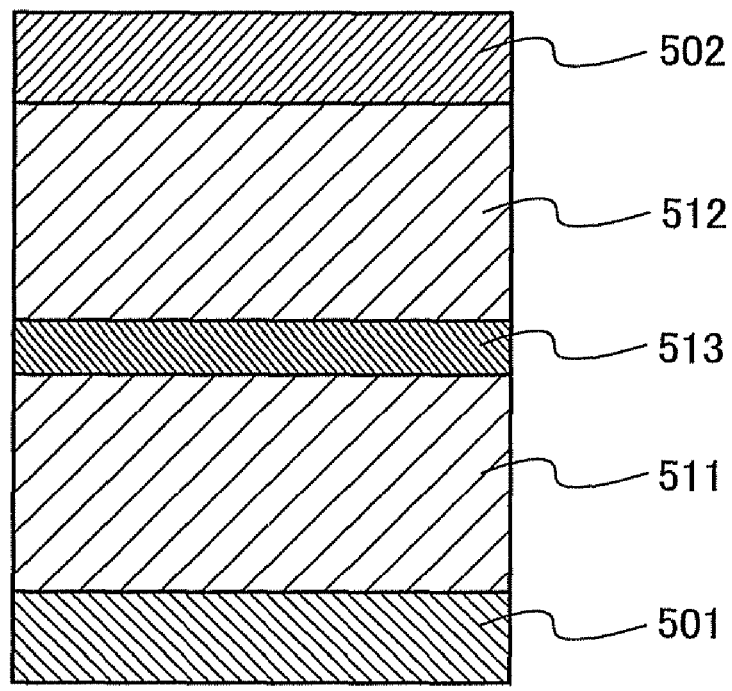
FIG. 4 illustrates a light-emitting element according to an embodiment of the present invention.

In FIG. 4, a first light-emitting unit 511 and a second light-emitting unit 512 are stacked between a first electrode 501 and a second electrode 502. Electrodes similar to those described in Embodiment 2 can be applied to the first electrode 501 and the second electrode 502. Alternatively, the structures of the first light-emitting unit 511 and the second light-emitting unit 512 may be the same or different from each other and can be similar to the structures described in Embodiment 2.

A charge generation layer 513 includes a composite material of an organic compound and metal oxide. This composite material of an organic compound and metal oxide corresponds to the composite material described in Embodiment 2 and includes an organic compound and metal oxide such as $V_2O_5$, $MoO_3$, or $WO_3$. As the organic compound, any of various compounds such as an aromatic amine compound, a carbazole derivative, aromatic hydrocarbon, and a macromolecular compound (including oligomer and dendrimer) can be used. Any of the heterocyclic compounds described in Embodiment 1 may be used. Note that as the organic compound, it is preferable to use the organic compound which has a hole-transporting property and has a hole mobility of $10^{-6}$ $cm^2/Vs$ or higher. The composite material of the organic compound and the metal oxide can achieve low-voltage driving and low-current driving because of the superior carrier-injecting property and the superior carrier-transporting property.

Note that the charge generation layer 513 may be formed by combination of the composite material of the organic compound and the metal oxide with another material. For example, a layer that includes the composite material of the organic compound and the metal oxide may be combined with a layer that includes a compound of a substance selected from substances having an electron-donating property and a compound having a high electron-transporting property. Moreover, a layer that includes the composite material of the organic compound and the metal oxide may be combined with a transparent conductive film.

In any case, the charge generation layer 513 interposed between the first light-emitting unit 511 and the second light-emitting unit 512 may have any structure as long as electrons are injected to one of the light-emitting units and holes are injected to the other light-emitting unit when voltage is applied to the first electrode 501 and the second electrode 502.

Although this embodiment describes the light-emitting element having two light-emitting units, this embodiment can be applied also to a light-emitting element in which three or more light-emitting units are stacked. When the charge generation layer is provided between the pair of electrodes so as to partition the plurality of light-emitting units as in the case of the light-emitting element of this embodiment, the element can emit light in a high luminance region while current density is kept low. Since current density can be kept low, the element can have long lifetime.

Note that this embodiment can be combined with any of the other embodiments, as appropriate.

Embodiment 5

In this embodiment, a light-emitting device which is formed using any of the heterocyclic compounds described in the above embodiment will be described.

Figure 5A:
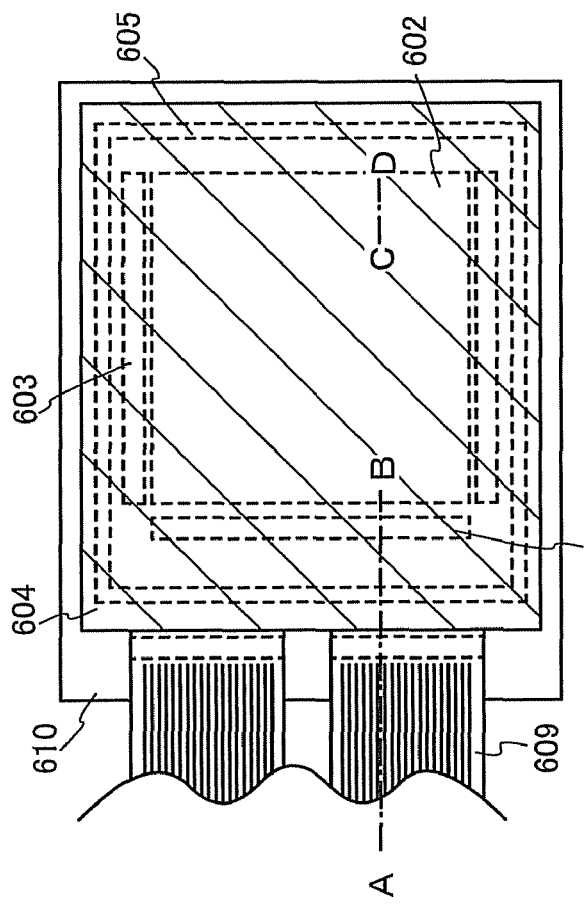
FIGS. 5A and 5B illustrate a light-emitting device according to an embodiment of the present invention.
Figure 5B:
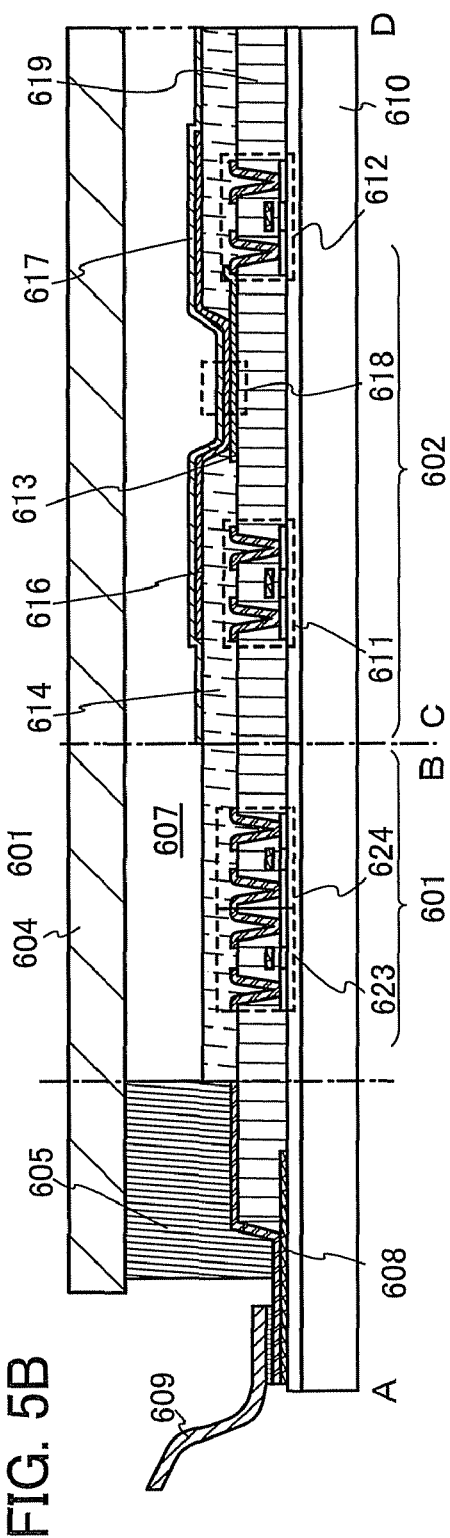

In this embodiment, a light-emitting device which is manufactured using any of the heterocyclic compounds described in Embodiment 1 will be described with reference to FIGS. 5A and 5B. Note that FIG. 5A is a top view of a light-emitting device, and FIG. 5B is a cross-sectional view taken along lines A-B and C-D of FIG. 5A. A reference numeral 601 shown by a dotted line denotes a driver circuit portion (source driver circuit); 602, a pixel portion; and 603, a driver circuit portion (gate driver circuit). Moreover, a reference numeral 604 denotes a sealing substrate; 605, a sealing material; and 607, a space surrounded by the sealing material 605.

A lead wiring 608 is a wiring for transmitting signals to be input into the source driver circuit 601 and the gate driver circuit 603 and receiving signals such as a video signal, a clock signal, a start signal, and a reset signal from an FPC (flexible printed circuit) 609 serving as an external input terminal. Although only the FPC is illustrated here, a printed wiring board (PWB) may be attached to the FPC. The light-emitting device in this specification includes, in its category, not only the light-emitting device itself but also the light-emitting device provided with the FPC or the PWB.

Next, a cross-sectional structure is described with reference to FIG. 5B. The driver circuit portion and the pixel portion are formed over an element substrate 610. Here, the source driver circuit 601, which is the driver circuit portion, and one pixel of the pixel portion 602 are illustrated.

As the source driver circuit 601, a CMOS circuit is formed in which an n-channel TFT 623 and a p-channel TFT 624 are combined. Further, the driver circuit may be formed using any of various circuits including TFTs, such as a CMOS circuit, a PMOS circuit, or an NMOS circuit. Although a driver-integration type device in which a driver circuit is formed over a substrate is described in this embodiment, a driver circuit is not necessarily formed over the substrate but can be formed outside the substrate.

The pixel portion 602 is formed with a plurality of pixels including a switching TFT 611, a current controlling TFT 612, and a first electrode 613 electrically connected to a drain of the current controlling TFT 612. An insulator 614 is formed to cover the end portions of the first electrode 613. Here, the insulator 614 is formed using a positive type photosensitive acrylic resin film.

In order to improve the coverage, the insulator 614 is formed to have a curved surface with curvature at its upper or lower end portion. For example, in the case of using positive photosensitive acrylic for the insulator 614, only the upper end portion of the insulator 614 preferably has a curved surface with a radius of curvature of 0.2 μM to 3 μm. As the insulator 614, either a negative type which becomes insoluble in etchant by irradiation with light or a positive type which becomes soluble in etchant by irradiation with light can be used.

A layer 616 that includes a light-emitting substance and a second electrode 617 are formed over the first electrode 613. As a material used for the first electrode 613 which functions as an anode, a material having a high work function is preferably used. For example, a single layer of an ITO film, an indium tin oxide film that includes silicon, an indium oxide film that includes 2 wt % to 20 wt % of zinc oxide (ZnO), a titanium nitride film, a chromium film, a tungsten film, a Zn film, a Pt film, or the like, a stacked layer of a titanium nitride film and a film that mainly includes aluminum, a three-layer structure of a titanium nitride film, a film that mainly includes aluminum and a titanium nitride film, or the like can be used. The layered structure achieves low wiring resistance and favorable ohmic contact.

In addition, the layer 616 that includes a light-emitting substance is formed by any of a variety of methods such as an evaporation method using an evaporation mask, a droplet discharging method such as an inkjet method, a printing method, and a spin coating method. The layer 616 that includes a light-emitting substance includes any of the heterocyclic compounds described in Embodiment 1. Further, the layer 616 that includes a light-emitting substance may include another material such as a low molecular material or a macromolecular material (including an oligomer and a dendrimer).

As a material used for the second electrode 617 which is formed over the layer 616 that includes a light-emitting substance and functions as a cathode, a material having a low work function (Al, Mg, Li, Ca, an alloy or a compound thereof such as MgAg, MgIn, AlLi, LiF, or $CaF_2$, or the like) is preferably used. When light generated in the layer 616 that includes a light-emitting substance is transmitted through the second electrode 617, the second electrode 617 may be formed using a stack of a metal thin film with a reduced film thickness and a transparent conductive film (e.g., a film of ITO, indium oxide that includes 2 wt % to 20 wt % of zinc oxide, indium tin oxide that includes silicon or silicon oxide, or zinc oxide (ZnO)).

Further, a light-emitting element 618 is provided in the space 607 surrounded with the element substrate 610, the sealing substrate 604, and the sealing material 605 by attachment of the sealing substrate 604 and the element substrate 610 with the use of the sealing material 605. The space 607 may be filled with filler, and may be filled with an inert gas (such as nitrogen or argon), the sealing material 605, or the like.

An epoxy based resin is preferably used for the sealing material 605. A material used for these is desirably a material which does not transmit as much moisture or oxygen as possible. As a material for the sealing substrate 604, a plastic substrate made of fiberglass-reinforced plastics (FRP), polyvinyl fluoride (PVF), polyester, acrylic, or the like can be used, other than a glass substrate or a quartz substrate.

As described above, the light-emitting device formed using any of the heterocyclic compounds described in Embodiment 1 can be obtained.

Further, the heterocyclic compounds described in Embodiment 1 each have a wide band gap and are a bipolar material which has a high electron-transporting property and a high hole-transporting property. Accordingly, by using any of the heterocyclic compounds described in Embodiment 1 for a light-emitting element, the highly efficient light-emitting element can have a good carrier balance.

Further, by using any of the heterocyclic compounds described in Embodiment 1, a highly efficient light-emitting device can be obtained.

Figure 6A:
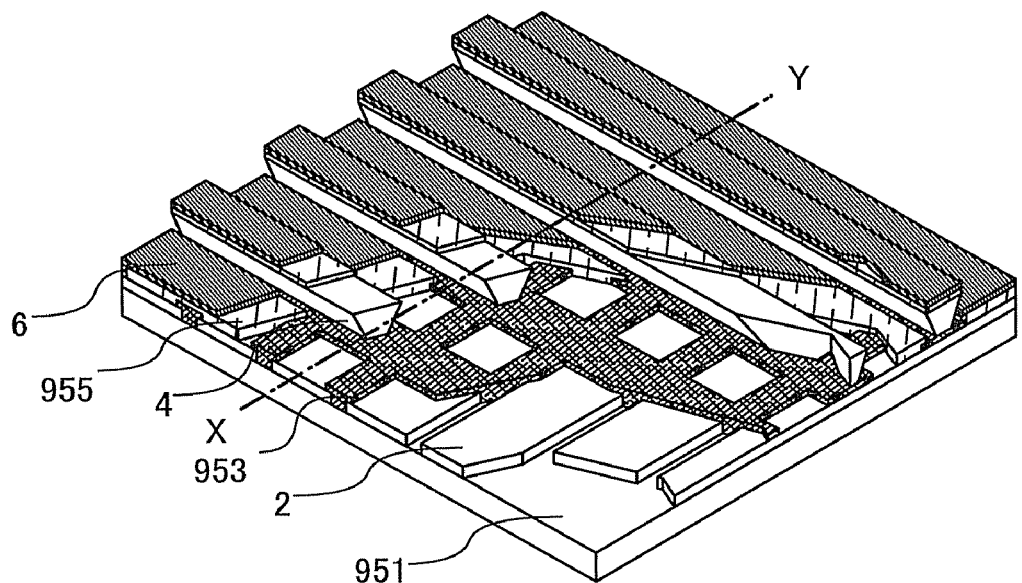
FIGS. 6A and 6B illustrate a light-emitting device according to an embodiment of the present invention.
Figure 6B:
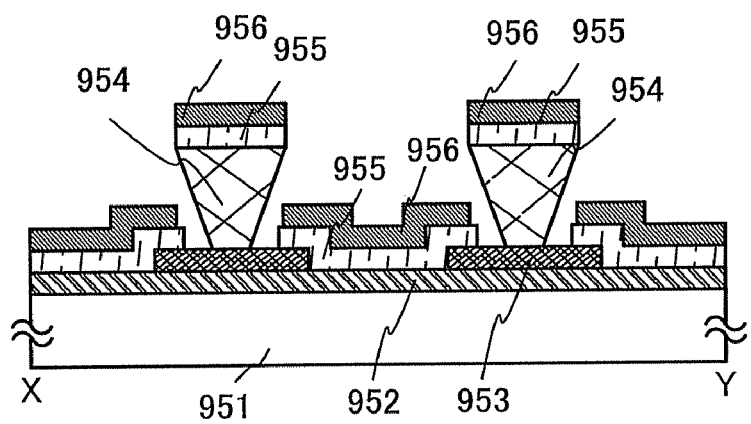

Although an active matrix light-emitting device which controls driving of a light-emitting element with a transistor is thus described in this embodiment, the light-emitting device may be a passive matrix light-emitting device. FIGS. 6A and 6B illustrate a passive matrix light-emitting device manufactured by application of the above embodiment. In FIGS. 6A and 6B, a layer 955 that includes a light-emitting substance is provided between an electrode 952 and an electrode 956 over a substrate 951. An edge portion of the electrode 952 is covered with an insulating layer 953. A partition layer 954 is provided over the insulating layer 953. The sidewalls of the partition layer 954 are aslope such that the distance between both sidewalls is gradually narrowed toward the surface of the substrate. In other words, a cross section taken in the direction of the short side of the partition layer 954 is trapezoidal, and the base of the cross-section (a side facing in the same direction as a plane direction of the insulating layer 953 and in contact with the insulating layer 953) is shorter than the upper side of the cross-section (a side facing in the same direction as the plane direction of the insulating layer 953 and not in contact with the insulating layer 953). By providing the partition layer 954 in this manner, defects of the light-emitting element due to static electricity or the like can be prevented. A light-emitting device with high reliability can be obtained also in the case of the passive-matrix light-emitting device by including the light-emitting element of the above embodiment.

Embodiment 6

In this embodiment, electronic appliances each include the light-emitting device of an embodiment of the present invention as a part will be described. The electronic appliances of this embodiment each include a display portion having high reliability, where any of the heterocyclic compounds described in Embodiment 1 is included.

Examples of the electronic appliances each having the light-emitting element formed with any of the heterocyclic compounds of Embodiment 1 include cameras such as video cameras or digital cameras, goggle type displays, navigation systems, audio reproducing devices (e.g., car audio components and audio components), computers, game machines, portable information terminals (e.g., mobile computers, cellular phones, portable game machines, and electronic books), and image reproducing devices provided with recording media (specifically, a device capable of reproducing recording media such as digital versatile discs (DVDs) and provided with a display device that can display the image). Specific examples of these electronic appliances are illustrated in FIGS. 7A to 7D.

Figure 7A:
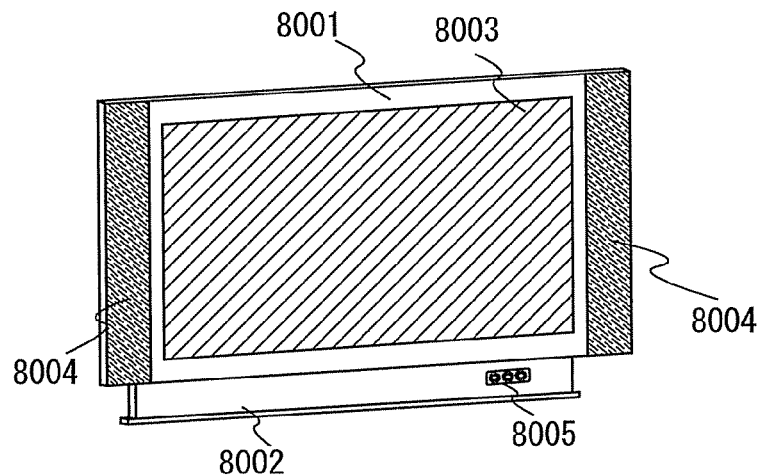
FIGS. 7A to 7D illustrate electronic appliances according to embodiments of the present invention.

FIG. 7A illustrates a display device according to this embodiment, which includes a housing 8001, a supporting base 8002, a display portion 8003, a speaker portion 8004, video input terminals 8005, and the like. Note that the display device includes all devices for displaying information, for example, for a personal computer, for receiving TV broadcasting, and for displaying an advertisement. In this display device, the display portion 8003 includes light-emitting elements similar to those described in Embodiment 2 or 3, which are arranged in matrix. A feature of each light-emitting element is high reliability. The display portion 8003 including the light-emitting elements has a similar feature. Therefore, in this display device, image quality hardly deteriorates, and reliability is improved. With such a feature, a circuit having a function of compensating for deterioration or power supply circuits in the display device can be significantly reduced or downsized; accordingly, reduction in size and weight of the housing 8001 or the supporting base 8002 can be achieved.

Figure 7B:
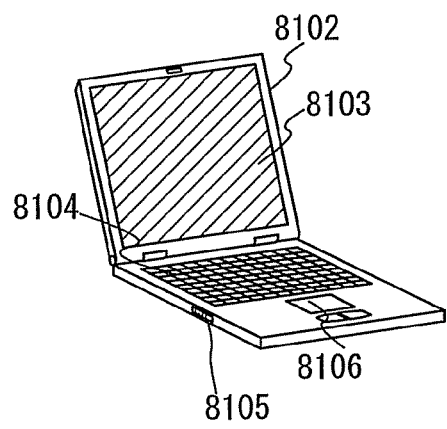

FIG. 7B illustrates a computer according to this embodiment, which includes a housing 8102, a display portion 8103, a keyboard 8104, an external connection port 8105, a pointing device 8106, and the like. In this computer, the display portion 8103 includes light-emitting elements similar to those described in Embodiment 2 or 3, which are arranged in matrix. A feature of each light-emitting element is high reliability. The display portion 8103 including the light-emitting elements has a similar feature. Therefore, in this computer, image quality hardly deteriorates, and reliability is improved. With such a feature, a circuit having a function of compensating for deterioration or power supply circuits in the computer can be significantly reduced or downsized; accordingly, reduction in size and weight of the computer can be achieved.

Figure 7C:
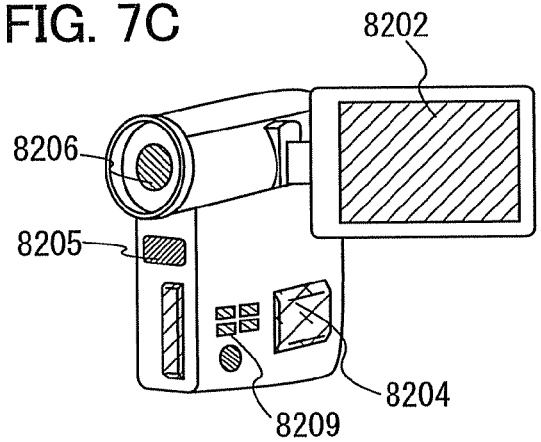

FIG. 7C illustrates a video camera according to this embodiment, which includes a display portion 8202, an external connecting port 8204, a remote control receiving portion 8205, an image receiving portion 8206, an operation key 8209, and the like. In this video camera, the display portion 8202 includes light-emitting elements similar to those described in Embodiment 2 or 3, which are arranged in matrix. A feature of each light-emitting element is high reliability. The display portion 8202 including the light-emitting elements has a similar feature. Therefore, in this video camera, image quality hardly deteriorates, and reliability is improved. With such a feature, a circuit having a function of compensating for deterioration or power supply circuits in the video camera can be significantly reduced or downsized; accordingly, reduction in size and weight of the video camera can be achieved. Since high image quality and reduction in size and weight are achieved in the video camera of this embodiment, a product suitable for being carried can be provided.

Figure 7D:
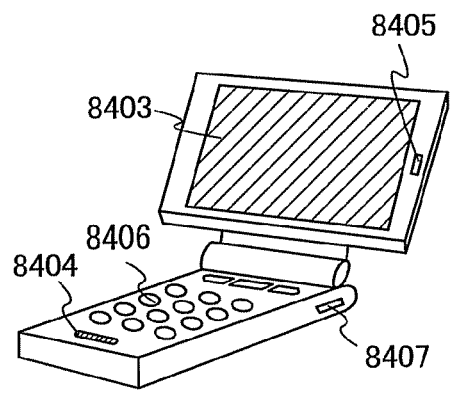

FIG. 7D illustrates a cellular phone according to this embodiment, which includes a display portion 8403, an audio input portion 8404, an audio output portion 8405, operation keys 8406, an external connection port 8407, and the like. In this cellular phone, the display portion 8403 includes light-emitting elements similar to those described in Embodiment 2 or 3, which are arranged in matrix. A feature of each light-emitting element is high reliability. The display portion 8403 including the light-emitting elements has a similar feature. Therefore, in this cellular phone, image quality hardly deteriorates, and reliability is improved. With such a feature, a circuit having a function of compensating for deterioration or power supply circuits in the cellular phone can be significantly reduced or downsized; accordingly, reduction in size and weight of the cellular phone can be achieved. In the cellular phone of this embodiment, high image quality and the reduction in size and weight are achieved; thus, a product that is suitable for being carried can be provided.

From the above, the application range of the light-emitting device described in above embodiment is so wide that the light-emitting device can be applied to electronic appliances of a variety of fields. With the use of any of the heterocyclic compounds described in Embodiment 1, an electronic appliance including a highly reliable display portion can be provided.

The light-emitting device described in the above embodiment can also be used as a lighting device. An embodiment in which the above-described light-emitting element is used as a lighting device will be described with reference to FIG. 8.

Figure 8:
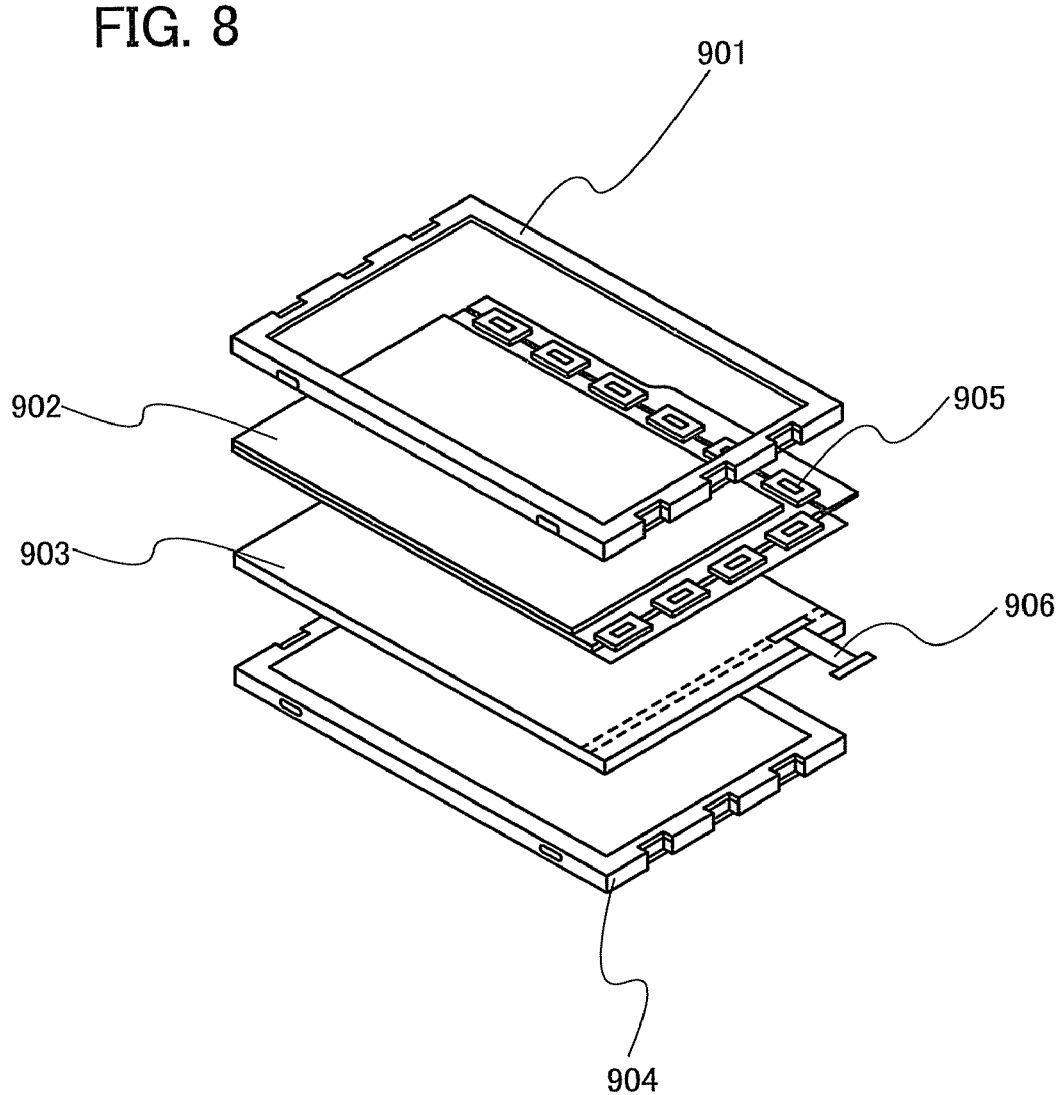
FIG. 8 illustrates an electronic appliance according to an embodiment of the present invention.

FIG. 8 illustrates an example of a liquid crystal display device using, as a backlight, the light-emitting device to which the above embodiment is applied. The liquid crystal display device illustrated in FIG. 8 includes a chassis 901, a liquid crystal layer 902, a backlight 903, and a chassis 904, and the liquid crystal layer 902 is connected to a driver IC 905. The light-emitting device described in the above embodiment is used as the backlight 903, and current is supplied through a terminal 906.

By using the light-emitting device described in the above embodiment as a backlight of a liquid crystal display device, the backlight can have high reliability. The light-emitting device described in the above embodiment is a lighting device with plane light emission, and can have a large area. Therefore, the backlight can have a large area, and thus a liquid crystal display device having a large area can be realized. Furthermore, the light-emitting device described in the above embodiment has a thin shape, and thus a thin shape of a display device can also be realized.

Figure 9:
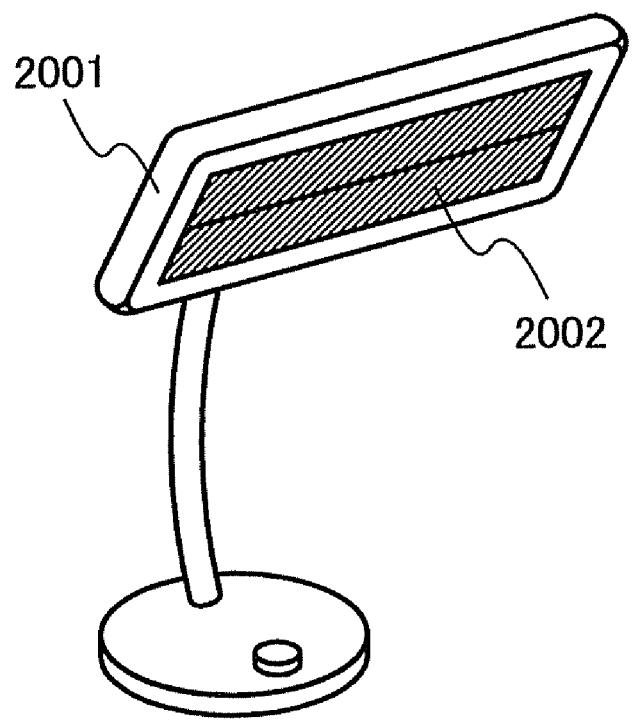
FIG. 9 illustrates a lighting device according to an embodiment of the present invention.

FIG. 9 illustrates an example in which a light-emitting device to which the above embodiment is applied is used as a desk lamp that is one of lighting devices. The desk lamp illustrated in FIG. 9 has a housing 2001 and a light source 2002, and the light-emitting device of the above embodiment is used as the light source 2002. Since the light-emitting device of the above embodiment is highly reliable, the desk lamp also has high reliability.

Figure 10:
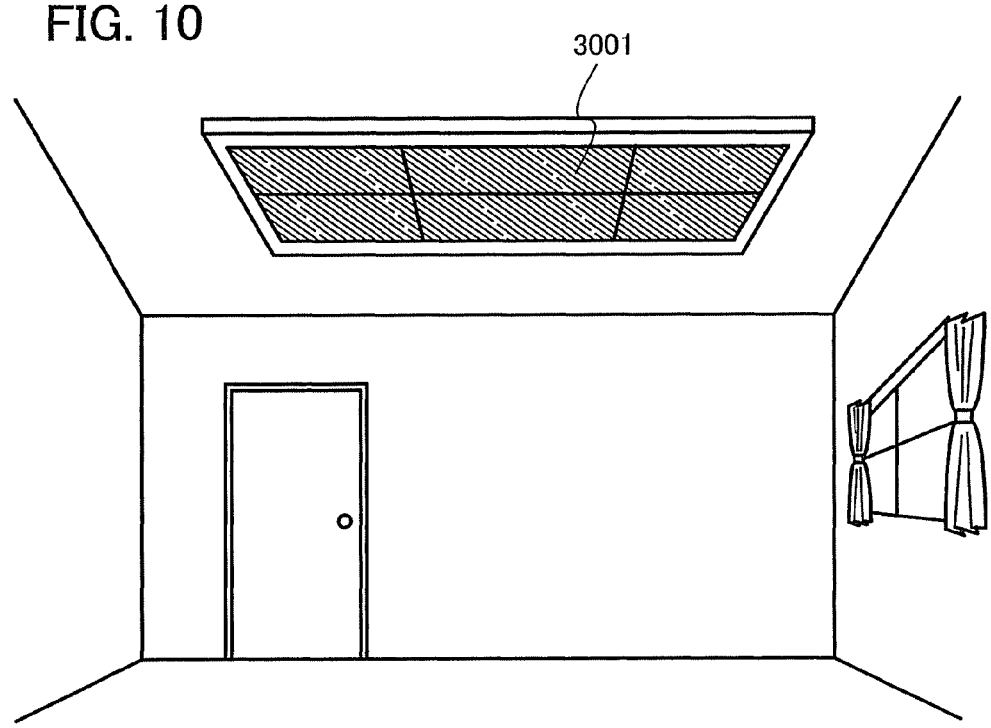
FIG. 10 illustrates a lighting device according to an embodiment of the present invention.

FIG. 10 is an example in which the light-emitting device according to the above embodiment is used as an indoor lighting device 3001. Since the light-emitting device of the above embodiment is highly reliable, the lighting device 3001 can have high reliability. Since the light-emitting device described in the above embodiment can be increased in area, the light-emitting device can be used as a lighting device having a large area. Further, since the light-emitting device of the above embodiment is thin, the light-emitting device of the above embodiment can be used as a lighting device with a thinner shape.

Example 1

In this example, an example in which 9-[4'''-(3,5-diphenyl-1H-1,2,4-triazol-1-yl)-[1,1':2',1'':2'',1''']quatelphenyl-4-yl]-9H-carbazole (abbreviation: Z-CzPTAZ(1H)) represented by the structural formula (100) is synthesized will be described.

(100)

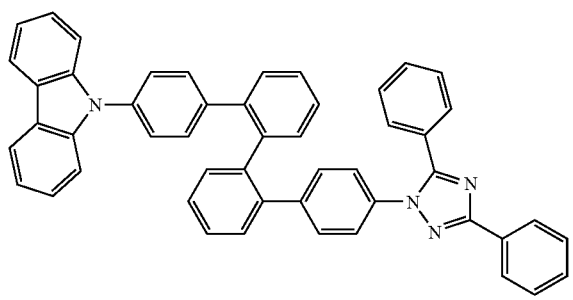

[Step 1]

This step is a step of synthesizing 9-(2'-bromobiphenyl-4-yl)-9H-carbazole. The step is shown in a synthetic scheme (E1-1) and will be detailed below.

(E1-1)

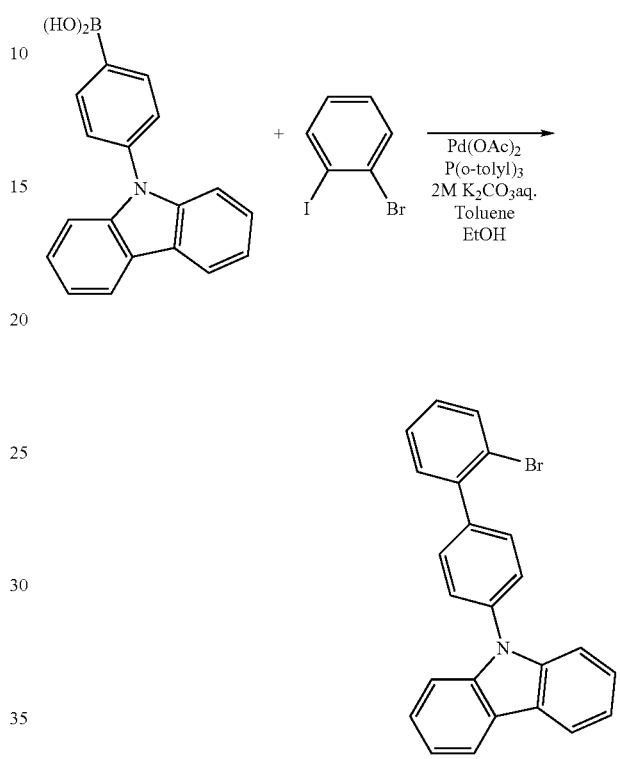

Into a 300 mL three-neck flask were put 15 g (52 mmol) of 4-(9H-carbazol-9-yl)phenylboronic acid, 22 g (78 mmol) of 2-bromoiodobenzene, 0.12 g (0.52 mmol) of palladium(II) acetate, and 1.1 g (3.7 mmol) of tri(o-tolyl)phosphine. After 90 mL of toluene, 15 mL of ethanol, 45 mL of a 2M aqueous solution of potassium carbonate were added to the mixture and this mixture was degassed while being stirred under reduced pressure, the atmosphere in the flask was replaced with nitrogen.

The mixture was stirred at 90° C. for 5 hours. After the stirring, toluene was added to the mixture and an organic layer was washed with a saturated aqueous solution of sodium carbonate and saturated saline in this order. After the washing, magnesium sulfate was added to the organic layer to dry the organic layer. After the drying, this mixture was subjected to suction filtration to obtain a filtrate. An oily substance obtained by concentrating the obtained filtrate was purified using silica gel column chromatography. The column chromatography was performed using hexane first as a developing solvent and then using a mixed solvent of hexane and ethyl acetate (hexane:ethyl acetate=20:1) as a developing solvent. The obtained fraction was concentrated and dried, so that 15 g of colorless oily substance was obtained in a yield of 74%.

[Step 2]

This step is a step of synthesizing 4'-(9H-carbazol-9-yl)biphenyl-2-boronic acid. The step is shown in a synthetic scheme (E1-2) and will be detailed below.

(E1-2)

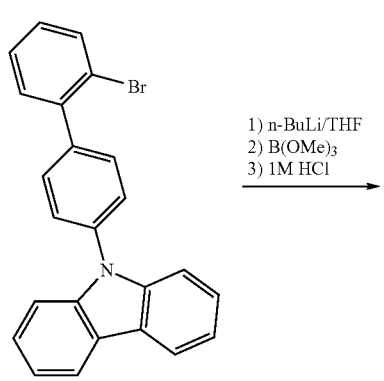

1) n-BuLi/THF
2) B(OMe)₃
3) 1M HCl

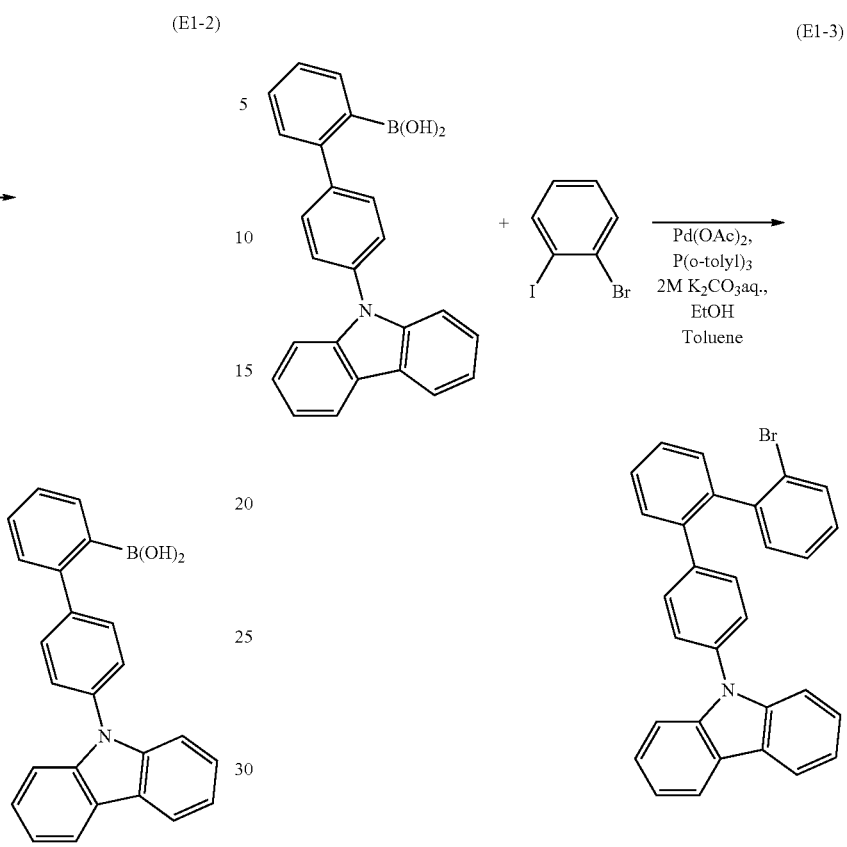

Into a 500 mL three-neck flask was put a mixed solution of 15 g (38 mmol) of 9-(2'-bromobiphenyl-4-yl)-9H-carbazole and 250 mL of tetrahydrofuran. After the solution was degassed while being stirred under reduced pressure, the atmosphere in the flask was replaced with nitrogen. The solution was stirred at −78° C. for 20 minutes. After the stirring, 29 mL (45 mmol) of hexane solution of 1.6 mol/L of n-butyllithium was dripped with a syringe, and the solution was stirred at −78° C. for 2 hours. After the stirring, 8.0 mL of trimethyl borate was added and the mixture was stirred at −78° C. for 1 hour, and then was stirred for 24 hours while the temperature of the mixture was being gradually brought back to a room temperature from −78° C.

After the stirring, 50 mL of 1M dilute hydrochloric acid was added to this solution, and the solution was stirred at a room temperature for 30 minutes. After the stirring, ethyl acetate was added to this mixture, and extraction was performed. The obtained extracted solution was washed with saturated saline. After the washing, magnesium sulfate was added to the organic layer to dry the organic layer. After the drying, this mixture was subjected to suction filtration to obtain a filtrate. A compound obtained by concentrating the obtained filtrate was recrystallized with a mixed solvent of toluene and hexane, so that 9.6 g of a powdery white solid was obtained in a yield of 70%.

[Step 3]

This step is a step of synthesizing 9-(2"-bromo-[1,1':2',1"]terphenyl-4-yl)-9H-carbazole. The step is shown in a synthetic scheme (E1-3) and will be detailed below.

Into a 200 mL three-neck flask were put 9.4 g (26 mmol) of 4'-(9H-carbazol-9-yl)biphenyl-2-boronic acid, 11 g (39 mmol) of 2-bromoiodobenzene, 0.058 g (0.26 mmol) of palladium(II) acetate, and 0.55 g (1.8 mmol) of tri(o-tolyl)phosphine. After that, 60 mL of toluene, 5 mL of ethanol, and 30 mL of a 2M aqueous solution of potassium carbonate were added to the solution. After this mixture was degassed while being stirred under reduced pressure, the atmosphere in the flask was replaced with nitrogen. The mixture was stirred at 95° C. for 5 hours in a nitrogen stream. After the stirring, toluene was added to the mixture, an organic layer and an aqueous layer were separated, and the organic layer was washed with a saturated aqueous solution of sodium carbonate and saturated saline in this order.

After the washing, magnesium sulfate was added to the organic layer to dry the organic layer. After the drying, the mixture was subjected to suction filtration through Celite (produced by Wako Pure Chemical Industries, Ltd., Catalog No. 531-16855), Florisil (produced by Wako Pure Chemical Industries, Ltd., Catalog No. 540-00135), and alumina, so that a filtrate was obtained. An oily substance obtained by concentrating the obtained filtrate was purified using silica gel column chromatography. The column chromatography was performed using hexane first as a developing solvent and then using a mixed solvent of hexane and toluene (hexane:toluene=2:1) as a developing solvent. The obtained fraction was concentrated and dried, so that 8.0 g of colorless oily substance was obtained in a yield of 65%.

[Step 4]

This step is a step of synthesizing 4"-(9H-carbazol-9-yl-[1,1':2',1"]terphenyl-2-boronic acid. The step is shown in a synthetic scheme (E1-4) and will be detailed below.

(E1-4)

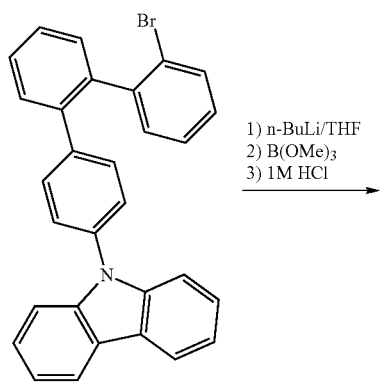

1) n-BuLi/THF
2) B(OMe)₃
3) 1M HCl
→

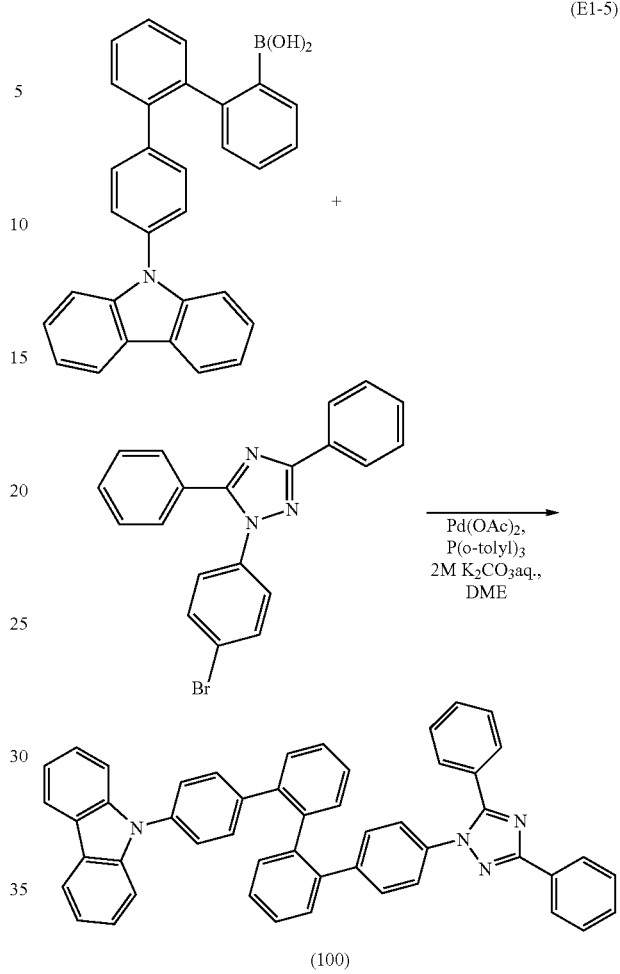

Into a 300 mL three-neck flask was put 8.0 g (17 mmol) of 9-(2''-bromo-[1,1':2',1'']terphenyl-4-yl)-9H-carbazole, 150 mL of tetrahydrofuran was added to the solution, and the solution was stirred. After this solution was degassed while being stirred under reduced pressure, the atmosphere in the flask was replaced with nitrogen. The solution was stirred at −78° C. for 20 minutes. Into the solution, 13 mL (20 mmol) of 1.6M n-butyllithium hexane solution was dripped with a syringe, and the solution was stirred at −78° C. for 2 hours. After the stirring, 3.8 mL (34 mmol) of trimethyl borate was added to the solution and the solution was stirred at −78° C. for 1 hour, and then was stirred for 24 hours while the temperature of the mixture was being gradually brought back to a room temperature from −78° C. After the stirring, 50 mL of 1M dilute hydrochloric acid was added to this solution, and the solution was stirred for 30 minutes at a room temperature.

After the stirring, the aqueous layer of this mixture was extracted with ethyl acetate. After the extracting, the organic layer was washed with saturated saline. After the washing, magnesium sulfate was added to the organic layer to dry the organic layer. After the drying, the mixture was subjected to suction filtration to obtain a filtrate. The obtained filtrate was concentrated and recrystallized with a mixed solvent of toluene and hexane, so that 4.0 g of a powdery white solid was obtained in a yield of 54%.

[Step 5]

This step is a step of synthesizing 9-[4'''-(3,5-diphenyl-1H-1,2,4-triazol-1-yl)-[1,1':2',1'':2'',1''']quatelphenyl-4-yl]-9H-carbazole (abbreviation: Z-CzPTAZ (1H)). The step is shown in a synthetic scheme (E1-5) and will be detailed below.

Into a 100 mL three-neck flask were put 1.2 g (2.7 mmol) of 4''-(9H-carbazol-9-yl)-[1,1':2',1'']terphenyl-2-boronic acid, 1.0 g (2.7 mmol) of 1-(4-bromophenyl)-3,5-diphenyl-1H-1,2,4-triazole, 6.0 mg (0.027 mmol) of palladium(II) acetate, and 0.056 g (0.19 mmol) of tri(o-tolyl)phosphine. After that, 15 mL of 1,2-dimethoxyethane (abbreviation: DME) and 7 mL of a 2M aqueous solution of potassium carbonate were added to the solution. After this mixture was degassed while being stirred under reduced pressure, the atmosphere in the flask was replaced with nitrogen. This mixture was stirred at 90° C. for 10 hours in a nitrogen stream.

After the stirring, toluene was added to the mixture, an organic layer and an aqueous layer were separated, and the organic layer was washed with water. After the washing, magnesium sulfate was added to the organic layer to dry the organic layer. After the drying, the mixture was subjected to suction filtration through Celite (produced by Wako Pure Chemical Industries, Ltd., Catalog No. 531-16855) to obtain a filtrate. An oily substance obtained by concentrating the obtained filtrate was purified using silica gel column chromatography. The column chromatography was performed using toluene first as a developing solvent and then using a mixed solvent of toluene and ethyl acetate (toluene:ethyl acetate=10:1) as a developing solvent. A compound which was obtained by concentrating the obtained fraction was purified using high performance liquid chromatography (HPLC). As the developing solvent, chloroform was used.

The compound which was obtained by concentrating the obtained fraction was recrystallized with a mixed solvent of toluene and hexane, so that 0.64 g of a powdery white solid was obtained in a yield of 35%.

0.64 g of the obtained white solid was sublimated and purified using a train sublimation method. The sublimation purification was performed in such a manner that heating was performed at 270° C. for 16 hours under reduced pressure of 2.9 Pa with a flow rate of argon at 5 mL/min. After sublimation purification, 0.51 g of the target substance was obtained in a yield of 80%.

By a nuclear magnetic resonance (NMR) method, this compound was confirmed to be 9-[4'''-(3,5-diphenyl-1H-1,2,4-triazol-1-yl)-[1,1':2',1":2",1'"]quatelphenyl-4-yl]-9H-carbazole (abbreviation: Z-CzPTAZ (1H)) which was the target compound.

$^1$H NMR data of the obtained compound is described below. $^1$H NMR (CDCl$_3$, 300 MHz): δ=6.76 (d, J=8.3 Hz, 2H), 6.84 (d, J=8.3 Hz, 2H), 7.14 (d, J=8.3 Hz, 2H), 7.20-7.59 (m, 24H), 8.13 (d, J=7.8 Hz, 2H), 8.18-8.23 (m, 2H)

Figure 11A:
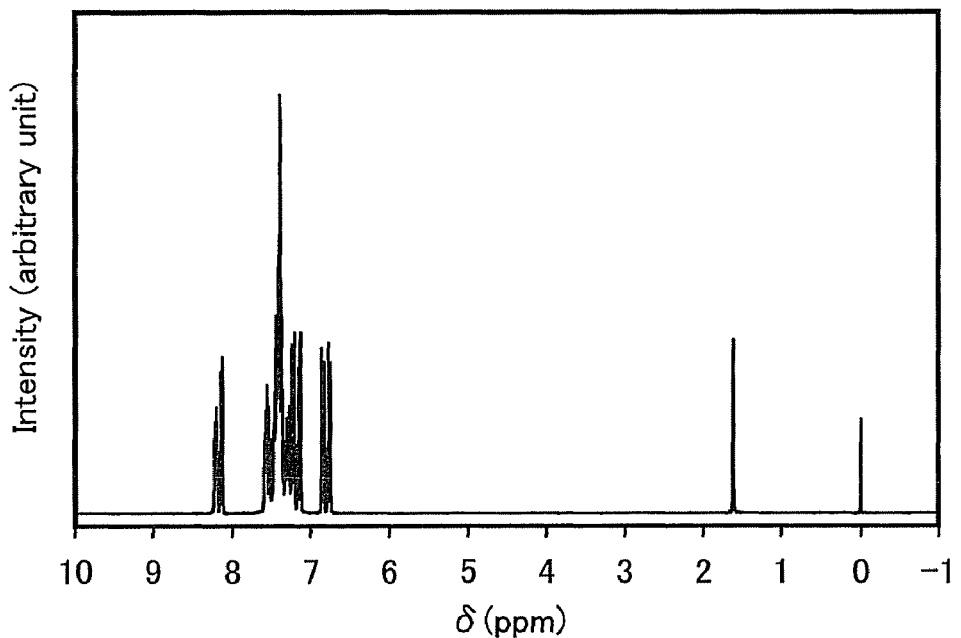
FIGS. 11A and 11B are $^1$H NMR charts of Z-CzPTAZ (1H)
Figure 11B:
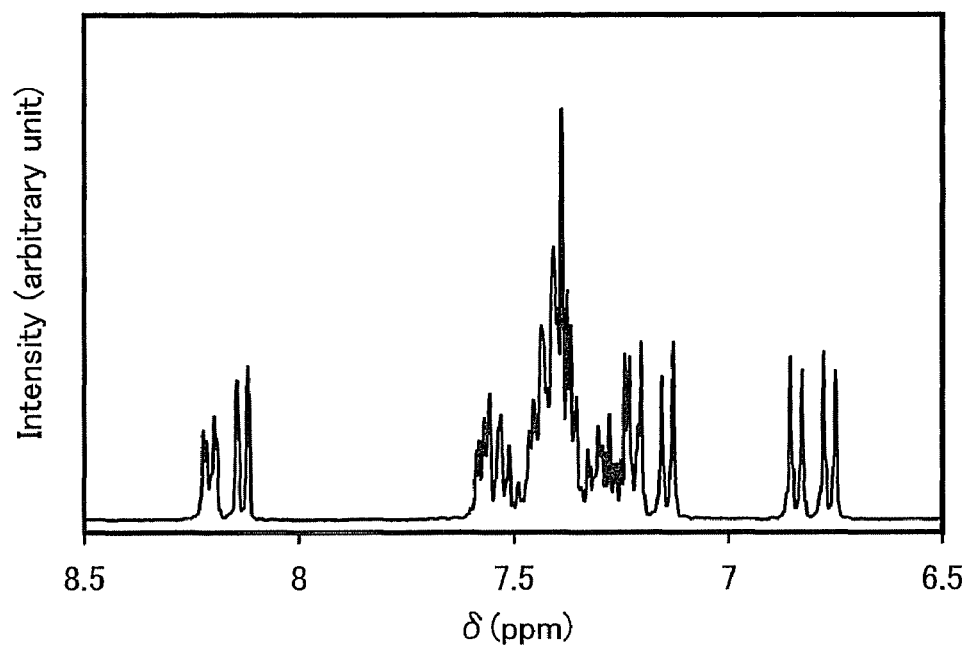

FIGS. 11A and 11B show $^1$H NMR charts. FIG. 11B is a chart showing an enlarged part of the range from 6.5 ppm to 8.5 ppm in FIG. 11A.

Figure 12A:
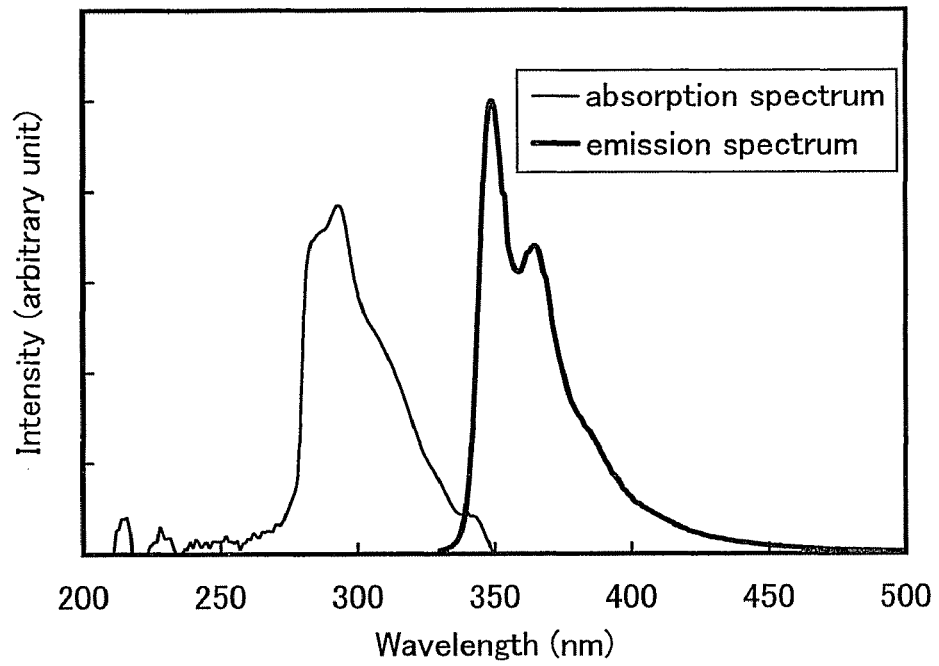
FIG. 12A shows an absorption spectrum and an emission spectrum of a toluene solution of Z-CzPTAZ(1H) and FIG. 12B shows an absorption spectrum and an emission spectrum of a thin film of Z-CzPTAZ(1H)
Figure 12B:
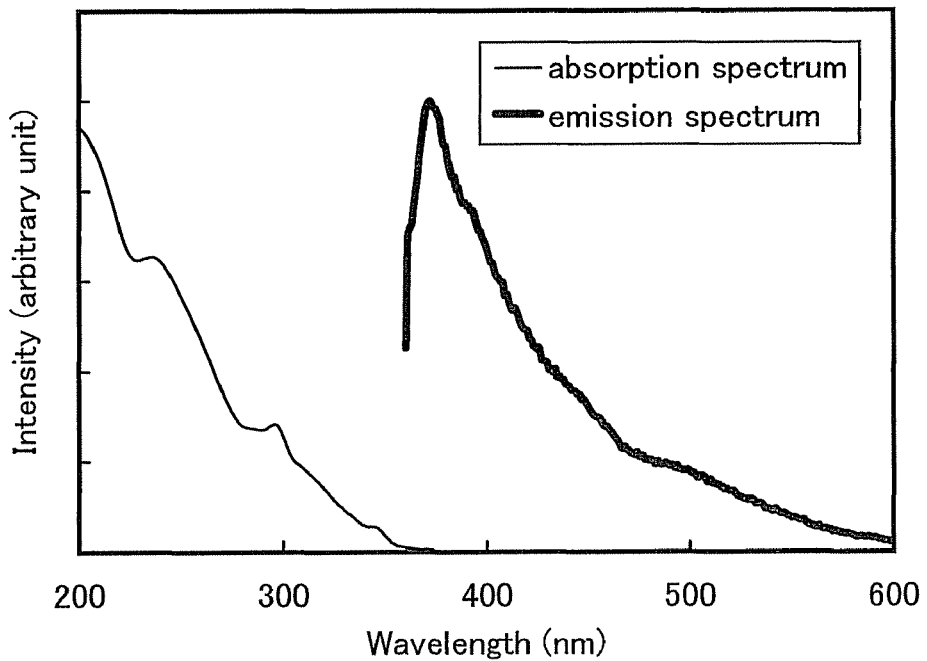

FIG. 12A shows an absorption spectrum and an emission spectrum of Z-CzPTAZ (1H) in a toluene solution. FIG. 12B shows an absorption spectrum and an emission spectrum of Z-CzPTAZ (1H) in a thin-film form. The absorption spectra were measured using a UV-visible spectrophotometer (V-550 manufactured by JASCO Corporation). To prepare samples, the solution was put in a quartz cell and the thin film was formed with evaporation over a quartz substrate, and measurements were performed. FIG. 12A shows the absorption spectrum of Z-CzPTAZ (1H) in the solution, which was obtained by subtracting the absorption spectra of the quartz cell and toluene from the raw absorption spectra. FIG. 12B shows the absorption spectrum of Z-CzPTAZ (1H) in the thin-film form, which was obtained by subtracting the absorption spectrum of the quartz substrate from the raw absorption spectra. In FIGS. 12A and 12B, the horizontal axis represents the wavelength (nm) and the vertical axis represents the intensity (arbitrary unit). In the case of the toluene solution, the absorption is observed at around 292 nm and 306 nm, and the emission wavelengths are 349 nm and 366 nm (the excitation wavelength: 321 nm). In the case of the thin film, the absorption is observed at around 236 nm, 296 nm, and 344 nm, and the maximum emission wavelength is 372 nm (the excitation wavelength: 344 nm).

Further, the HOMO level and LUMO level of Z-CzPTAZ (1H) in a state of a thin film were measured. The value of the HOMO level was obtained by converting the value of the ionization potential measured by using a photoelectron spectrometer (AC-2 manufactured by Riken Keiki Co., Ltd.) in the atmosphere into a negative value. An absorption edge was obtained from a Tauc plot assuming direct transition with the use of the absorption spectrum data of the thin film of Z-CzPTAZ (1H) shown in FIG. 12B, and the absorption edge was regarded as an optical energy gap and added to the value of the HOMO level, so that the value of the LUMO level was obtained. As a result, the HOMO level of Z-CzPTAZ (1H) is −5.88 eV, the energy gap is 3.51 eV, and the LUMO level is −2.37 eV.

Thus, it is found that Z-CzPTAZ (1H) has a large energy gap.

In addition, the optimal molecular structure of Z-CzPTAZ (1H) in the ground state was calculated using the density functional theory (DFT). In the DFT, the total energy is represented as the sum of potential energy, electrostatic energy between electrons, electronic kinetic energy, and exchange-correlation energy including all the complicated interactions between electrons. Also in the DFT, since an exchange-correlation interaction is approximated by a functional (a function of another function) of one electron potential represented in terms of electron density, calculations are performed with high accuracy at high speed. Here, B3LYP which was a hybrid functional was used to specify the weight of each parameter related to exchange-correlation energy. In addition, as a basis function, 6-311 (a basis function of a triple-split valence basis set using three contraction functions for each valence orbital) was applied to all the atoms. With the above basis function, for example, orbits of 1s to 3s are considered in the case of hydrogen atoms while orbits of 1s to 4s and 2p to 4p are considered in the case of carbon atoms. Furthermore, to improve calculation accuracy, the p function and the d function as polarization basis sets were respectively added to hydrogen atoms and atoms other than hydrogen atoms.

Note that Gaussian 03 was used as a quantum chemistry computational program. A high performance computer (Altix 4700 manufactured by SGI Japan, Ltd.) was used for the calculations.

Figure 24A:
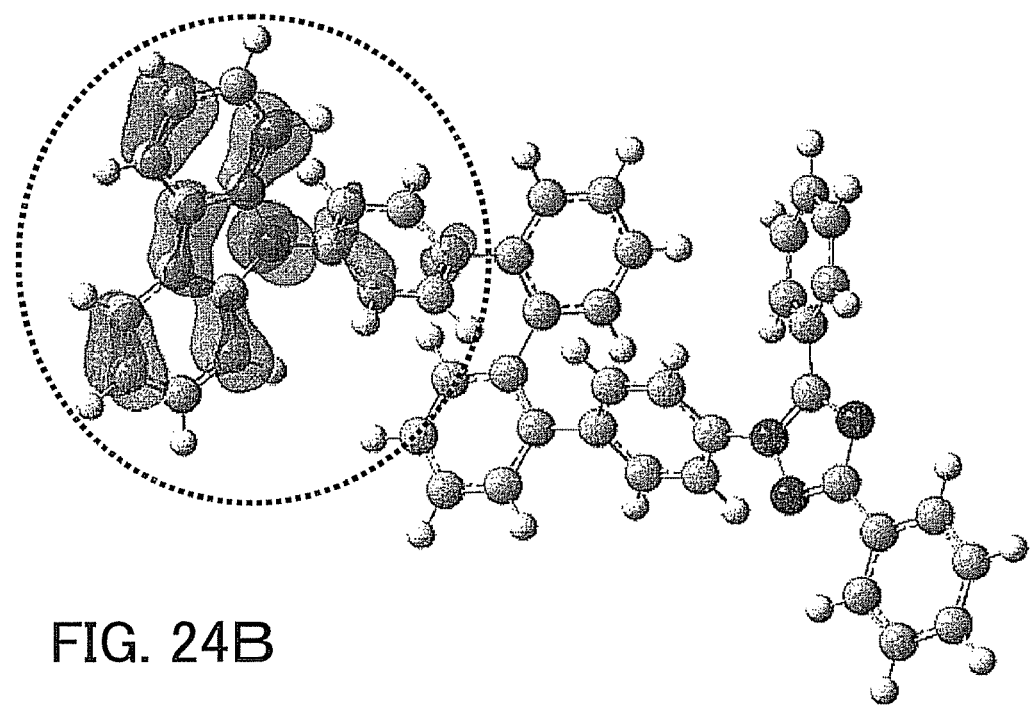
FIGS. 24A and 24B show the highest occupied molecular orbital and the lowest unoccupied molecular orbital of Z-CzPTAZ(1H) which were obtained with calculations.
Figure 24B:
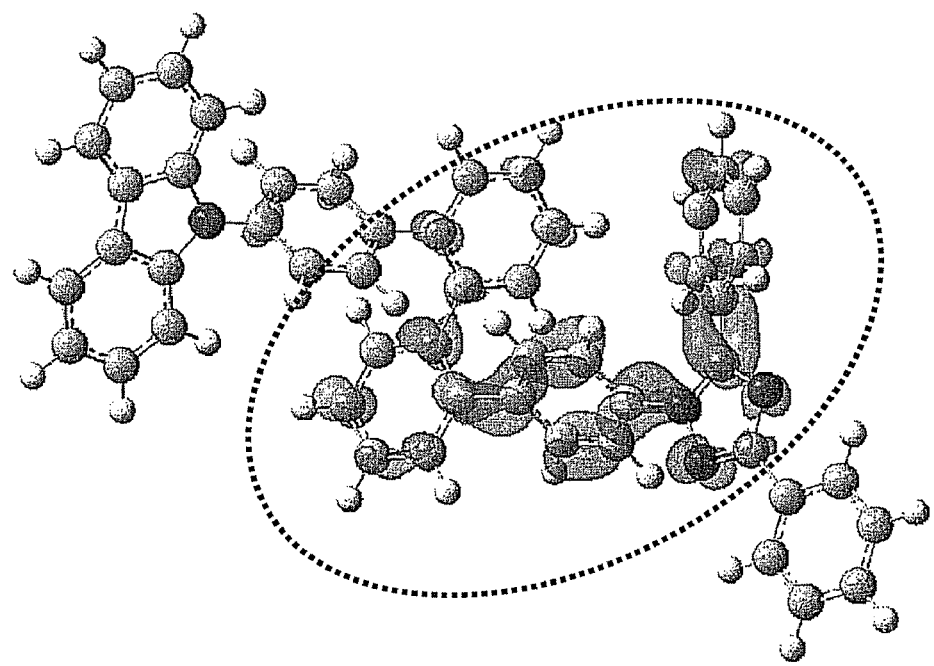

FIGS. 24A and 24B show respectively the highest occupied molecular orbital (HOMO) and the lowest unoccupied molecular orbital (LUMO) of an optimal molecular structure of Z-CzPTAZ (1H), which were obtained with the calculations and visualized using GaussView 4.1. FIG. 24A shows the highest occupied molecular orbital (HOMO), and FIG. 24B shows the lowest unoccupied molecular orbital (LUMO). In the drawings, the spheres represent atoms forming Z-CzPTAZ (1H) and cloud-like objects around atoms represent the highest occupied molecular orbital (HOMO) or the lowest unoccupied molecular orbital (LUMO).

From FIGS. 24A and 24B, it is found that the highest occupied molecular orbital of Z-CzPTAZ (1H) exists in the vicinity of carbazole and that the carbazolyl group largely contributes to the hole-transporting property of Z-CzPTAZ (1H). In addition, it is also found that the lowest unoccupied molecular orbital of Z-CzPTAZ (1H) exists in the vicinity of triazole and that the triazolyl group largely contributes to the electron-transporting property of Z-CzPTAZ (1H). Accordingly, it is found that Z-CzPTAZ (1H) is a bipolar material having an electron-transporting property and a hole-transporting property because a triazole skeleton which is a heteroaromatic ring having an electron-transporting property and a carbazole skeleton having a hole-transporting property are introduced into a molecule.

Example 2

In this example, an example in which 9-[4'''-(3,5-diphenyl-1H-pyrazol-1-yl)-4,1':2',1":2",1'"-quatelphenyl]-9H-carbazole (abbreviation: Z-CzPPz) represented by the structural formula (196) is synthesized will be described.

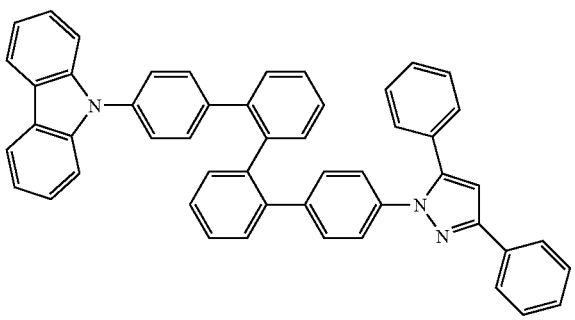

(196)

[Step 1]
This step is a step of synthesizing 9-[4'''-(3,5-diphenyl-1H-pyrazol-1-yl)-4,1':2',1'':2'',1'''-quatelphenyl]-9H-carbazole (abbreviation: Z-CzPPz). The step is shown in a synthetic scheme (E2-1) and will be detailed below.

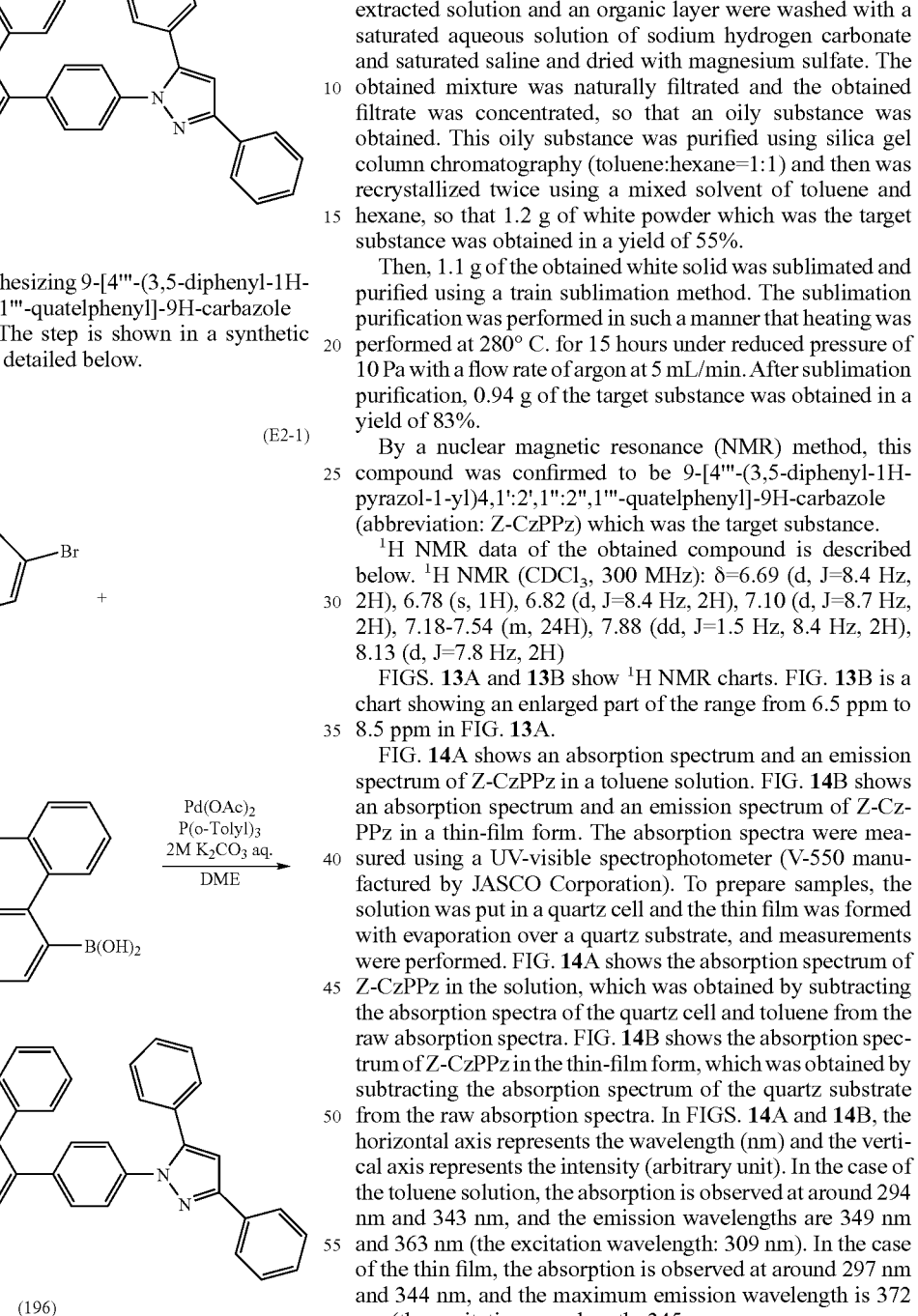

(E2-1)

(196)

Into a 300 mL three-neck flask were put 1.1 g (3.0 mmol) of 1-(4-bromophenyl)-3,5-diphenyl-1H-pyrazole, 1.3 g (3.1 mmol) of 4''-(9H-carbazol-9-yl)-[1,1':2',1'']terphenyl-2-boronic acid obtained through the steps 1 to 4 in Example 1, 0.19 g (0.62 mmol) of tri(o-tolyl)phosphine, 30 mL of 1,2-dimethoxyethane (abbreviation: DME), and 3 mL of a 2M aqueous solution of potassium carbonate. After this mixture was degassed while being stirred under reduced pressure, the atmosphere in the flask was replaced with nitrogen. Then, 33 mg (0.15 mmol) of palladium(II) acetate was added to this mixture, and the mixture was stirred at 80° C. for 6 hours in a nitrogen stream.

After the predetermined time passed, water was added to the mixture, and an aqueous layer was extracted. The extracted solution and an organic layer were washed with a saturated aqueous solution of sodium hydrogen carbonate and saturated saline and dried with magnesium sulfate. The obtained mixture was naturally filtrated and the obtained filtrate was concentrated, so that an oily substance was obtained. This oily substance was purified using silica gel column chromatography (toluene:hexane=1:1) and then was recrystallized twice using a mixed solvent of toluene and hexane, so that 1.2 g of white powder which was the target substance was obtained in a yield of 55%.

Then, 1.1 g of the obtained white solid was sublimated and purified using a train sublimation method. The sublimation purification was performed in such a manner that heating was performed at 280° C. for 15 hours under reduced pressure of 10 Pa with a flow rate of argon at 5 mL/min. After sublimation purification, 0.94 g of the target substance was obtained in a yield of 83%.

By a nuclear magnetic resonance (NMR) method, this compound was confirmed to be 9-[4'''-(3,5-diphenyl-1H-pyrazol-1-yl)4,1':2',1'':2'',1'''-quatelphenyl]-9H-carbazole (abbreviation: Z-CzPPz) which was the target substance.

$^1$H NMR data of the obtained compound is described below. $^1$H NMR (CDCl$_3$, 300 MHz): δ=6.69 (d, J=8.4 Hz, 2H), 6.78 (s, 1H), 6.82 (d, J=8.4 Hz, 2H), 7.10 (d, J=8.7 Hz, 2H), 7.18-7.54 (m, 24H), 7.88 (dd, J=1.5 Hz, 8.4 Hz, 2H), 8.13 (d, J=7.8 Hz, 2H)

Figure 13A:
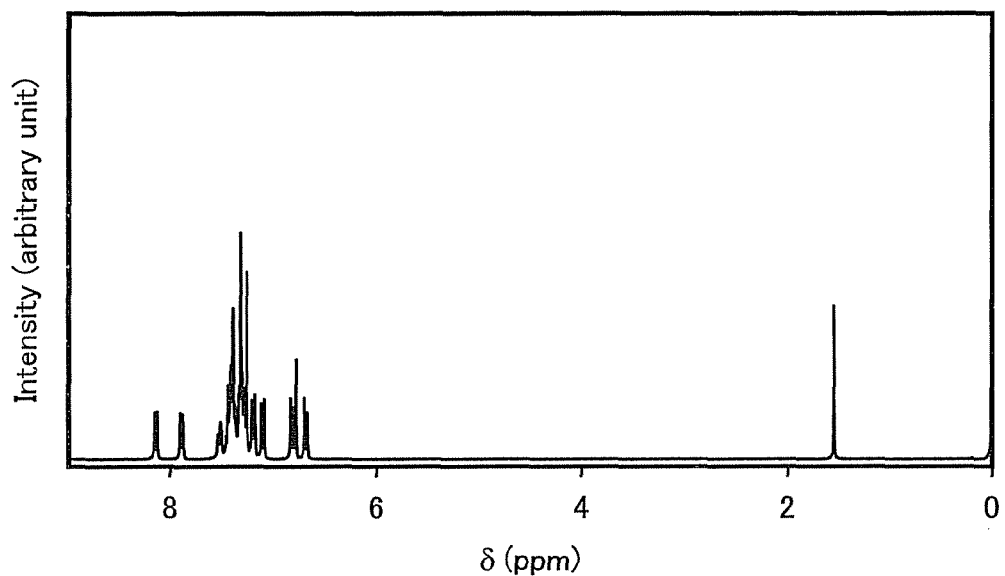
FIGS. 13A and 13B are $^1$H NMR charts of Z-CzPPz.
Figure 13B:
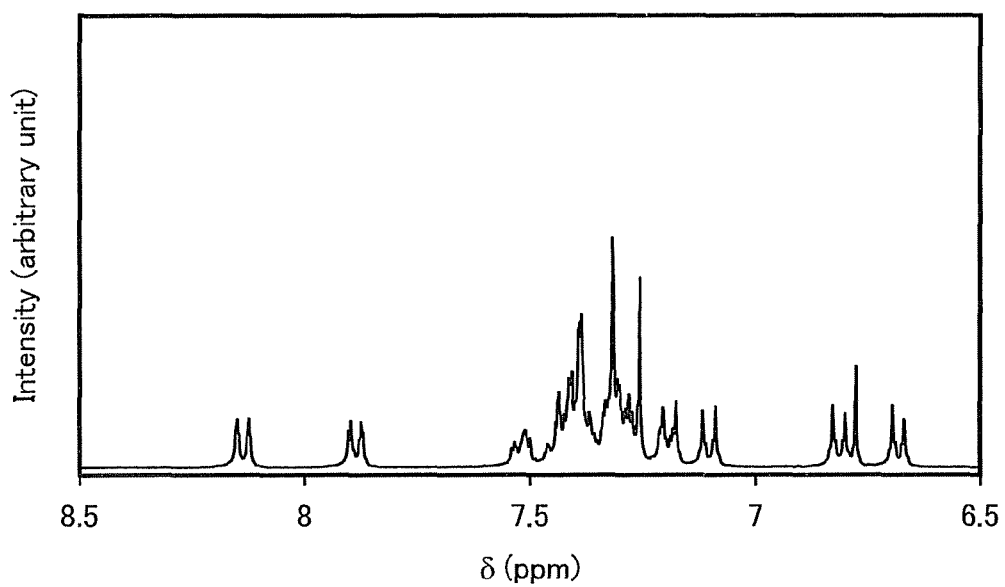

FIGS. 13A and 13B show $^1$H NMR charts. FIG. 13B is a chart showing an enlarged part of the range from 6.5 ppm to 8.5 ppm in FIG. 13A.

Figure 14A:
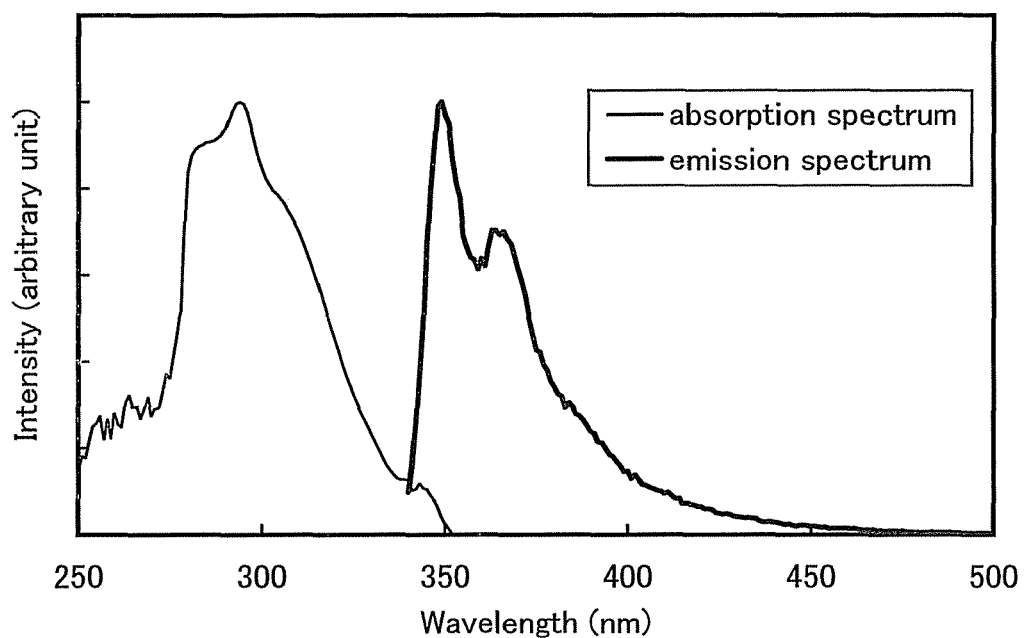
FIG. 14A shows an absorption spectrum and an emission spectrum of a toluene solution of Z-CzPPz and FIG. 14B shows an absorption spectrum and an emission spectrum of a thin film of Z-CzPPz.
Figure 14B:
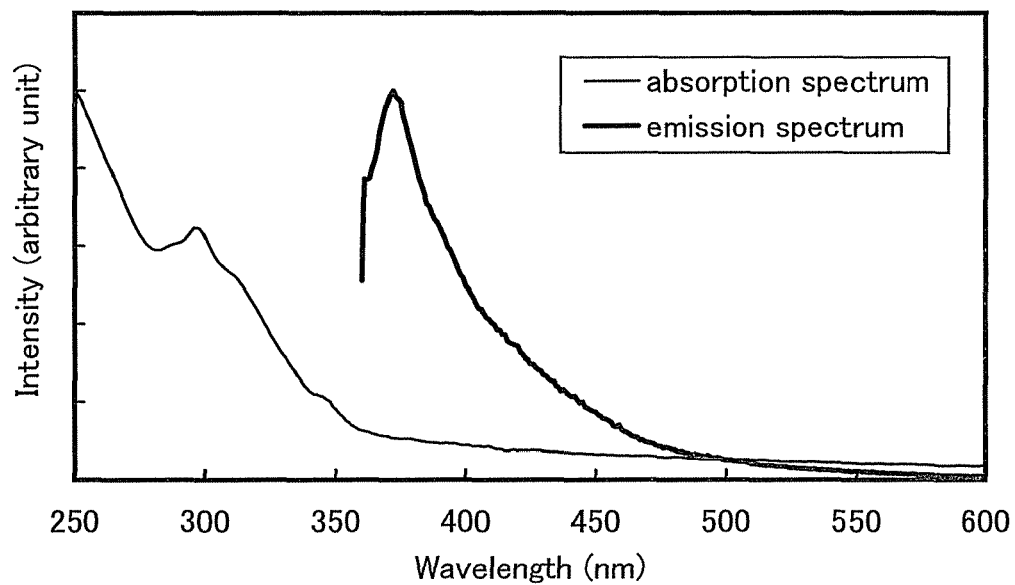

FIG. 14A shows an absorption spectrum and an emission spectrum of Z-CzPPz in a toluene solution. FIG. 14B shows an absorption spectrum and an emission spectrum of Z-CzPPz in a thin-film form. The absorption spectra were measured using a UV-visible spectrophotometer (V-550 manufactured by JASCO Corporation). To prepare samples, the solution was put in a quartz cell and the thin film was formed with evaporation over a quartz substrate, and measurements were performed. FIG. 14A shows the absorption spectrum of Z-CzPPz in the solution, which was obtained by subtracting the absorption spectra of the quartz cell and toluene from the raw absorption spectra. FIG. 14B shows the absorption spectrum of Z-CzPPz in the thin-film form, which was obtained by subtracting the absorption spectrum of the quartz substrate from the raw absorption spectra. In FIGS. 14A and 14B, the horizontal axis represents the wavelength (nm) and the vertical axis represents the intensity (arbitrary unit). In the case of the toluene solution, the absorption is observed at around 294 nm and 343 nm, and the emission wavelengths are 349 nm and 363 nm (the excitation wavelength: 309 nm). In the case of the thin film, the absorption is observed at around 297 nm and 344 nm, and the maximum emission wavelength is 372 nm (the excitation wavelength: 345

Further, the HOMO level and LUMO level of Z-CzPPz in a state of a thin film were measured. The value of the HOMO level was obtained by converting the value of the ionization potential measured by using a photoelectron spectrometer (AC-2 manufactured by Riken Keiki Co., Ltd.) in the atmosphere into a negative value. An absorption edge was obtained from a Tauc plot assuming direct transition with the use of the absorption spectrum data of the thin film of Z-CzPPz shown in FIG. 14B, and the absorption edge was regarded as an optical energy gap and added to the value of the HOMO level, so that the value of the LUMO level was obtained. As a result, the HOMO level of Z-CzPPz is −5.81 eV, the energy gap is 3.43 eV, and the LUMO level is −2.38 eV.

Thus, it is found that Z-CzPPz has a large energy gap.

Example 3

Figure 15:
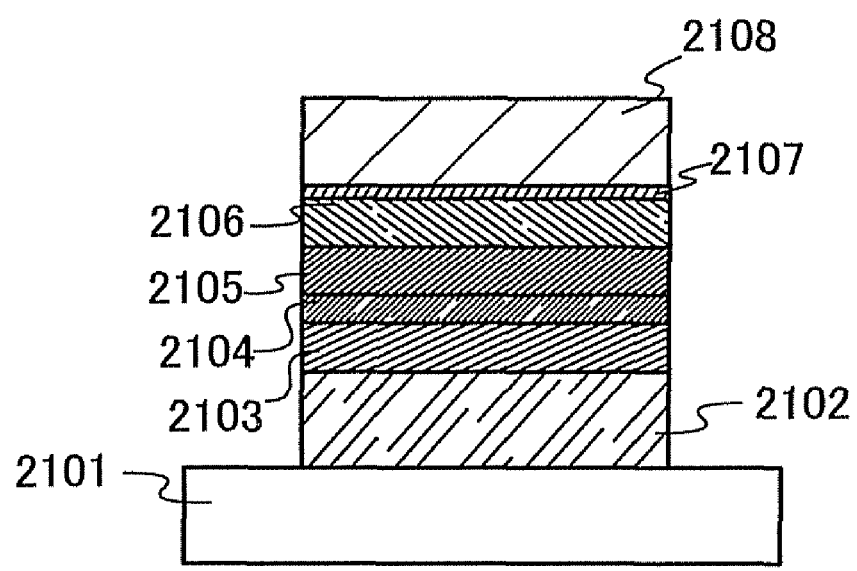
FIG. 15 illustrates a light-emitting element according to an example.

In this example, a light-emitting element according to an embodiment of the present invention will be described with reference to FIG. 15. Chemical formulae of materials used in this example are shown below.

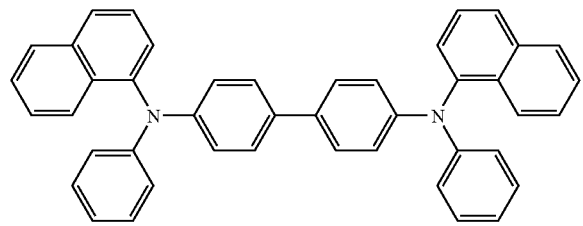

NPB

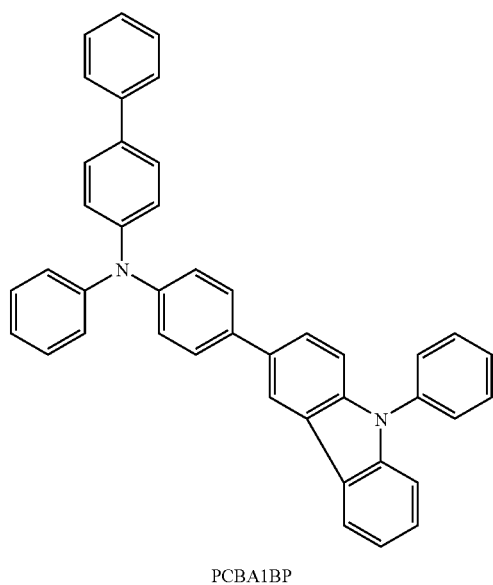

PCBA1BP

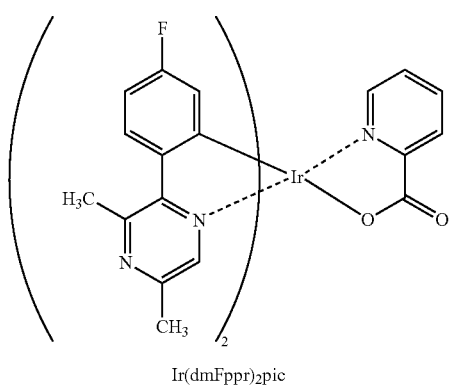

Ir(dmFppr)₂pic

-continued

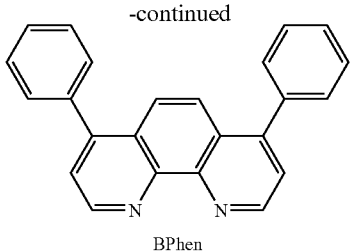

BPhen

A method for manufacturing a light-emitting element 1 of this example will be described below.

(Light-Emitting Element 1)

First, a film of indium tin oxide including silicon oxide was formed with a sputtering method over a glass substrate 2101 to form a first electrode 2102. The thickness was 110 nm and the electrode area was 2 mm×2 mm.

Next, the substrate having the first electrode was fixed to a substrate holder provided in a vacuum evaporation apparatus in such a way that a surface of the substrate, on which the first electrode was formed, faced downward, and then the pressure was reduced to about $10^{-4}$ Pa. Then, 4,4′-bis[N-(1-naphtyl)-N-phenylamino]biphenyl (abbreviation: NPB) and molybdenum(VI) oxide were co-evaporated over the first electrode 2102 with an evaporation method using resistance heating, whereby a layer that includes a composite material of an organic compound and an inorganic compound was formed as a first layer 2103. The thickness was 50 nm. The weight ratio of NPB to molybdenum(VI) oxide was adjusted to be 4:2 (=NPB:molybdenum(VI) oxide). Note that the co-evaporation method refers to an evaporation method in which evaporation is carried out from a plurality of evaporation sources at the same time in one treatment chamber.

Next, 4-phenyl-4′-(9-phenyl-9H-carbazol-3-yl)triphenylamine (abbreviation: PCBA1BP) was formed so as to have a thickness of 10 nm over the first layer 2103 to form a second layer 2104 as a hole-transporting layer.

Further, Z-CzPTAZ (1H) which is a heterocyclic compound synthesized in Example 1, PCBA1BP, and bis{2-(4-fluorophenyl)-3,5-dimethylpyrazinato}(picolinato)iridium (III) (abbreviation: Ir(dmFppr)₂pic) were co-evaporated, so that a third layer 2105 was formed as a light-emitting layer over the second layer 2104. Here, the weight ratio of Z-CzPTAZ (1H):PCBA1BP:Ir(dmFppr)₂pic was adjusted to be 1:0.2:0.1 (=Z-CzPTAZ (1H):PCBA1BP:Ir(dmFppr)₂pic). The thickness of the third layer 2105 was set to be 40 nm.

Then, Z-CzPTAZ (1H) which is a heterocyclic compound synthesized in Example 1 with a thickness of 10 nm and bathophenanthroline (abbreviation: BPhen) with a thickness of 20 nm were stacked in this order over the third layer 2105 with evaporation to form a fourth layer 2106 as an electron-transporting layer. Further, lithium fluoride (LiF) was deposited over the fourth layer 2106 to a thickness of 1 nm, whereby a fifth layer 2107 was formed as an electron-injecting layer. Lastly, aluminum was deposited to a thickness of 200 nm for a second electrode 2108 which is to serve as a cathode. Thus, the light-emitting element 1 of this example was obtained.

Note that, in the above evaporation process, evaporation was all performed with a resistance heating method.

Table 1 below shows the element structure of the light-emitting element 1.

TABLE 1

| | |
|---|---|
| second electrode 2108 | Al 200 nm |
| fifth layer 2107 | LiF 1 nm |
| fourth layer 2106 | BPhen 20 nm |
| | Z-CzPTAZ(1H) 10 nm |
| third layer 2105 | Z-CzPTAZ(1H):PCBA1BP:Ir(dmFppr)$_2$pic (=1:0.2:0.1) 40 nm |
| second layer | PCBA1BP 10 nm |
| first layer 2103 | NPB:MoOx(=4:2) 50 nm |
| first electrode 2102 | ITSO 110 nm |

The light-emitting element 1 thus obtained was sealed in a glove box under a nitrogen atmosphere without being exposed to the atmosphere. Then, the operating characteristic of the light-emitting element 1 was measured. Note that the measurement was carried out at room temperature (in an atmosphere kept at 25° C.).

Figure 16:
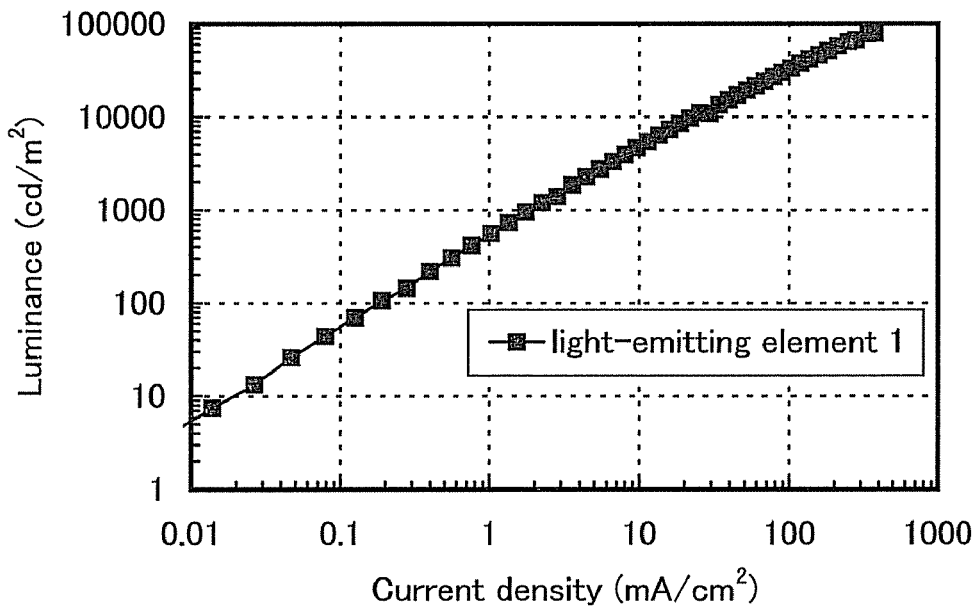
FIG. 16 shows current density-luminance characteristics of a light-emitting element 1.
Figure 17:
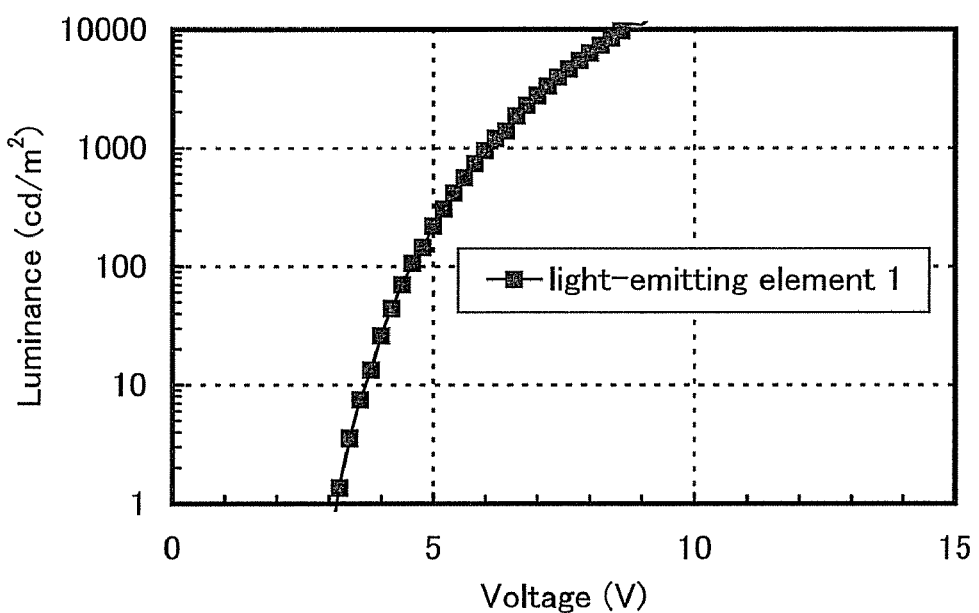
FIG. 17 shows voltage-luminance characteristics of the light-emitting element 1.
Figure 18:
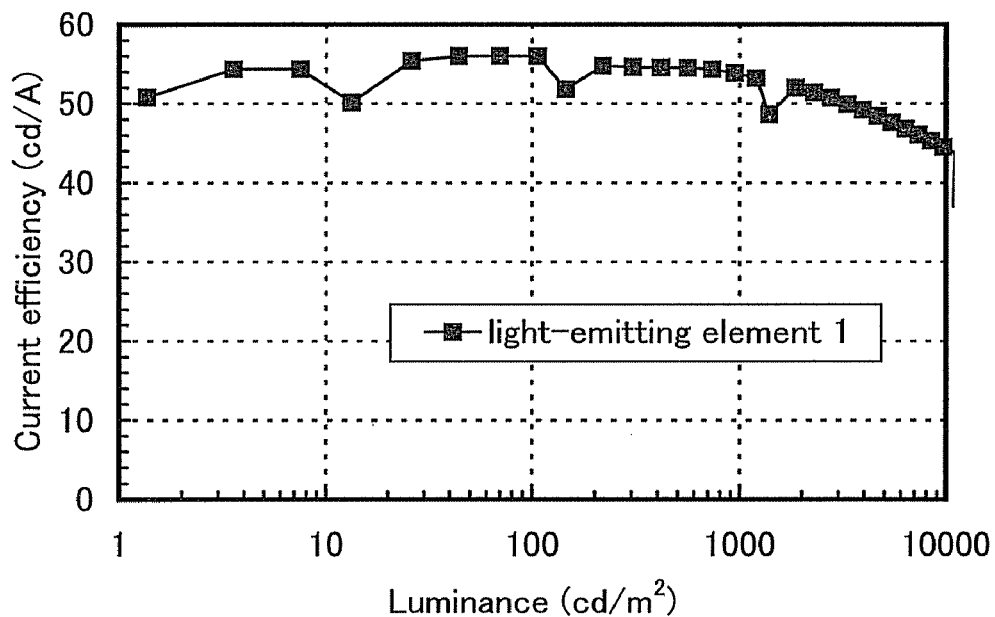
FIG. 18 shows luminance-current efficiency characteristics of the light-emitting element 1.

FIG. 16 shows the current density-luminance characteristic of the light-emitting element 1. In FIG. 16, the horizontal axis represents current density (mA/cm$^2$) and the vertical axis represents luminance (cd/m$^2$). In addition, the voltage-luminance characteristic thereof is shown in FIG. 17. In FIG. 17, the horizontal axis represents applied voltage (V) and the vertical axis represents luminance (cd/m$^2$). FIG. 18 shows the luminance-current efficiency characteristic thereof. In FIG. 18, the horizontal axis represents luminance (cd/m$^2$) and the vertical axis represents current efficiency (cd/A).

The current efficiency of the light-emitting element 1 was 54 cd/A at a luminance of 945 cd/m$^2$, which was extremely high efficiency. The external quantum efficiency at this time was 15%, and the voltage was 6.0 V.

Figure 19:
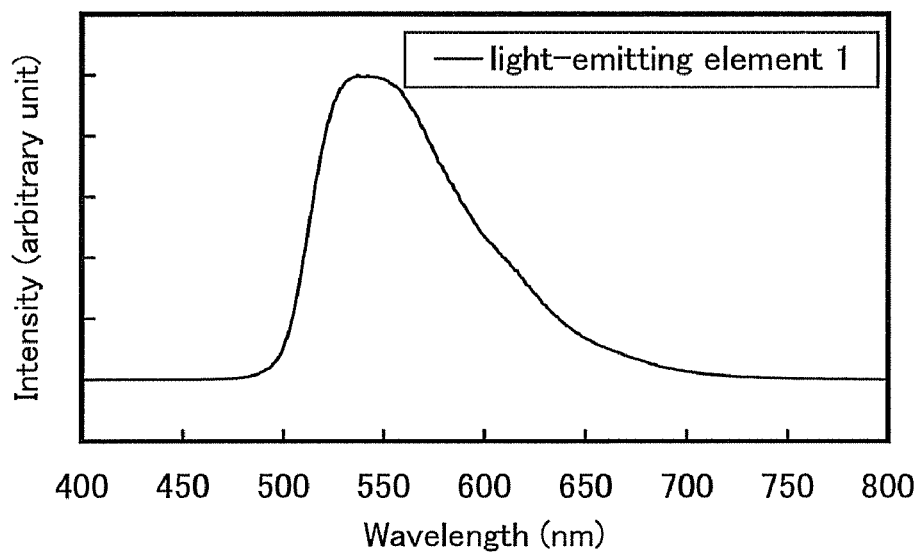
FIG. 19 shows an emission spectrum of the light-emitting element 1.

Further, emission spectrum at a current of 0.1 mA is shown in FIG. 19. In FIG. 19, the horizontal axis represents a wavelength (nm), whereas the vertical axis represents intensity (arbitrary unit). In FIG. 19, the obtained light-emitting element 1 exhibited green light emission from Ir(dmFppr)$_2$pic. A CIE chromaticity coordinate of the light-emitting element 1 at a luminance of 945 cd/m$^2$ was (x=0.40, y=0.59).

As described above, use of Z-CzPTAZ obtained in Example 1 as a host material and an electron-transporting material in a light-emitting layer made it possible to form a highly efficient light-emitting element.

Example 4

In this example, a light-emitting element having a structure different from that in Example 3 will be described. Structural formulae of materials used in this example have already been shown in the above example and thus illustration thereof is omitted. The element structure is the same as that in Example 3 (refer to FIG. 15).

A method for manufacturing a light-emitting element 2 of this example will be described below.

(Light-Emitting Element 2)

The light-emitting element 2 of this example is formed similarly to the light-emitting element 1 of Example 3 except the third layer 2105 functioning as a light-emitting layer and the fourth layer 2106 functioning as an electron-transporting layer. In the light-emitting element 2 of this example, the third layer 2105 and the fourth layer 2106 are formed as follows.

Z-CzPPz which is a heterocyclic compound synthesized in Example 2, PCBA1BP, and Ir(dmFppr)$_2$pic were co-evaporated over the second layer 2104, so that the third layer 2105 was formed as a light-emitting layer over the second layer 2104. Here, the weight ratio of Z-CzPPz:PCBA1BP:Ir(dmFppr)$_2$pic was adjusted to be 1:0.2:0.1 (=Z-CzPPz:PCBA1BP:Ir(dmFppr)$_2$pic). The thickness of the third layer 2105 was set to be 40 nm.

Then, Z-CzPPz which is a heterocyclic compound synthesized in Example 2 with a thickness of 10 nm and bathophenanthroline (abbreviation: BPhen) with a thickness of 20 nm were stacked in this order over the third layer 2105 with evaporation to form the fourth layer 2106 as an electron-transporting layer.

Note that, in the above evaporation process, evaporation was all performed by a resistance heating method.

Table 2 below shows the element structure of the light-emitting element 2.

TABLE 2

| | |
|---|---|
| second electrode 2108 | Al 200 nm |
| fifth layer 2107 | LiF 1 nm |
| fourth layer 2106 | BPhen 20 nm |
| | Z-CzPPz 10 nm |
| third layer 2105 | Z-CzPPz:PCBA1BP:Ir(dmFppr)$_2$pic (=1:0.2:0.1) 40 nm |
| second layer | PCBA1BP 10 nm |
| first layer 2103 | NPB:MoOx(=4:2) 50 nm |
| first electrode 2102 | ITSO 110 nm |

The light-emitting element 2 thus obtained was sealed in a glove box under a nitrogen atmosphere without being exposed to the atmosphere. Then, the operating characteristic of the light-emitting element 2 was measured. Note that the measurement was carried out at room temperature (in an atmosphere kept at 25° C.).

Figure 20:
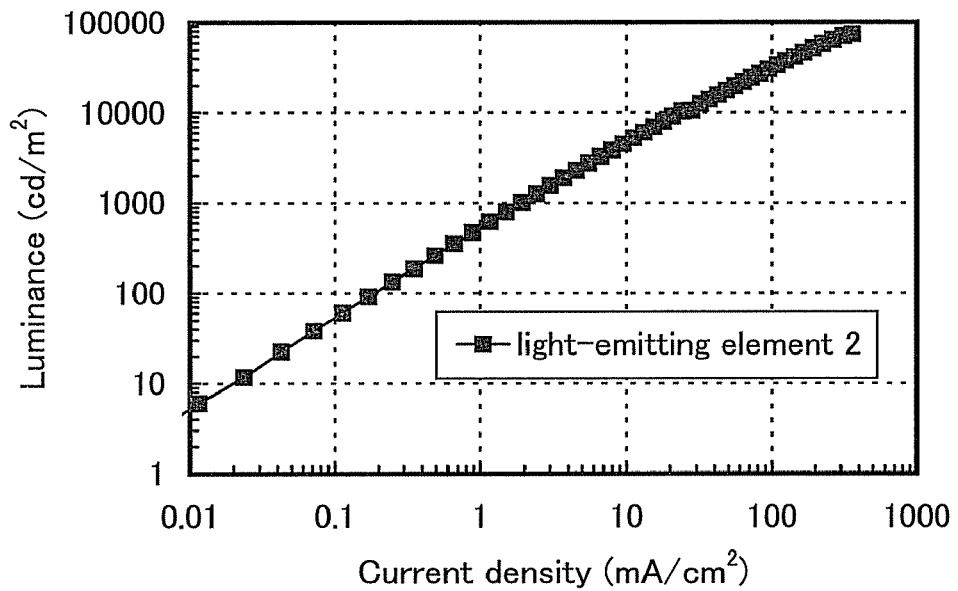
FIG. 20 shows current density-luminance characteristics of a light-emitting element 2.
Figure 21:
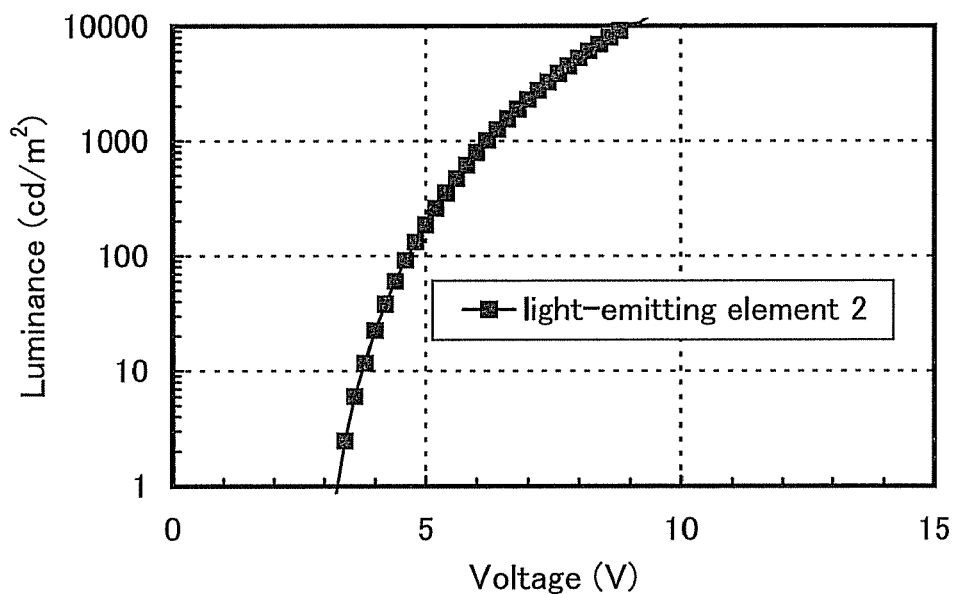
FIG. 21 shows voltage-luminance characteristics of the light-emitting element 2.
Figure 22:
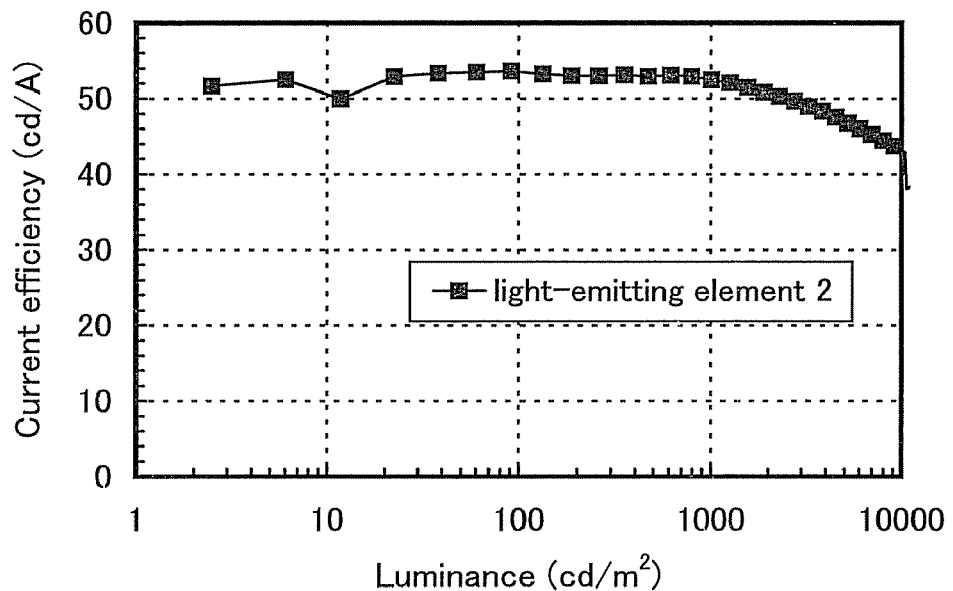
FIG. 22 shows luminance-current efficiency characteristics of the light-emitting element 2.

FIG. 20 shows the current density-luminance characteristic of the light-emitting element 2. In FIG. 20, the horizontal axis represents current density (mA/cm$^2$) and the vertical axis represents luminance (cd/m$^2$). In addition, the voltage-luminance characteristic thereof is shown in FIG. 21. In FIG. 21, the horizontal axis represents applied voltage (V) and the vertical axis represents luminance (cd/m$^2$). FIG. 22 shows the luminance-current efficiency characteristic thereof. In FIG. 22, the horizontal axis represents luminance (cd/m$^2$) and the vertical axis represents current efficiency (cd/A).

The current efficiency of the light-emitting element 2 was 52 cd/A at a luminance of 1008 cd/m$^2$, which was extremely high efficiency. The external quantum efficiency at this time was 15%, and the voltage was 6.2 V.

Figure 23:
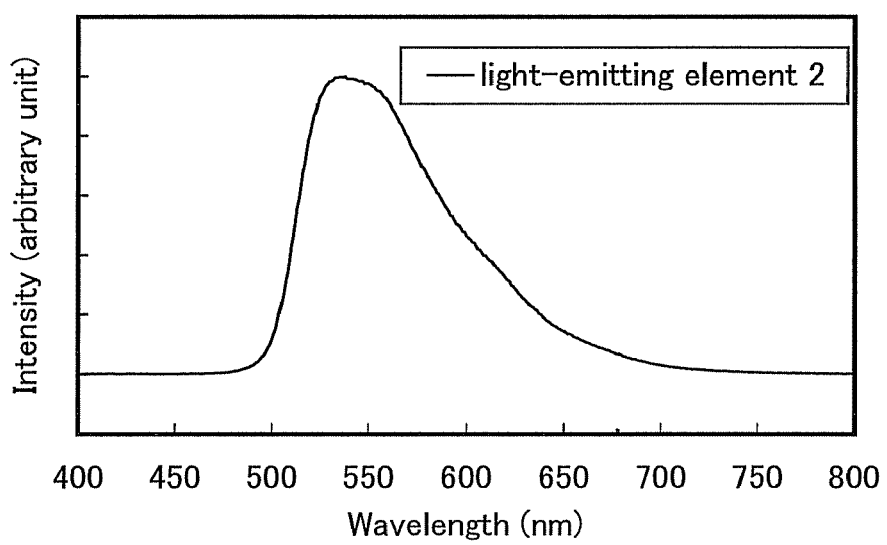
FIG. 23 shows an emission spectrum of the light-emitting element 2.

FIG. 23 shows the emission spectrum at a current of 0.1 mA. In FIG. 23, the horizontal axis represents wavelength (nm) and the vertical axis represents intensity (arbitrary unit). In FIG. 23, the obtained light-emitting element 2 exhibited green light emission from Ir(dmFppr)$_2$pic. A CIE chromaticity coordinate of the light-emitting element 2 at a luminance of 1008 cd/m$^2$ was (x=0.40, y=0.59).

As described above, use of Z-CzPPz obtained in Example 2 as a host material and an electron-transporting material in a light-emitting layer made it possible to form a highly efficient light-emitting element.

Reference Example

A method for synthesizing 4-phenyl-4'-(9-phenyl-9H-carbazol-3-yl)triphenylamine (abbreviation: PCBA1BP) used in Examples 3 and 4 will be specifically describe.

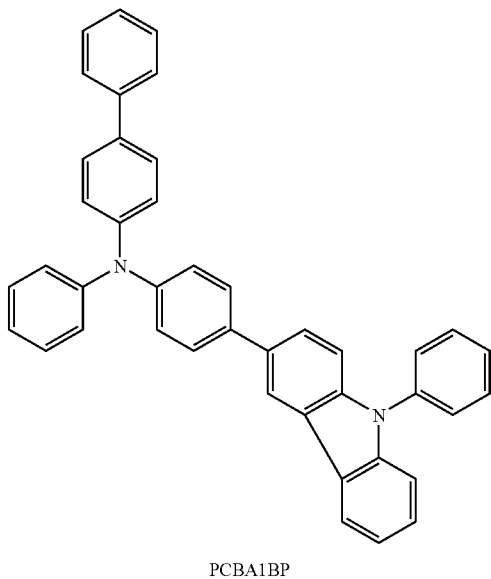

PCBA1BP

A synthetic scheme (R-1) of 4-phenyl-4'-(9-phenyl-9H-carbazol-3-yl)triphenylamine (abbreviation: PCBA1BP) is shown below.

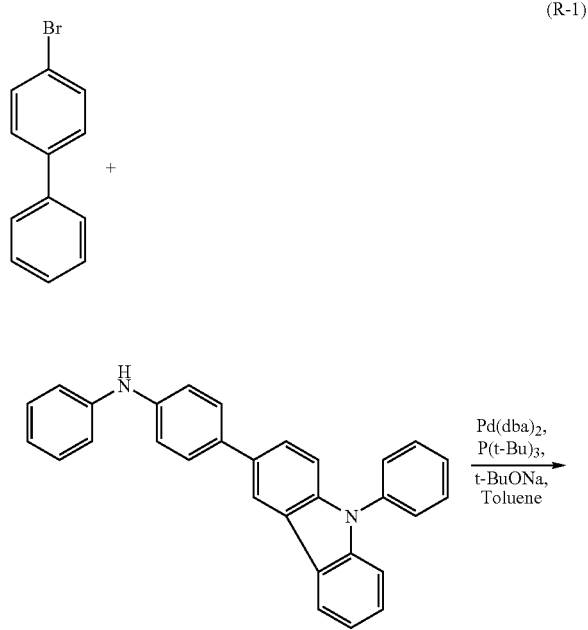

(R-1)

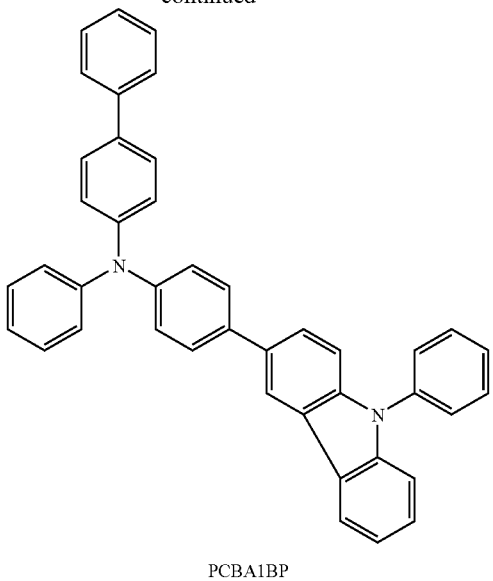

PCBA1BP

Into a 100 mL three-neck flask were put 2.0 g (4.9 mmol) of 4-(9-Phenyl-9H-carbazol-3-yl)diphenylamine, 1.1 g (4.9 mmol) of 4-bromophenyl, and 2.0 g (20 mmol) of sodium tert-butoxide, and the atmosphere in the flask was replaced with nitrogen. Then, 50 mL of toluene and 0.30 mL of tri(tert-butyl)phosphine (10 wt % hexane solution) were added to this mixture.

This mixture was degassed while being stirred under reduced pressure and then, 0.10 g of bis(dibenzylideneacetone)palladium(0) was added to the mixture. Next, this mixture was stirred at 80° C. for 5 hours to be reacted. After the reaction, toluene was added to the reaction mixture. The resulting suspension was subjected to suction filtration through Celite (produced by Wako Pure Chemical Industries. Ltd., Catalog No. 531-16855), alumina, and Florisil (produced by Wako Pure Chemical Industries, Ltd., Catalog No. 540-00135), so that a filtrate was obtained. The obtained filtrate was washed with a saturated aqueous solution of sodium carbonate and saturated saline in this order. Magnesium sulfate was added to an organic layer to dry the organic layer. After the drying, the mixture was subjected to suction filtration to remove the magnesium sulfate, and thus a filtrate was obtained.

The obtained filtrate was concentrated, and purified using silica gel column chromatography. The silica gel column chromatography was performed using a mixed solvent of toluene and hexane (toluene:hexane=1:9) first as a developing solvent, and then using a mixed solvent of toluene and hexane (toluene:hexane=3:7) as another developing solvent. A solid which was obtained by concentrating the obtained fraction was recrystallized with a mixed solvent of chloroform and hexane, so that 2.3 g of a white powdery solid was obtained in a yield of 84%.

Then, 1.2 g of the obtained white solid was sublimated and purified using a train sublimation method. The sublimation purification was performed at 280° C. for 20 hours under a reduced pressure of 7.0 Pa, with a flow rate of argon at 3 mL/min. Accordingly, 1.1 g of the white solid was obtained in a yield of 89%.

The obtained compound was measured with a nuclear magnetic resonance ($^1$H NMR) method. The measurement data is described below.

¹H NMR (DMSO-d₆, 300 MHz): δ (ppm)=7.05-7.20 (m, 7H), 7.28-7.78 (m, 21H), 8.34 (d, J=7.8 Hz, 1H), 8.57 (s, 1H)

From the measurement results, it is found that 4-phenyl-4'-(9-phenyl-9H-carbazol-3-yl)triphenylamine (abbreviation: PCBA1BP) was obtained.

Use of the 4-phenyl-4'-(9-phenyl-9H-carbazol-3-yl)triphenylamine (abbreviation: PCBA1BP) made it possible to form the light-emitting element 1 and the light-emitting element 2 described in the above examples.

This application is based on Japanese Patent Application serial no. 2009-086675 filed with Japan Patent Office on Mar. 31, 2009, the entire contents of which are hereby incorporated by reference.

What is claimed is:

1. A heterocyclic compound represented by a general formula (G1);

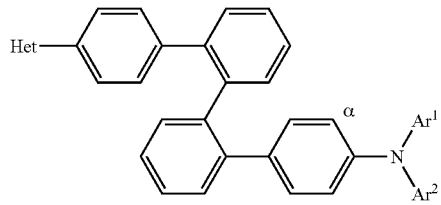

(G1)

wherein:

Ar¹ and Ar² independently represent a substituted or unsubstituted aryl group having 6 to 10 carbon atoms in a ring, Ar¹ and an α carbon atom are bonded to each other to form a carbazole skeleton and Ar² represents a substituted or unsubstituted aryl group having 6 to 10 carbon atoms in a ring, or Ar¹ and Ar² are bonded to each other to form a carbazole skeleton;

Het represents any one of substituents represented by the following general formulae (S1-1) and (S1-2);

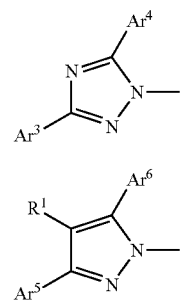

(S1-1)

(S1-2)

Ar³ to Ar⁶ independently represent a substituted or unsubstituted aryl group having 6 to 10 carbon atoms in a ring, and R¹ represents any one of a hydrogen atom, an alkyl group having 1 to 4 carbon atoms, an an aryl group having 6 to 10 carbon atoms in a ring.

2. The heterocyclic compound according to claim 1, wherein:

the heterocyclic compound is represented by a general formula (G2), and

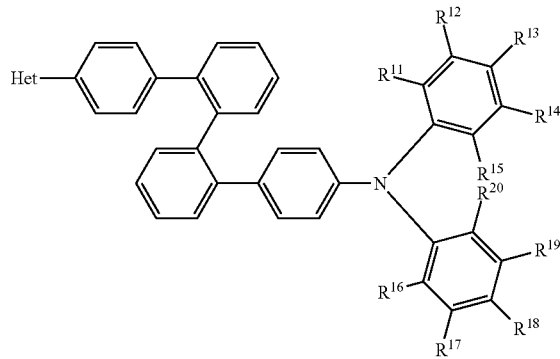

(G2)

R¹¹ to R²⁰ independently represent any one of a hydrogen atom, an alkyl group having 1 to 4 carbon atoms, and an aryl group having 6 to 10 carbon atoms in a ring.

3. The heterocyclic compound according to claim 2, wherein:

Het represents any one of substituents represented by the following general formulae (S2-1) and (S2-2), and

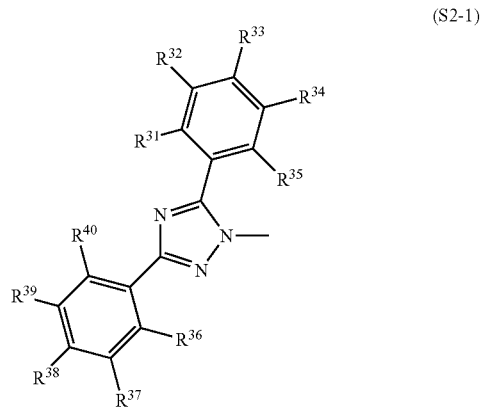

(S2-1)

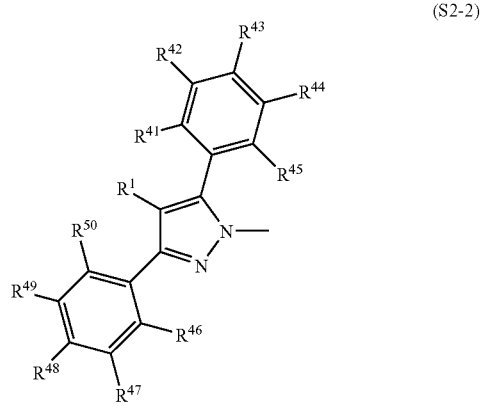

(S2-2)

R³¹ to R⁵⁰ independently represent any one of a hydrogen atom, an alkyl group having 1 to 4 carbon atoms, and an aryl group having 6 to 10 carbon atoms in a ring.

4. The heterocyclic compound according to claim 2, wherein:

Het represents any one of substituents represented by the following structural formula (S3-1) and general formula (S4-1)

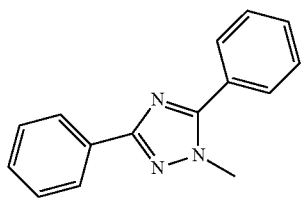

(S3-1)

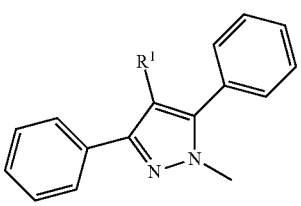

(S4-1)

5. The heterocyclic compound according to claim 2, wherein:

the heterocyclic compound is represented by a general formula (G3), and

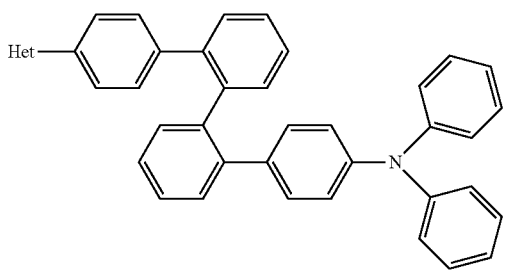

(G3)

Het represents any one of substituents represented by the following structural formula (S3-1) and general formula (S4-1)

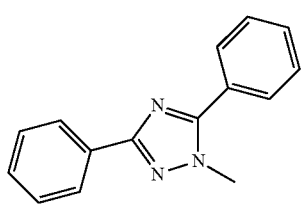

(S3-1)

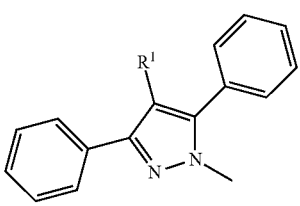

(S4-1)

6. The heterocyclic compound according to claim 2,

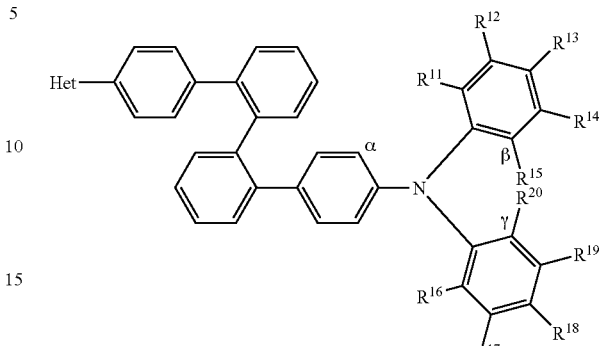

(G2)

wherein any two of an α carbon atom, a β carbon atom, and a γ carbon atom are bonded to each other to form a carbazole skeleton.

7. A light-emitting device comprising a light-emitting element, the light-emitting element comprising:
a pair of electrodes; and
a layer including a light-emitting substance and a heterocyclic compound between the pair of electrodes,
wherein:
the heterocyclic compound is represented by a general formula (G1);

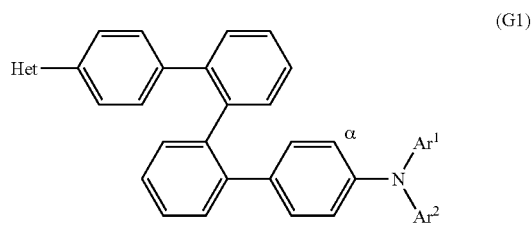

(G1)

Ar¹ and Ar² independently represent a substituted or unsubstituted aryl group having 6 to 10 carbon atoms in a ring, Ar¹ and an α carbon atom are bonded to each other to form a carbazole skeleton and Ar² represents a substituted or unsubstituted aryl group having 6 to 10 carbon atoms in a ring, or Ar¹ and Ar² are bonded to each other to form a carbazole skeleton;

Het represents any one of substituents represented by the following general formulae (S1-1) and (S1-2);

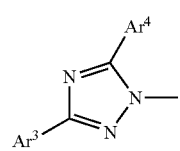

(S1-1)

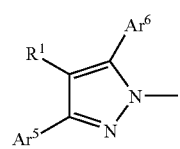

(S1-2)

Ar³ to Ar⁶ independently represent a substituted or unsubstituted aryl group having 6 to 10 carbon atoms in a ring, and R¹ represents any one of a hydrogen atom, an alkyl group having 1 to 4 carbon atoms, and an aryl group having 6 to 10 carbon atoms in a ring.

8. The light-emitting device according to claim 7, wherein the light-emitting substance is a phosphorescent compound.

9. The light-emitting device according to claim 7, wherein:

the heterocyclic compound is represented by a general formula (G2), and

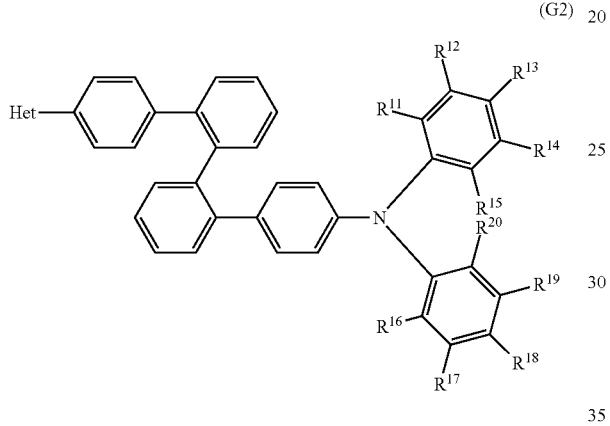

(G2)

R¹¹ to R²⁰ independently represent any one of a hydrogen atom, an alkyl group having 1 to 4 carbon atoms, and an aryl group having 6 to 10 carbon atoms in a ring.

10. The light-emitting device according to claim 9, wherein:

Het represents any one of substituents represented by the following general formulae (S2-1) and (S2-2), and

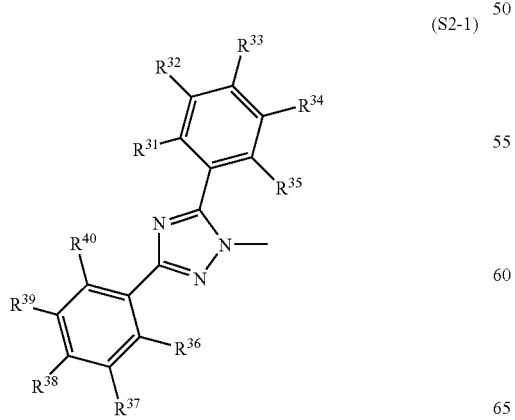

(S2-1)

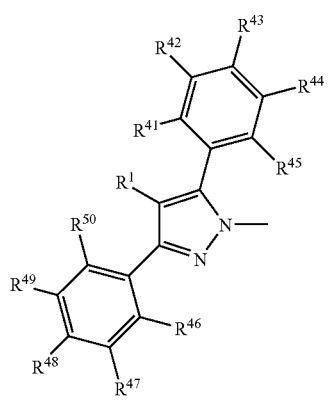

(S2-2)

R³¹ to R⁵⁰ independently represent any one of a hydrogen atom, an alkyl group having 1 to 4 carbon atoms, and an aryl group having 6 to 10 carbon atoms in a ring.

11. The light-emitting device according to claim 9, wherein:

Het represents any one of substituents represented by the following structural formula (S3-1) and general formula (S4-1)

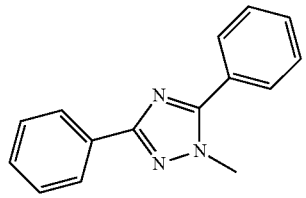

(S3-1)

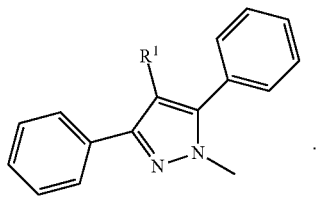

(S4-1)

12. The light-emitting device according to claim 9, wherein:

the heterocyclic compound is represented by a general formula (G3), and

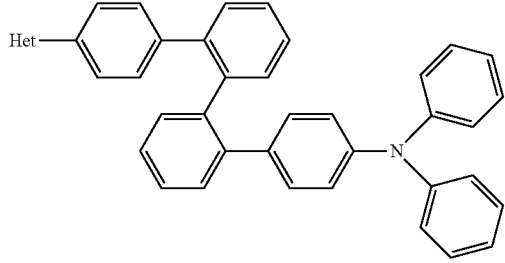

(G3)

Het represents any one of substituents represented by the following structural formula (S3-1) and general formula (S4-1)

(S3-1)
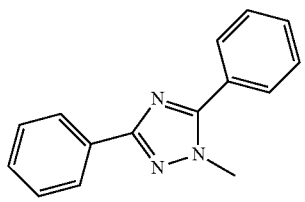

(S4-1)
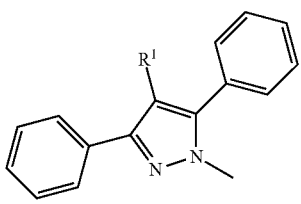

13. The light-emitting device according to claim 9, (G2)
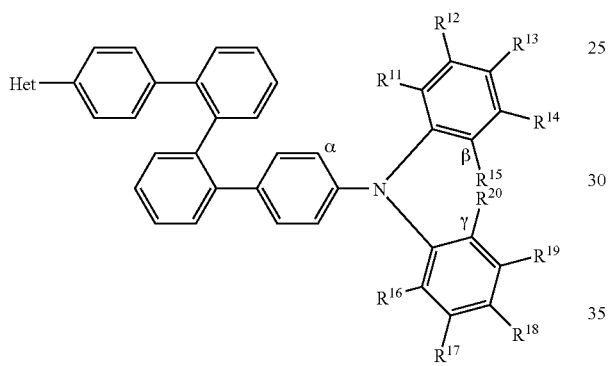

wherein any two of an α carbon atom, a β carbon atom, and a γ carbon atom are bonded to each other to form a carbazole skeleton.

14. A lighting device comprising a light-emitting element, the light-emitting element comprising:
a pair of electrodes; and
a layer including a light-emitting substance and a heterocyclic compound between the pair of electrodes,
wherein:
the heterocyclic compound is represented by a general formula (G1);

(G1)
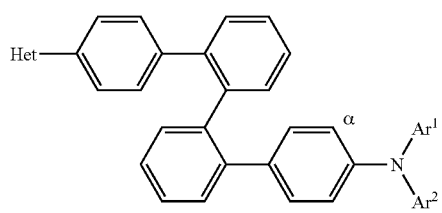

$Ar^1$ and $Ar^2$ independently represent a substituted or unsubstituted aryl group having 6 to 10 carbon atoms in a ring, $Ar^1$ and an α carbon atom are bonded to each other to form a carbazole skeleton and $Ar^2$ represents a substituted or unsubstituted aryl group having 6 to 10 carbon atoms in a ring, or $Ar^1$ and $Ar^2$ are bonded to each other to form a carbazole skeleton;

Het represents any one of substituents represented by the following general formulae (S1-1) and (S1-2);

(S1-1)
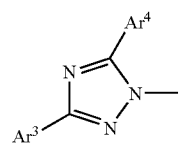

(S1-2)
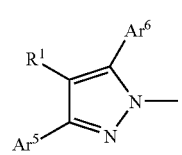

$Ar^3$ to $Ar^6$ independently represent a substituted or unsubstituted aryl group having 6 to 10 carbon atoms in a ring, and $R^1$ represents any one of a hydrogen atom, an alkyl group having 1 to 4 carbon atoms, and an aryl group having 6 to 10 carbon atoms in a ring.

15. The lighting device according to claim 14,
wherein the light-emitting substance is a phosphorescent compound.

16. The lighting device according to claim 14,
wherein:
the heterocyclic compound is represented by a general formula (G2), and (G2)
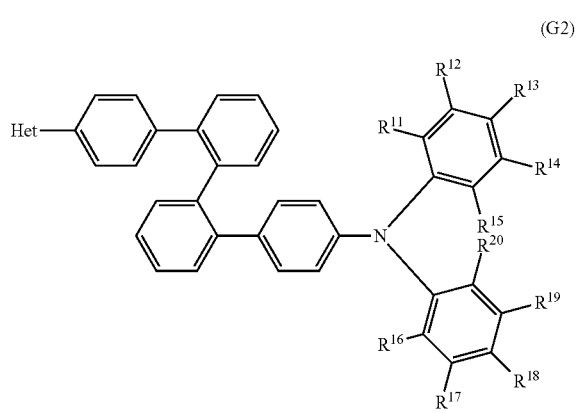

$R^{11}$ to $R^{20}$ independently represent any one of a hydrogen atom, an alkyl group having 1 to 4 carbon atoms, and an aryl group having 6 to 10 carbon atoms in a ring.

17. The lighting device according to claim 16,
wherein:
Het represents any one of substituents represented by the following general formulae (S2-1) and (S2-2), and

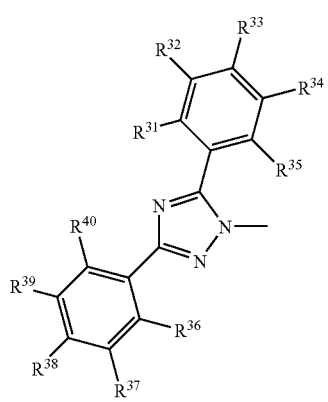
(S2-1)

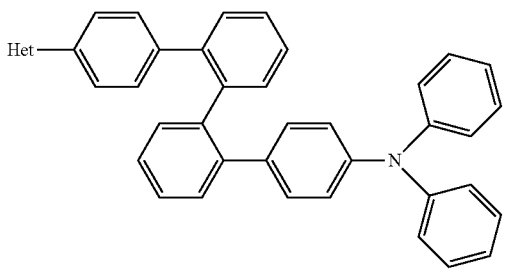
(G3)

Het represents any one of substituents represented by the following structural formula (S3-1) and general formula (S4-1)

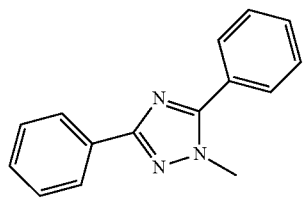
(S3-1)

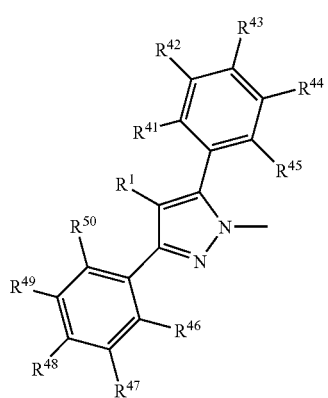
(S2-2)

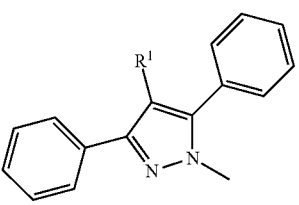
(S4-1)

R³¹ to R⁵⁰ independently represent any one of a hydrogen atom, an alkyl group having 1 to 4 carbon atoms, and an aryl group having 6 to 10 carbon atoms in a ring.

18. The lighting device according to claim 16, wherein:

Het represents any one of substituents represented by the following structural formula (S3-1) and general formula (S4-1)

20. The lighting device according to claim 16,

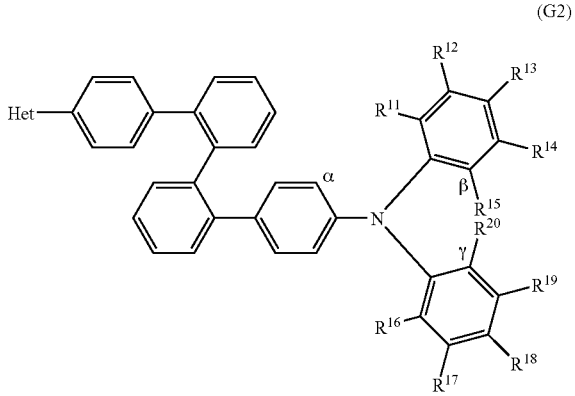
(G2)

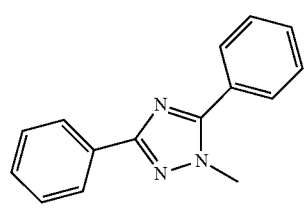
(S3-1)

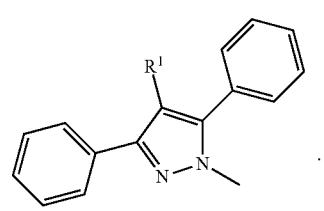
(S4-1)

19. The lighting device according to claim 16, wherein:

the heterocyclic compound is represented by a general formula (G3), and wherein any two of an α carbon atom, a β carbon atom, and a γ carbon atom are bonded to each other to form a carbazole skeleton.

21. An electronic appliance comprising a light-emitting element, the light-emitting element comprising:
a pair of electrodes; and
a layer including a light-emitting substance and a heterocyclic compound between the pair of electrodes,
wherein:
the heterocyclic compound is represented by a general formula (G1);

(G1)

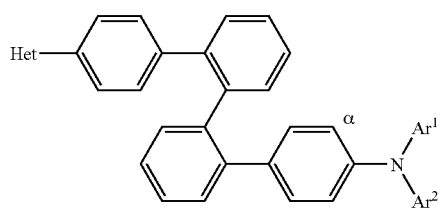

Ar¹ and Ar² independently represent a substituted or unsubstituted aryl group having 6 to 10 carbon atoms in a ring, Ar¹ and an α carbon atom are bonded to each other to form a carbazole skeleton and Ar² represents a substituted or unsubstituted aryl group having 6 to 10 carbon atoms in a ring, or Ar¹ and Ar² are bonded to each other to form a carbazole skeleton;

Het represents any one of substituents represented by the following general formulae (S1-1) and (S1-2);

(S1-1)

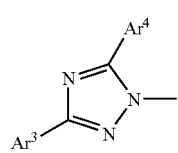

(S1-2)

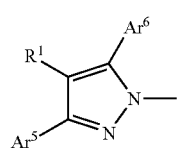

Ar³ to Ar⁶ independently represent a substituted or unsubstituted aryl group having 6 to 10 carbon atoms in a ring, and $R^1$ represents any one of a hydrogen atom, an alkyl group having 1 to 4 carbon atoms, and an aryl group having 6 to 10 carbon atoms in a ring.

22. The electronic appliance according to claim 21, wherein the light-emitting substance is a phosphorescent compound.

23. The electronic appliance according to claim 21, wherein:
the heterocyclic compound is represented by general formula (G2), and (G2)

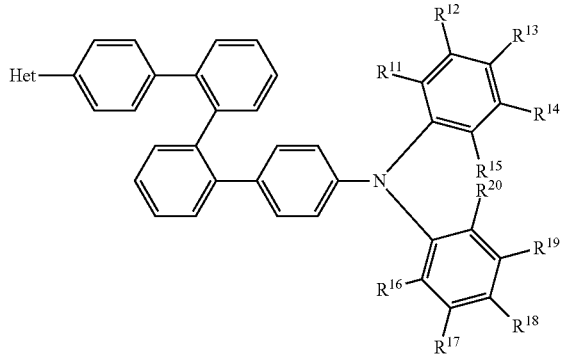

$R^{11}$ to $R^{20}$ independently represent any one of a hydrogen atom, an alkyl group having 1 to 4 carbon atoms, and an aryl group having 6 to 10 carbon atoms in a ring.

24. The electronic appliance according to claim 23, wherein:

Het represents any one of substituents represented by the following general formulae (S2-1) and (S2-2), and (S2-1)

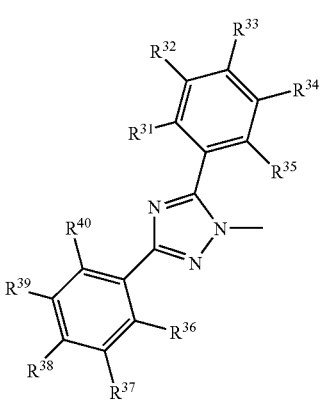

(S2-2)

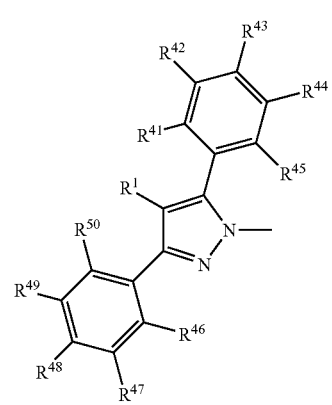

$R^{31}$ to $R^{50}$ independently represent any one of a hydrogen atom, an alkyl group having 1 to 4 carbon atoms, and an aryl group having 6 to 10 carbon atoms in a ring.

25. The electronic appliance according to claim 23, wherein:

Het represents any one of substituents represented by the following structural formula (S3-1) and general formula (S4-1)

(S3-1)

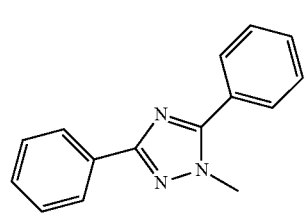

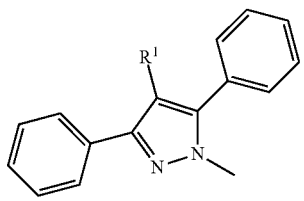
(S4-1)

26. The electronic appliance according to claim 23, wherein:

the heterocyclic compound is represented by a general formula (G3), and

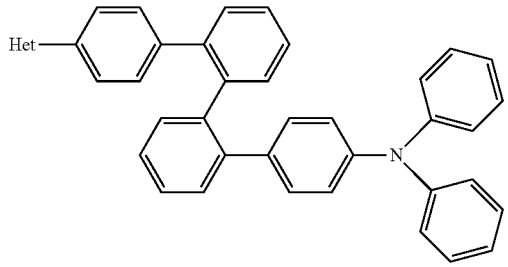
(G3)

Het represents any one of substituents represented by the following structural formula (S3-1) and general formula (S4-1)

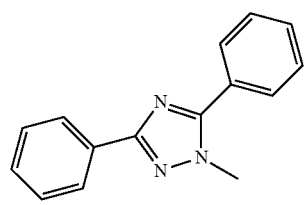
(S3-1)

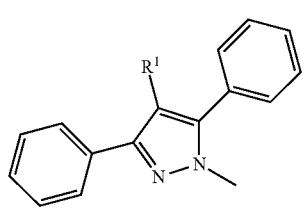
(S4-1)

27. The electronic appliance according to claim 23,

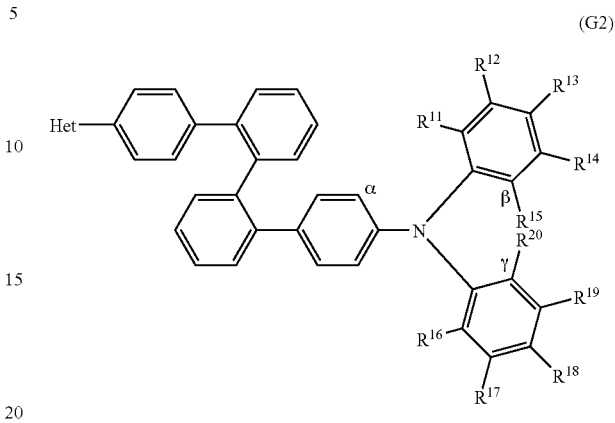
(G2)

wherein any two of an α carbon atom, a β carbon atom, and a γ carbon atom are bonded to each other to form a carbazole skeleton.

28. The heterocyclic compound according to claim 5,

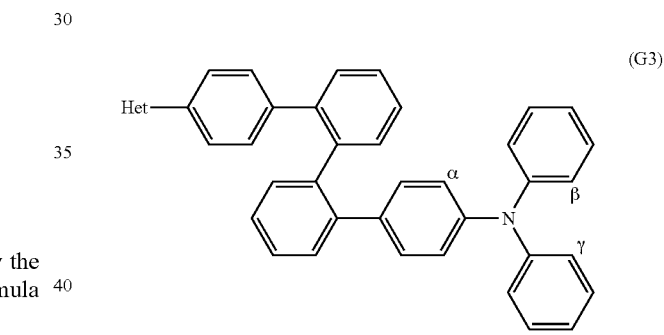
(G3)

wherein any two of an α carbon atom, a β carbon atom, and a γ carbon atom are bonded to each other to form a carbazole skeleton.

29. The light-emitting device according to claim 12,

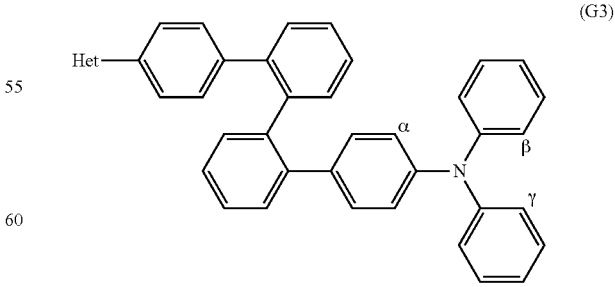
(G3)

wherein any two of an α carbon atom, a β carbon atom, and a γ carbon atom are bonded to each other to form a carbazole skeleton.

30. The lighting device according to claim 19,
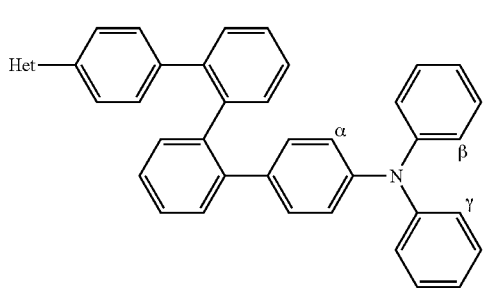
(G3)
wherein any two of an α carbon atom, a β carbon atom, and a γ carbon atom are bonded to each other to faun a carbazole skeleton.
31. The electronic appliance according to claim 26,
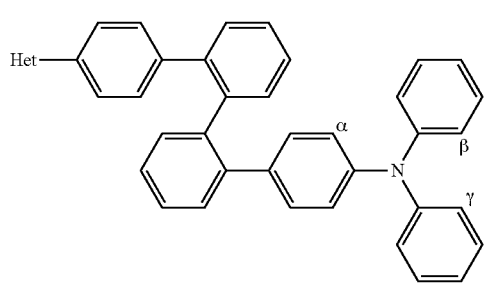
(G3)
wherein any two of an α carbon atom, a β carbon atom, and a γ carbon atom are bonded to each other to form a carbazole skeleton.
* * * * *

UNITED STATES PATENT AND TRADEMARK OFFICE
CERTIFICATE OF CORRECTION

PATENT NO. : 8,334,061 B2
APPLICATION NO. : 12/748902
DATED : December 18, 2012
INVENTOR(S) : Hiroko Nomura et al.

Page 1 of 1

It is certified that error appears in the above-identified patent and that said Letters Patent is hereby corrected as shown below:

In the Specification:

Column 89, Line 62; Change "(abbreviation: DNIPD)" to --(abbreviation: DNTPD)--.

Column 94, Line 31; Change "to be fowled" to --to be formed--.

In the Claims:

Claim 1, Column 119, Line 61; Change "an an aryl group" to --and an aryl group--.

Claim 30, Column 133, Line 19; Change "to faun a" to --to form a--.

Signed and Sealed this
Nineteenth Day of March, 2013

Teresa Stanek Rea
*Acting Director of the United States Patent and Trademark Office*